(12) United States Patent
Delaney

(10) Patent No.: US 8,759,508 B2
(45) Date of Patent: Jun. 24, 2014

(54) CHROMOPHORIC SILYL PROTECTING GROUPS AND THEIR USE IN THE CHEMICAL SYNTHESIS OF OLIGONUCLEOTIDES

(75) Inventor: Michael Oren Delaney, Dacono, CO (US)

(73) Assignee: GE Healthcare Dharmacon, Inc., Lafayette, CO (US)

( * ) Notice: Subject to any disclaimer, the term of this patent is extended or adjusted under 35 U.S.C. 154(b) by 423 days.

(21) Appl. No.: 12/600,829

(22) PCT Filed: May 16, 2008

(86) PCT No.: PCT/US2008/063834
§ 371 (c)(1),
(2), (4) Date: May 4, 2010

(87) PCT Pub. No.: WO2008/144472
PCT Pub. Date: Nov. 27, 2008

(65) Prior Publication Data
US 2010/0216984 A1    Aug. 26, 2010

Related U.S. Application Data

(60) Provisional application No. 60/938,991, filed on May 18, 2007.

(51) Int. Cl.
*C07H 19/10*    (2006.01)
*C07H 19/20*    (2006.01)
*C07H 21/00*    (2006.01)

(52) U.S. Cl.
USPC ............. 536/25.31; 536/25.34; 536/26.7; 536/26.8

(58) Field of Classification Search
None
See application file for complete search history.

(56) References Cited

U.S. PATENT DOCUMENTS

| | | | |
|---|---|---|---|
| 6,335,439 B1 | 1/2002 | Eleuteri et al. | |
| 6,737,236 B1 | 5/2004 | Pieken | |
| 8,026,349 B2 * | 9/2011 | Hartsel et al. ............. | 536/23.1 |
| 2005/0267300 A1 | 12/2005 | Manoharan et al. | |

FOREIGN PATENT DOCUMENTS

| | | |
|---|---|---|
| DE | 295 855 A5 | 11/1991 |
| WO | 96/41809 A1 | 12/1996 |
| WO | 9847910 | 10/1998 |
| WO | 99/00402 A1 | 1/1999 |
| WO | 0142505 | 6/2001 |
| WO | WO 03/023357 A2 | 3/2003 |
| WO | 03/101972 A1 | 12/2003 |
| WO | 2006/080509 A1 | 8/2006 |
| WO | 2006/116629 A1 | 11/2006 |
| WO | 2006-/127507 | 11/2006 |

OTHER PUBLICATIONS

Wilkinson et al. "Synthetic utility of glycosyl triazoles in carbohydrate chemistry." *Tetrahedron*, Aug. 21, 2006, 62(34), pp. 8115-8125. Abstract.

Tripathi, Snehlata et al., One-Pot Synthesis of TBMPS (bis [tert-butyl]-1pyrenylmethyl-silyl) Chloride as a Novel Fluorescent Silicon-Based Protecting Group for Protection of 5'-OH Nucleosides and its Use as Purification Handle in Oligonucleotide Synthesis, Nucleosides, Nucleotides and Nucleic Acids, 2005, vol. 24, No. 9, pp. 1345-1351.

Japanese Intellectual Property Office, Notice of Reasons for Rejection, Japanese Application No. 2010-509467, Mar. 12, 2013.

Tripathi, Snehlata et al., Synthesis and application of bis-(tert-butyl)-1-methyl-prenyl-silyl chloride as a 5'-hdroxyl protecting group for nucleoside and as a fluorescent purification handle in oligonucleotide synthesis, Nucleic Acid research Supplement, 2002, vol. 2, twenty-nine Symposium on Nucl., pp. 117-118.

Japanese Intellectual Property Office, Decision of Rejection, Japanese Application No. 2010-509467, Aug. 13, 2013.

Heather Brummel McCuen et al.; "Synthesis of Mixed Sequence Borane Phosphonate Dna"; Journal of the American Chemical Society, vol. 128, No. 25, 1 Jun. 2006, pp. 8138-8139, XP055087772, ISSN: 0002-7863, DOI: 10.1021/ja061757e.

European Search Report, Application No. 08780666.7-1452 / 2147009, PCT/US2008063834, dated Jan. 9, 2014.

Michael O. Delaney et al., "Chromophoric 5'-O-Silyl Protection of N-Protected 2'-ACE Ribonucleosides for Solid-Phase RNA Synthesis", In: "Current Protocols in Nucleic Acid Chemistry", Mar. 26, 2008, John Wiley & Sons, Inc. Hoboken, NJ, USA, XP055087240, ISBN: 978-0-47-114270-6, DOI: 10.1002/0471142700.nc0214s32.

* cited by examiner

*Primary Examiner* — Lawrence E Crane
(74) *Attorney, Agent, or Firm* — Dorf & Nelson LLP; Scott D. Locke, Esq.

(57) ABSTRACT

The compounds are of class of chromophoric 1,2,3-triazolyl equipped silyl linking groups that are useful in the chemical synthesis of RNA. An example of a nucleoside comprising this group is

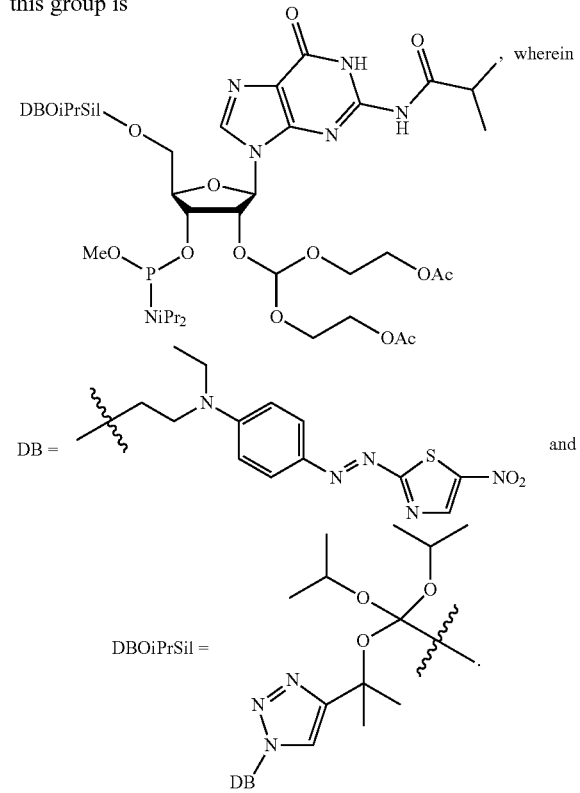

14 Claims, 26 Drawing Sheets

Key: a) Solvent, acid scavenger  b) Cu(I), Solvent, tertiary base

Key: a) Isopropanol, 0 °C (27 %) b) 2-Methyl-3-butyn-2-ol, Et₃N, CH₂Cl₂, 0 °C (55%)

Key: a) 2-Methyl-3-butyn-2-ol, Et$_3$N, CH$_2$Cl$_2$, 0 °C (39%)

Key: a) 2-Methyl-3-butyn-2-ol, Et₃N, CH₂Cl₂, 0 °C (49%)

Key: a) $CH_3SO_3Cl$, $Et_3N$, $CH_2Cl_2$, 0 °C; b) $NaN_3$, DMSO 70 °C (96%) c) NaOAc, AcOH, $H_2O$, 0 °C (75%)

Key: a) Nitrosylsulfuric acid, AcOH, PrOH, b) 2, (40%)

Key: a) NH$_2$(CH$_2$)$_2$OH, DMSO 70 °C (78%); b) CH$_3$SO$_3$Cl, Et$_3$N, CH$_2$Cl$_2$ 0° C (96%); c) NaN$_3$, EtOH 75 °C (65%)

Key: a) Triethylorthoformate, PTSA, dioxane (75%)

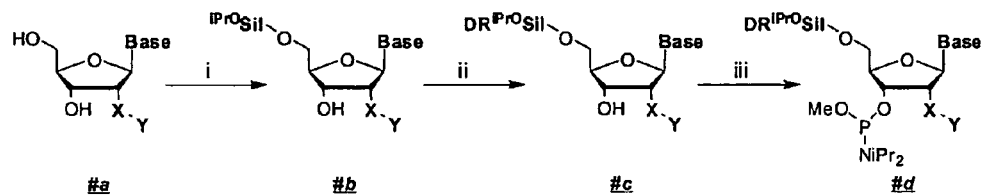
Key: i) DIA, CH$_2$Cl$_2$, DPMBSiCl, 0° C; ii) CuI, iPr$_2$NEt, DR-N$_3$, Toluene; iii) POMe, DIA, SEt-Tet, CH$_2$Cl$_2$.
| Base | X | Y | Yield % (step i, ii, iii) | # |
|---|---|---|---|---|
| Adenosine$^{(NiBu)}$ | O | ACE | 4b: 89; 4c: 77; 4d: 86 | 4 |
| Guanosine$^{(NiBu)}$ | O | ACE | 5b: 78; 5c: 71; 5d: 81 | 5 |
| Cytidine$^{(NAc)}$ | O | ACE | 6b: 86; 6c: 80; 6d: 80 | 6 |
| Uridine | O | ACE | 7b: 80; 7c: 70; 7d: 80 | 7 |
| Adenosine$^{(NiBu)}$ | O | Me | 8b: 85; 8c: 79; 8d: 92 | 8 |
| Guanosine$^{(NiBu)}$ | O | Me | 9b: 67; 9c: 60; 9d: 87 | 9 |
| Cytidine$^{(NAc)}$ | O | Me | 10b: 55; 10c: 87; 10d: 85 | 10 |
| Uridine | O | Me | 11b: 27; 11c: 67; 11d: 90 | 11 |
| Cytidine$^{(NAc)}$ | F | -- | 12b: 55; 12c: 67; 12d: 92 | 12 |
| Uridine | F | -- | 13b: 75; 13c: 59; 13d: 86 | 13 |
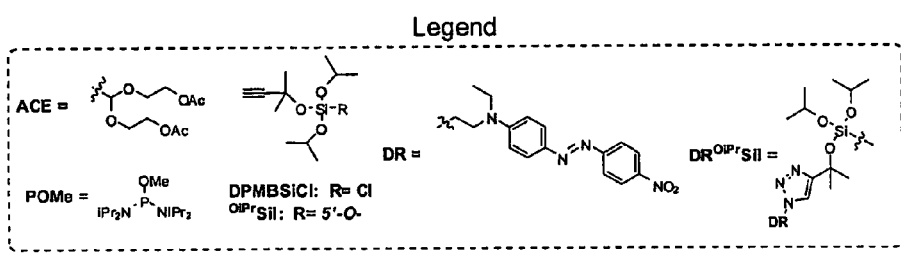
Figure 9

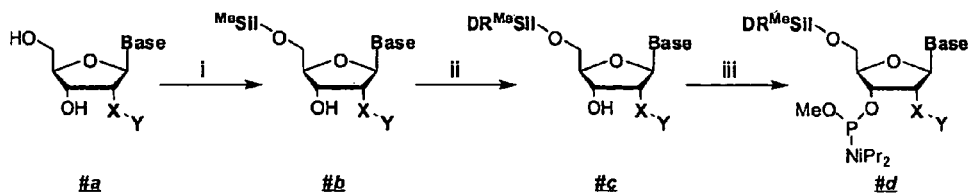
Key: i) DIA, CH$_2$Cl$_2$, DMMBSiCl, 0 °C; ii) CuI, iPr$_2$NEt, DR-N$_3$, Toluene; iii) POMe, DIA, SEt-Tet, CH$_2$Cl$_2$.
| Base | X | Y | Yield % (step i, ii, iii) | # |
|---|---|---|---|---|
| Adenosine$^{(NiBu)}$ | O | ACE | 14b: 85; 14c: 90; 14d: 66 | 14 |
| Guanosine$^{(NiBu)}$ | O | ACE | 15b: 83; 15c: 93; 15d: 88 | 15 |
| Cytidine$^{(NAc)}$ | O | ACE | 16b: 73; 16c: 98; 16d: 86 | 16 |
| Uridine | O | ACE | 17b: 94; 17c: 92; 17d: 92 | 17 |
| Adenosine$^{(NiBu)}$ | O | Me | 18b: 70; 18c: 89; 18d: 79 | 18 |
| Guanosine$^{(NiBu)}$ | O | Me | 19b: 54; 19c: 44; 19d: 67 | 19 |
| Cytidine$^{(NAc)}$ | O | Me | 20b: 74; 20c: 86; 20d: 58 | 20 |
| Uridine | O | Me | 21b: 81; 21c: 59; 21d: 75 | 21 |
| Cytidine$^{(NAc)}$ | F | -- | 22b: 30; 22c: 50; 22d: 63 | 22 |
| Uridine | F | -- | 23c: 49 (2-steps); 23d: 75 | 23 |
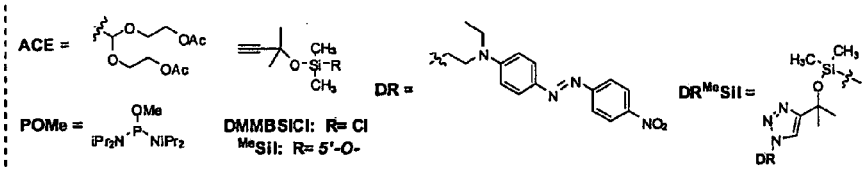
Figure 10

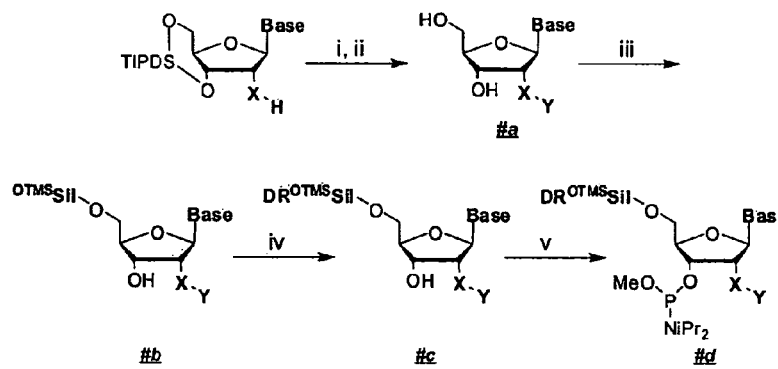

Key: i) MP orthoformate, PPTS, tBDMS-pentanedione, CH$_2$Cl$_2$, ii) HF-TEMED, AcN; iii) DIA, CH$_2$Cl$_2$, BTMBSiCl, 0 °C; iv) CuI, iPr$_2$NEt, DR-N$_3$, Toluene; v) POMe, DIA, SEt-Tet, CH$_2$Cl$_2$

| Base | X | Y | Yield % (step ii, iii, iv, v) | # |
|---|---|---|---|---|
| Adenosine$^{(NiBu)}$ | O | MP | *24a:* 80; *24b:* 83; *24c:* 95; *24d:* 92 | *24* |
| Guanosine$^{(NiBu)}$ | O | MP | *25a:* 52; *25b:* 77; *25c:* 84; *25d:* 96 | *25* |
| Cytidine$^{(Ndmf)}$ | O | MP | *26a:* 30; *26b:* 79; *26c:* 79; *26d:* 86 | *26* |
| Uridine | O | MP | *27a:* 63; *27b:* 80; *27c:* 91; *27d:* 82 | *27* |
| Adenosine$^{(NiBu)}$ | O | Me | *28b:* 77; *28c:* 83; *28d:* 95 | *28* |
| Guanosine$^{(NiBu)}$ | O | Me | *29b:* 71; *29c:* 80; *29d:* 87 | *29* |
| Cytidine$^{(NAc)}$ | O | Me | *30b:* 77; *30c:* 88; *30d:* 90 | *30* |
| Uridine | O | Me | *31b:* 75; *31c:* 83; *31d:* 91 | *31* |
| Cytidine$^{(NAc)}$ | F | -- | *32b:* 65; *32c:* 72; *32d:* 65 | *32* |
| Uridine | F | -- | *33b:* 78; *33c:* 78; *33d:* 82 | *33* |

Legend

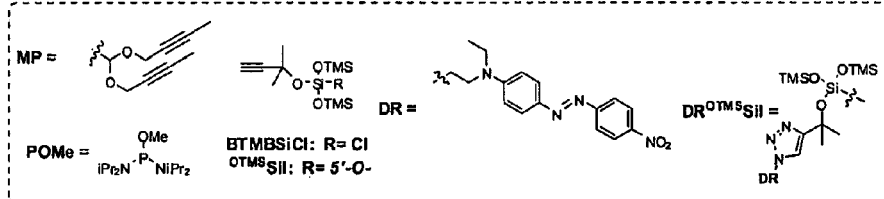

Figure 11

Key: i) CuI, iPr₂NEt, DB-N₃, Toluene (76 %); ii) POMe, DIA, SEt-Tet, CH₂Cl₂ (53 %).

Key: i) CuI, iPr₂NEt, AR-N₃, Toluene (81 %); ii) POMe, DIA, SEt-Tet, CH₂Cl₂ (83 %).

a) Diluted with $CH_3CN$ ($\lambda$ max = 470 nM)
b) Diluted with $H_2O$ ($\lambda$ max = 486 nM)
c) Diluted with 0.5 M $H_2SO_4$ ($\lambda$ max = 540 nM)

a) Diluted with $CH_3CN$ ($\lambda$ max = 566 nM)
b) Diluted with $H_2O$ ($\lambda$ max = 592 nM)
c) Diluted with 0.5 M $H_2SO_4$ ($\lambda$ max = 600 nM)

a) Diluted with $CH_3CN$ ($\lambda$ max = 490 nM)
b) Diluted with $H_2O$ ($\lambda$ max = 496 nM)
c) Diluted with 0.5 M $H_2SO_4$ ($\lambda$ max = 496nM)

SEQUENCE LISTING

<160> NUMBER OF SEQ ID NOS: 8

<210> SEQ ID NO 1
<211> LENGTH: 33
<212> TYPE: RNA
<213> ORGANISM: Artificial sequence
<220> FEATURE:
<223> OTHER INFORMATION: Synthetic

<400> SEQUENCE: 1
gcaacugcua cgugucaugc agcuucaugc cau                              33

<210> SEQ ID NO 2
<211> LENGTH: 21
<212> TYPE: RNA
<213> ORGANISM: Artificial sequence
<220> FEATURE:
<223> OTHER INFORMATION: Synthetic

<400> SEQUENCE: 2
ucgaucgauc gaucgaucga u                                           21

<210> SEQ ID NO 3
<211> LENGTH: 12
<212> TYPE: RNA
<213> ORGANISM: Artificial sequence
<220> FEATURE:
<223> OTHER INFORMATION: Synthetic

<400> SEQUENCE: 3
aaaaaaaaaa aa                                                     12

<210> SEQ ID NO 4
<211> LENGTH: 12
<212> TYPE: RNA
<213> ORGANISM: Artificial sequence
<220> FEATURE:
<223> OTHER INFORMATION: Synthetic

<400> SEQUENCE: 4
cccccccccc cc                                                     12

<210> SEQ ID NO 5
<211> LENGTH: 11
<212> TYPE: RNA
<213> ORGANISM: Artificial sequence
<220> FEATURE:
<223> OTHER INFORMATION: Synthetic

```
<400> SEQUENCE: 5
gggggggggg g                                                    11

<210> SEQ ID NO 6
<211> LENGTH: 11
<212> TYPE: RNA
<213> ORGANISM: Artificial sequence
<220> FEATURE:
<223> OTHER INFORMATION: Synthetic

<400> SEQUENCE: 6
uuuuuuuuuu u                                                    11

<210> SEQ ID NO 7
<211> LENGTH: 45
<212> TYPE: RNA
<213> ORGANISM: Artificial sequence
<220> FEATURE:
<223> OTHER INFORMATION: Synthetic

<400> SEQUENCE: 7
agcuaucgga ucgacuauca guuaggcgga uucaauuggc uagcu                45

<210> SEQ ID NO 8
<211> LENGTH: 21
<212> TYPE: RNA
<213> ORGANISM: Artificial sequence
<220> FEATURE:
<223> OTHER INFORMATION: Synthetic

<400> SEQUENCE: 8
guuaaccguc ugacucaugu u                                         21
```

CHROMOPHORIC SILYL PROTECTING GROUPS AND THEIR USE IN THE CHEMICAL SYNTHESIS OF OLIGONUCLEOTIDES

RELATED APPLICATIONS

This application is a National Stage Application of PCT/US2008/063834, filed 16 May 2008, in the name of Dharmacon, Inc., a U.S. national corporation, applicant for the designation of all countries except the U.S., and Michael Oren Delaney, a citizen of the U.S., applicant for the designation of the U.S. only, and claims priority to U.S. Provisional Patent Application Ser. No. 60/938,991filed on 18 May 2007, to the extent appropriate, a claim of priority is made to each of the above disclosed applications.

BACKGROUND OF THE INVENTION

Protecting groups are critical and ubiquitous features of modern synthetic organic chemistry, due to the need to carry out site-specific transformations in the presence of potentially numerous similar reactive functionalities. Since the early 1980's, research into protective groups for virtually any reactive functionality—amine, alcohol, carbonyl, carboxylic acid, thiol, phosphate to name a few—has produced thousands of reagents having a wide variety of chemical stabilities and applications. Indeed, the choice of compatible and orthogonal protection for complex organic syntheses is often one of the key factors in designing a successful synthetic scheme (see, e.g., *Greene's Protective Groups in Organic Synthesis*, (Wuts et al., fourth edition, Wiley Interscience, John Wiley and Sons Inc., 2007) herein incorporated by reference).

The use of silyl protecting groups for the temporary blocking of reactive hydroxyl functionalities has become commonplace in synthetic organic chemistry. Groups such as trimethylsilyl, t-butyldimethylsilyl, phenyldimethylsilyl and triphenysilyl are routinely used for the protection of hydroxyl groups as silyl ethers in the preparation of simple alcohols as well as of complex natural products. These groups have the advantage of being removable by treatment with fluoride ion, a reagent to which most other protecting groups exhibit good to excellent stability.

Silyl ether protecting groups have also been applied to the synthesis of oligonucleotides (U.S. Pat. Nos. 5,889,136, 6,008,400, 6,111,086, 6,590,093; Scaringe, *Methods* 23, 206-217 (2001); Scaringe, et al., *J. Am. Chem. Soc.* 120, 11820-11821 (1998); herein incorporated by reference).

Despite the significant improvements realized with the 5'-silyl-2'-orthoester synthesis invention, 5'-silyl ether protecting groups described in the literature are not visibly colored and do not provide the convenient colorimetric capability, an attribute that is advantageous for assessing coupling efficiency and is a feature of, for example, the traditional dimethoxytrityl (or DMT) 5'-protecting group. Thus, currently available reagents do not allow for visual detection of the deprotection step (i.e, via release of the silyl protecting group) which would allow evaluation of the coupling step. Additionally, it is desirable that each deprotection solution be collected in its entirety and the quantity of the protecting group released determined spectrophotometrically. Each value so obtained could then be ratioed with the immediately preceding value to obtain a nearly quantitative measure of the coupling efficiency for each cycle.

Thus, a need exists for a complement to the efficient chemical synthesis of RNA utilizing the 5'-silyl-2'-orthoester synthesis platform with a colorimetrical assay to monitor the individual coupling efficiencies of each synthesis cycle.

SUMMARY OF THE INVENTION

The present invention provides 5'-silyl-protecting groups comprising a chromophore or other detectable moiety that allows for the visible determination of the coupling efficiency of each cycle. The released chromophore can further be collected and quantified spectrophotometrically to determine the coupling efficiency for the chemical step.

The present invention provides compounds of the formula (I):

$$C-Q-O-Si(R_1)(R_2)-N$$

wherein C is a chromophore or other detectable moiety;

Q is selected from the group consisting of optionally substituted aliphatic, aryl, heteroaryl, cycloalkyl or heterocycloalkyl;

$R_1$ and $R_2$ are independently selected from the group consisting of optionally substituted $C_{1-8}$ alkyl, cycloalkyl, heterocycloalkyl, aryl, heteroaryl, $C_{1-8}$ alkyloxy, cycloalkyloxy, heterocycloalkyloxy, alkylsilyloxy and arylsilyloxy; and N is a glycosylamine or abasic moiety.

In one embodiment, Q is selected from the group consisting of optionally substituted $C_{2-12}$ alkene, $C_{3-8}$ aryl, heteroaryl, cycloalkyl and heterocycloalkyl. In another, Q is selected from the group consisting of $C_{2-12}$ alkene and $C_{3-8}$ heterocycloalkene wherein the heteroatoms are selected from N and O. In a further embodiment, Q is optionally substituted $C_{5-6}$ heteroaryl wherein the heteroatoms are selected from N and O. In one preferred embodiment, Q is oxazole or triazole, preferably, 1,2,3-triazole.

In one aspect of the invention, N is a modified or unmodified nucleotide or nucleoside or abasic molecule.

In another, $R_1$ and $R_2$ are independently selected from the group consisting of optionally substituted $C_{1-8}$ alkyloxy and alkylsilyloxy.

The invention also provides compounds or intermediates of the formula (II):

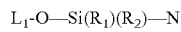

$$L_1-O-Si(R_1)(R_2)-N$$

wherein $L_1$ is selected from the group consisting of azide, alkyne, alkene, maleimide, nitrile oxide, aldehyde or imine.

The invention also provides methods of synthesizing compounds of formula (I), comprising:

reacting a compound of formula (II): $L_1-O-Si(R_1)(R_2)-N$ with a compound of formula $C-L_2$, wherein $L_1$ and $L_2$ are independently selected from the group consisting of azide, alkyne, alkene, maleimide, nitrile oxide, aldehyde or imine; and whereby $L_1$ and $L_2$ react to form the moiety Q.

The method may further comprise:

reacting a compound of formula $L_1-O-Si(R_1)(R_2)(X)$ with N; and purifying via chromatography the resulting product (II) 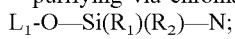 $L_1-O-Si(R_1)(R_2)-N$;

wherein X is halo, imidazolyl, triazolyl, tetrazolyl, trifluoromethanesulfonyl, alkylamino or dialkylamino.

The method may additionally comprise reacting a compound of formula $L_1-O-Si(R_1)(R_2)(X)$ with N; and purifying via chromatography the resulting product (II) $L_1-O-Si(R_1)(R_2)-N$; wherein X is chloro.

Additionally, the method may comprise reacting a compound of formula $L_1-O-Si(R_1)(R_2)(X)$ with N; and purifying via chromatography the resulting product (II) $L_1-O-Si(R_1)(R_2)-N$; wherein X is N,N-diisopropylamino.

The invention also provides methods of synthesizing oligonucleotides comprising:

a. providing a substrate bound nucleoside or oligonucleotide comprising a 5'-protecting group of the formula C-Q-O—Si(R$_1$)(R$_2$)—;

b. removing the 5'-protecting group and providing a free 5'-OH group;

c. reacting a nucleoside monomer comprising a 3'-phosphoramidite with the substrate bound nucleoside or oligonucleotide whereby the 3'-phosphoramidite is coupled to the 5'-OH of the substrate bound nucleoside or oligonucleotide to form a phosphotriester; and d. reacting the phosphotriester formed in (c) with a suitable oxidizing agent to convert it to a phosphate triester.

The steps a through d may be repeated one or more times to create an oligo of desired length. The nucleoside monomer and substrate bound nucleoside or oligonucleotide may further comprise a 2'-protecting group. The method may further comprise detecting the 5'-protected group removed in step b.

BRIEF DESCRIPTION OF THE DRAWINGS

FIG. 9 shows synthetic scheme describing the synthesis of 5'-DR(OiPr)$_2$-Silyl-Nucleoside phosphoramidites (4c-13d).

FIG. 10 shows synthetic scheme describing the synthesis of 5'-DR(Me)$_2$-Silyl-Nucleoside phosphoramidites (14d-23d).

FIG. 11 shows synthetic scheme describing the synthesis of 5'-DR(OTMS)$_2$-Silyl-Nucleoside phosphoramidites (24d-33d).

DETAILED DESCRIPTION OF THE INVENTION

Figure 1:
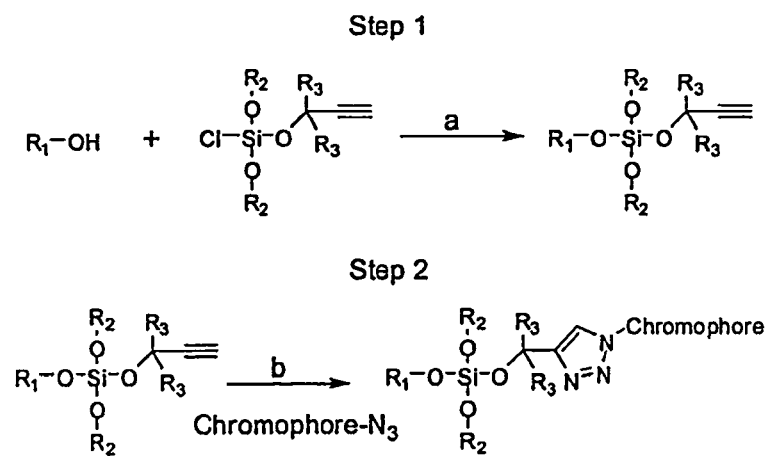
FIG. 1 shows a general two-step procedure for protecting a hydroxyl group with a chromophoric-silyl protecting group.
Figure 2:
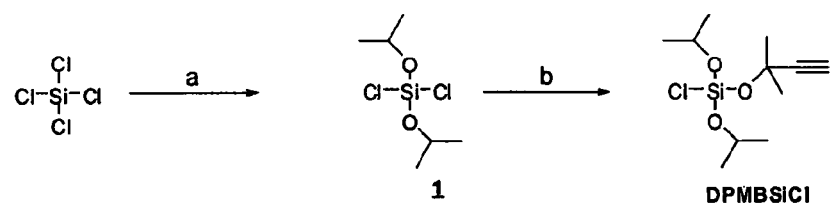
FIG. 2 shows synthetic conditions to prepare the intermediate functionalized chlorosilane DPMBSiCl.
Figure 3:
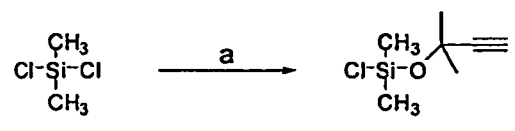
FIG. 3 shows synthetic conditions to prepare the intermediate functionalized chlorosilane DMMBSiCl.
Figure 4:
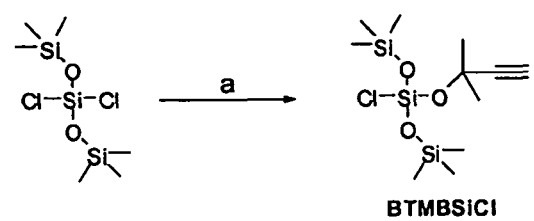
FIG. 4 shows synthetic conditions to prepare the intermediate functionalized chlorosilane BTMBSiCl.
Figure 5:
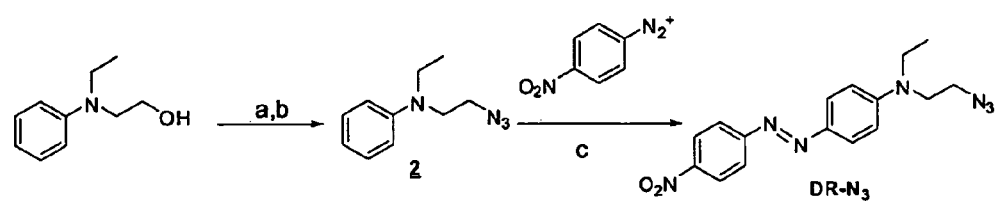
FIG. 5 shows synthetic conditions to prepare Disperse Red azide (DR-N$_3$).
Figure 6:
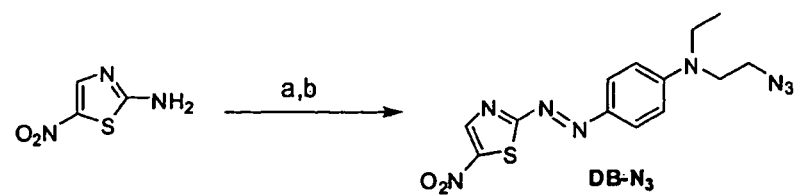
FIG. 6 shows synthetic conditions to prepare Disperse Blue azide (DB-N$_3$).
Figure 7:
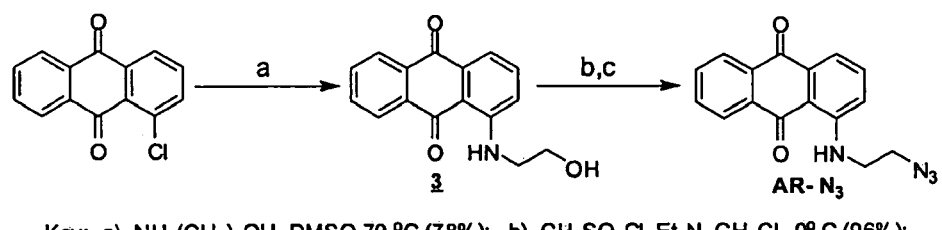
FIG. 7 shows synthetic conditions to make 1-(2-azidoethylamino)anthracene-9,10-dione (AR-N$_3$).
Figure 8:
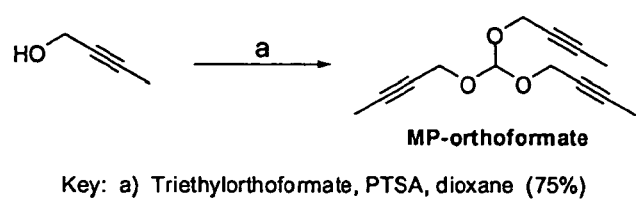
FIG. 8 shows synthetic conditions to prepare the intermediate MP-orthoformate.
Figure 12:
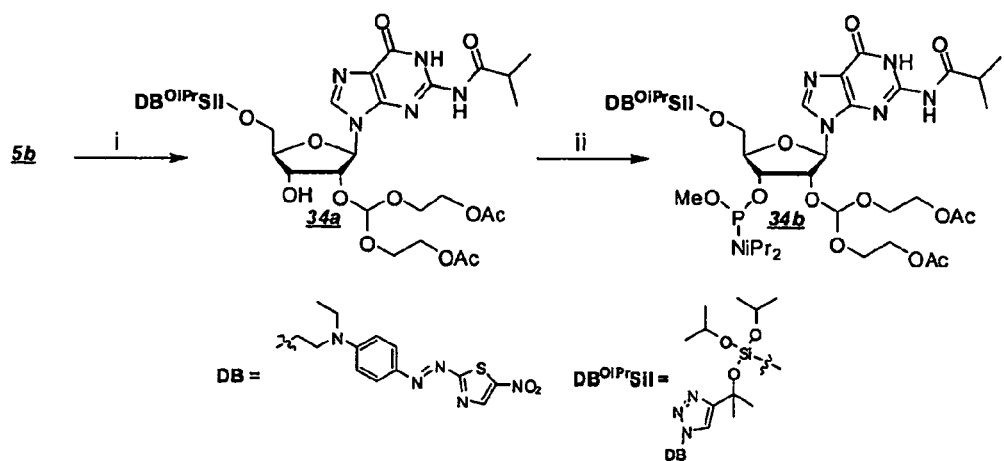
FIG. 12 shows synthetic scheme describing the synthesis of 5'-DB(OiPr)$_2$-Silyl-2'-ACE-rG(n-ibu) phosphoramidite (34b).
Figure 13:
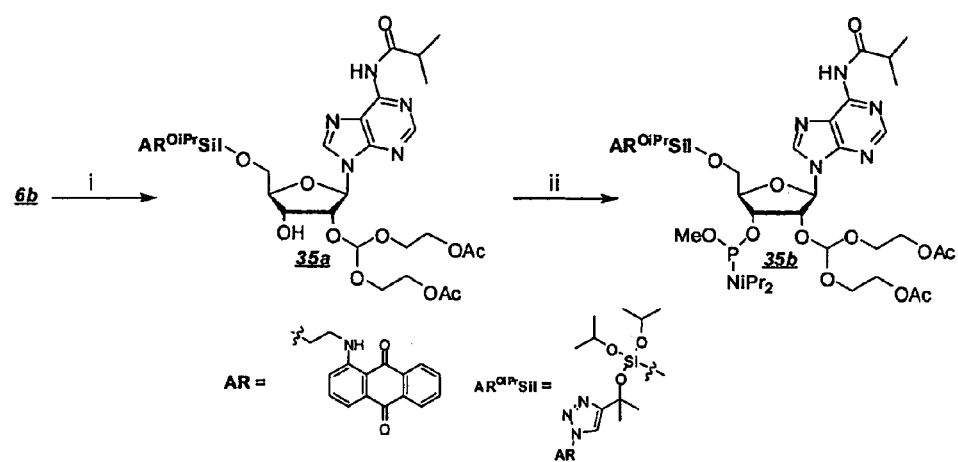
FIG. 13 shows synthetic scheme describing the synthesis of 5'-AR(OiPr)-2-Silyl-2'-ACE-rA(n-ibu) phosphoramidite (35b).
Figure 14:
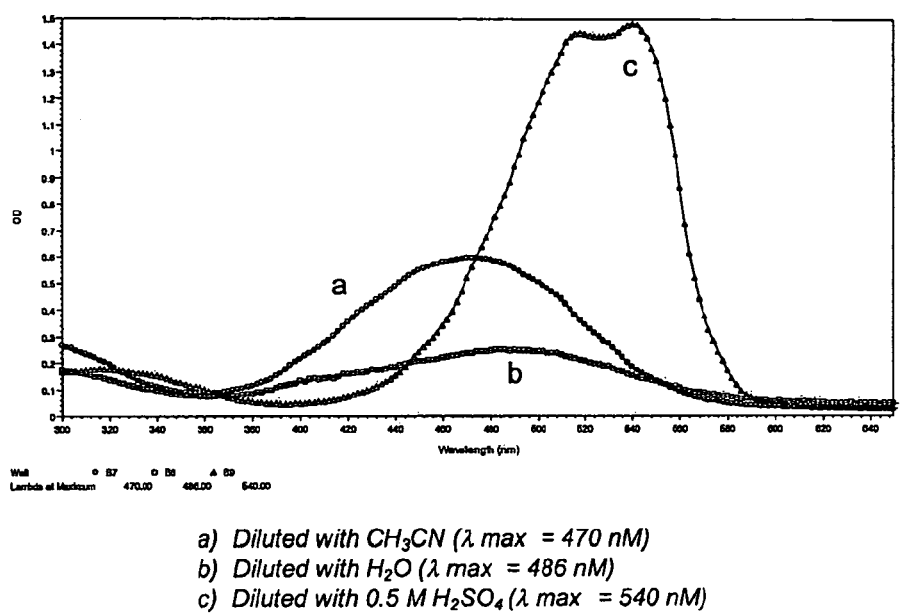
FIG. 14 shows UV-Vis spectral overlay of DR response in different solvents.

As used herein, the following definitions shall apply unless otherwise indicated.

The phrase "optionally substituted" is used interchangeably with the phrase "substituted or unsubstituted." Unless otherwise indicated, an optionally substituted group may have a substituent at each substitutable position of the group, and each substitution is independent of any other. Also, combinations of substituents or variables are permissible only if such combinations result in stable compounds. In addition, unless otherwise indicated, functional group radicals are independently selected. Where "optionally substituted" modifies a series of groups separated by commas (e.g., "optionally substituted A, B or C"; or "A, B or C optionally substituted with"), it is intended that each of the groups (e.g., A, B and C) is optionally substituted.

The term "chromophore" means any element that is capable of absorbing light of a suitable wavelength. Suitable chromophores include, by way of example, azo dyes (e.g., Disperse Red 1, Disperse Red 13, Disperse Orange 1, Disperse Orange 3, Disperse Yellow 7, Methyl Red, Methyl Orange), anthraquinone dyes (e.g., Disperse Blue 1, Alizarin), triphenylmethane dyes (e.g., Malachite Green, fuschine, Crystal Violet), coumarin dyes (e.g., 7-amino-4-methylcoumarin, 6,8-difluoro-7-hydroxycoumarin), xanthene dyes (e.g., fluorescein, naphthofluorescein, eosin, erythrosin), rhodamine dyes (e.g., rhodamine B, rhodamine 6G, rhodamine 110, tetramethylrhodamine, X-rhodamine), and cyanine dyes (e.g., Cy2, Cy3, Cy3.5, Cy5, Cy5.5, Cy7) or substituted derivatives thereof. Preferably, the chromophore has a significant extinction coefficient (>5,000 M$^{-1}$cm$^{-1}$) in the visible wavelength range 350 nm to 800 nm. Most preferably, the chromophore has a significant extinction coefficient (>10,000 M$^{-1}$cm$^{-1}$) in the visible wavelength range 450 nm to 550 nm. Included are chromophores having fluorescent or phosphorescent properties, whereby some of the light absorbed is emitted as light of a longer wavelength.

The term "aliphatic" or "aliphatic group" as used herein means a straight-chain or branched C$_{1-12}$ hydrocarbon chain that is completely saturated or that contains one or more units of unsaturation, or a monocyclic C$_{3-8}$ hydrocarbon or bicyclic C$_{8-12}$ hydrocarbon that is completely saturated or that contains one or more units of unsaturation, but which is not aromatic (also referred to herein as "carbocycle" or "cycloalkyl"), that has a single point of attachment to the rest of the molecule wherein any individual ring in said bicyclic ring system has 3-7 members. For example, suitable aliphatic groups include, but are not limited to, linear or branched alkyl, alkenyl, alkynyl groups and hybrids thereof such as (cycloalkyl)alkyl, (cycloalkenyl)alkyl or (cycloalkyl)alkenyl. Also included are substituted mono-, di- and tri-substituted silyloxy groups (alkylsilyloxy) such as trialkylsilyloxy, in each case where the alkyl groups may be the same or different. Examples include trimethylsilyloxy, triethylsilyloxy, tripropylsilyloxy, triisopropylsilyloxy, t-butyldimethylsilyloxy, and the like. In one embodiment, alkylsilyloxy means $C_{1-4}$ alkylsilyloxy.

The terms "alkyl," "alkoxy" (also referred to as "alkyloxy"), "hydroxyalkyl," "alkoxyalkyl" and "alkoxycarbonyl," used alone or as part of a larger moiety include both straight and branched chains containing one to twelve carbon atoms, including by way of example, methyl, ethyl, n-propyl, isopropyl, n-butyl, s-butyl, t-butyl, etc., and the corresponding alkoxy analogs. The terms "alkenyl" and "alkynyl" used alone or as part of a larger moiety shall include both straight and branched chains containing two to twelve carbon atoms.

The terms "haloalkyl," "haloalkenyl" and "haloalkoxy" means alkyl, alkenyl or alkoxy, as the case may be, substituted with one or more halogen atoms. The term "halogen" or "halo" means F, Cl, Br or I.

The term "heteroatom" means nitrogen, oxygen, or sulfur and includes any oxidized form of nitrogen and sulfur, and the quaternized form of any basic nitrogen.

The term "aryl" used alone or in combination with other terms, refers to monocyclic, bicyclic or tricyclic carbocyclic ring systems having a total of five to fourteen ring members, wherein at least one ring in the system is aromatic and wherein each ring in the system contains 3 to 8 ring members. The term "aryl" may be used interchangeably with the term "aryl ring". The term "aralkyl" or "arylalkyl" refers to an alkyl group substituted by an aryl. The term "aralkoxy" or "arylalkoxy" refers to an alkoxy group substituted by an aryl. The "arylsilyloxy" refers to a mono-, di- and tri-substituted silyloxy groups (e.g., triarylsilyoxy) (it will be understood that the silyl may be substituted with one or more other groups (e.g., alkyl) where mono- or di-substituted with aryl).

As used herein, where a ring is defined to contain or comprise x to y members, it is understood that the total number of member atoms (e.g., carbon or heteroatoms) making up the ring is x, y or any integer between x and y. By way of example, a ring comprising 3 to 8 carbon or heteroatoms may be ring containing 3, 4, 5, 6, 7 or 8 ring members.

The term "heterocycloalkyl," "heterocycle," "heterocyclyl" or "heterocyclic" as used herein means monocyclic, bicyclic or tricyclic ring systems having 5, 6, 7, 8, 9, 10, 11, 12, 13 or 14 ring members in which one or more ring members is a heteroatom, wherein each ring in the system contains 3, 4, 5, 6, 7 or 8 ring members and is non-aromatic.

The term "heteroaryl," used alone or in combination with other terms, refers to monocyclic, bicyclic and tricyclic ring systems having a total of 5, 6, 7, 8, 9, 10, 11, 12, 13 or 14 ring members, and wherein: 1) at least one ring in the system is aromatic; 2) at least one ring in the system contains one or more heteroatoms; and 3) each ring in the system contains 3, 4, 5, 6 or 7 ring members. The term "heteroaryl" may be used interchangeably with the term "heteroaryl ring" or the term "heteroaromatic". Examples of heteroaryl rings include, but are not limited to, 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 3-pyrazolyl, 4-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, and benzoisoxazolyl. The term "heteroaralkyl" refers to an alkyl group substituted by a heteroaryl. The term "heteroarylalkoxy" refers to an alkoxy group substituted by a heteroaryl.

An aryl (including aralkyl, aralkoxy, aryloxyalkyl and the like) or heteroaryl (including heteroaralkyl, heteroarylalkoxy and the like) group may contain one or more substituents. Suitable substituents on an unsaturated carbon atom of an aryl, heteroaryl, aralkyl or heteroaralkyl group are selected from halogen; haloalkyl; —$CF_3$; —R; —OR; —SR; 1,2-methylenedioxy; 1,2-ethylenedioxy; protected OH (such as acyloxy); phenyl (Ph); Ph substituted with R; —O(Ph); —O-(Ph) substituted with R; —$CH_2$(Ph); —$CH_2$(Ph) substituted with R; —$CH_2CH_2$(Ph); —$CH_2CH_2$(Ph) substituted with R; —$NO_2$; —CN; —$N(R)_2$; —NRC(O)R; —$NRC(O)N(R)_2$; —$NRCO_2R$; —NRNRC(O)R; —NR—$NRC(O)N(R)_2$; —$NRNRCO_2R$; —C(O)C(O)R; —C(O)$CH_2$C(O)R; —$CO_2R$; —C(O)R; —C(O)$N(R)_2$; —OC(O)$N(R)_2$; —$S(O)_2$R;

—$SO_2N(R)_2$; —S(O)R; —$NRSO_2N(R)_2$; —$NRSO_2R$; —C(=S)$N(R)_2$; —C(=NH)—$N(R)_2$; —$(CH_2)_y$NHC(O)R; —$(CH_2)_y$R; —$(CH_2)_y$NHC(O)NHR; —$(CH_2)_y$NHC(O)OR; —$(CH_2)_y$NHS(O)R; —$(CH_2)_y$NHSO_2R; or —$(CH_2)_y$NHC(O)CH((V)_z—R)(R) wherein each R is independently selected from hydrogen, optionally substituted aliphatic (preferably $C_{1-6}$), an unsubstituted heteroaryl or heterocyclic ring (preferably $C_{5-6}$), phenyl (Ph), —O(Ph), or —$CH_2$(Ph)-$CH_2$(Ph), wherein y is 0-6; z is 0-1; and V is a linker group. When R is aliphatic, it may be substituted with one or more substituents selected from —$NH_2$, —NH($C_{1-4}$ aliphatic), —N($C_{1-4}$ aliphatic)$_2$, —S(O)($C_{1-4}$ aliphatic), —$SO_2$($C_{1-4}$ aliphatic), halogen, ($C_{1-4}$ aliphatic), —OH, —O—($C_{1-4}$ aliphatic), —$NO_2$, —CN, —$CO_2H$, —$CO_2$($C_{1-4}$ aliphatic), —O(halo $C_{1-4}$ aliphatic) or -halo($C_{1-4}$ aliphatic); wherein each $C_{1-4}$ aliphatic is unsubstituted.

An aliphatic group or a non-aromatic heterocyclic ring may contain one or more substituents. Suitable substituents on a saturated carbon of an aliphatic group or of a non-aromatic heterocyclic ring are selected from those listed above for the unsaturated carbon of an aryl or heteroaryl group and the following: =O, =S, =NNHR, =$NN(R)_2$, =N—, =NNHC(O)R, =$NNHCO_2$(alkyl), =$NNHSO_2$(alkyl), or =NR, where each R is independently selected from hydrogen or an optionally substituted aliphatic (preferably $C_{1-6}$). When R is aliphatic, it may be substituted with one or more substituents selected from —$NH_2$, —NH($C_{1-4}$ aliphatic), —N($C_{1-4}$ aliphatic)$_2$, halogen, —OH, —O—($C_{1-4}$ aliphatic), —$NO_2$, —CN, —$CO_2H$, —$CO_2$($C_{1-4}$ aliphatic), —O(halo $C_{1-4}$ aliphatic), or -halo($C_{1-4}$ aliphatic); wherein each $C_{1-4}$ aliphatic is unsubstituted.

Substituents on a nitrogen of a non-aromatic heterocyclic ring are selected from —R, —$N(R)_2$, —C(O)R, —C(O)OR, —C(O)C(O)R, —C(O)$CH_2$C(O)R, —$SO_2$R, —$SO_2N(R)_2$, —C(=S)$N(R)_2$, —C(=NH)—$N(R)_2$ or —$NRSO_2R$; wherein each R is independently selected from hydrogen, an optionally substituted aliphatic (preferably $C_{1-6}$), optionally substituted phenyl (Ph), optionally substituted —O(Ph), optionally substituted —$CH_2$(Ph), optionally substituted —$CH_2CH_2$(Ph), or an unsubstituted heteroaryl or heterocyclic ring (preferably 5-6 membered). When R is a $C_{1-6}$ aliphatic group or a phenyl ring, it may be substituted with one or more substituents selected from —$NH_2$, —NH($C_{1-4}$ aliphatic), —N($C_{1-4}$ aliphatic)$_2$, halogen, —($C_{1-4}$ aliphatic), —OH, —O—($C_{1-4}$ aliphatic), —$NO_2$, —CN, —$CO_2H$, —$CO_2$($C_{1-4}$ aliphatic), —O(halo $C_{1-4}$ aliphatic) or -halo($C_{1-4}$ aliphatic); wherein each $C_{1-4}$ aliphatic is unsubstituted.

The term "nucleotide" as used herein, refers to a heterocyclic nitrogenous base in N-glycosidic linkage with a phosphorylated sugar. Nucleotides are recognized in the art to include natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and others). Some of the non-limiting examples of chemically modified and other natural nucleic acid bases that can be introduced into nucleic acids include, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, quesosine, 2-thiouridine, 4-thiouridine, wybutosine, wybutoxosine, 4-acetylcytidine, 5-(carboxyhydroxymethyl)uridine, 5'-carboxymethylaminomethyl-2-thiouridine, 5-carboxymethylaminomethyluridine, beta-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N-6-isopentenyladenosine, β-D-mannosylqueosine, uridine-5-oxyacetic acid, 2-thiocytidine, threonine derivatives and others. By "modified bases" in this aspect is meant nucleotide bases other than adenine, guanine, cytosine and uracil at 1' position or their equivalents; such bases can be used at any position, for example, within the catalytic core of an enzymatic nucleic acid molecule and/or in the substrate-binding regions of the nucleic acid molecule.

The term "nucleoside" as used herein, refers to a heterocyclic nitrogenous base in N-glycosidic linkage with a sugar. Nucleosides are recognized in the art to include natural bases (standard), and modified bases well known in the art. Such bases are generally located at the 1' position of a nucleoside sugar moiety. Nucleosides generally comprise a base and sugar group. The nucleosides can be unmodified or modified at the sugar, and/or base moiety, (also referred to interchangeably as nucleoside analogs, modified nucleosides, non-natural nucleosides, non-standard nucleosides and others). Some of the non-limiting examples of chemically modified and other natural nucleic acid bases that can be introduced into nucleic acids include, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, quesosine, 2-thiouridine, 4-thiouridine, wybutosine, wybutoxosine, 4-acetylcytidine, 5-(carboxyhydroxymethyl)uridine, 5'-carboxymethylaminomethyl-2-thiouridine, 5-carboxymethylaminomethyluridine, beta-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N-6-isopentenyladenosine, beta-D-mannosylqueosine, uridine-5-oxyacetic acid, 2-thiocytidine, threonine derivatives and others. By "modified bases" in this aspect is meant nucleoside bases other than adenine, guanine, cytosine and uracil at 1' position or their equivalents; such bases can be used at any position, for example, within the catalytic core of an enzymatic nucleic acid molecule and/or in the substrate-binding regions of the nucleic acid molecule.

The term "abasic" as used herein, refers to sugar moieties lacking a base or having other chemical groups in place of a base at the 1' position, (see, e.g., International PCT publication No. WO 97/26270).

The term "unmodified nucleoside" as used herein, refers to one of the bases adenine, cytosine, guanine, thymine and uracil joined to the 1' carbon of β-D-ribofuranose.

The term "modified nucleoside" as used herein, refers to any nucleotide base which contains a modification in the chemical structure of an unmodified nucleotide base, sugar and/or phosphate.

The term "oligonucleotide" as used herein, refers to a molecule comprising two or more nucleotides. An oligonucleotide may comprise ribonucleic acids, deoxyribonucleic acids, and combinations and/or chemically modified derivatives thereof. Oligonucleotides may comprise nucleic acids such as enzymatic nucleic acids, antisense nucleic acids, aptamers, decoys, allozymes, ssRNA, double stranded rRNA, siRNA, triplex oligonucleotides and 2,5-A chimeras.

The present invention provides a method that provides a liquid chlorosilane which is readily purified by distillation, comprising a functional moiety which could subsequently be derivatized with a chromophore to produce the desired protecting group. This method involves reacting the intermediate functionalized chlorosilane with a suitably protected nucleoside and purifying the desired product by chromatography in a first step, and then reacting the chromophore with the 5'-silyl protected nucleoside and purifying the desired product by chromatography in a second step, resulting in high yields of 5'-chromophoric-silyl protected nucleoside.

The present invention provides a visible means to qualitatively determine whether RNA synthesis is proceeding properly, as well as enabling a colorimetric assay for the near quantitative determination of coupling efficiency for the 5'-silyl-2'-orthoester RNA synthesis strategy. In addition, the chromophoric-silyl group maintains the advantages of the existing 5'-silyl protecting groups, i.e, rapid fluoride ion deprotection and highly efficient coupling yields; and is introduced onto the 5'-hydroxyl in a manner that maintains the selectivity of current 5'-silyl protecting groups. The 5'-chromophoric-silyl protected phosphoramidite compositions exist as solid foams as opposed to syrupy resins, thereby simplifying manipulations such as weighing and transferring. Additionally, the novel silyl protecting group compositions of the present invention are prepared from materials that are readily available (even in bulk) and of relatively low cost.

The compositions and methods of the present invention are applicable to chemical RNA synthesis, as well as DNA synthesis. In this case, an additional advantage is realized over the current 5'-DMT protecting group chemistry. It is well known that the aggressive acid deprotection conditions for the DMT group can cause a small but significant degree of depurination of the oligonucleotide undergoing synthesis. These sites of depurination result in sites of chain scission during the cleavage and nucleobase deprotection steps, causing a reduction in yield of full length oligonucleotide as well as complicating the crude product mixture. Use of the non-acidic fluoride labile 5'-silyl ether approach avoids this problem, which is particularly important for the synthesis of long oligonucleotides (>100 nucleotides) commonly used, for example, in the preparation of synthetic genes.

It will also be recognized by one of ordinary skill in the art that the invention can be utilized for the protection of non-nucleosidic hydroxyl groups, for example, simple alcohols, polyols, sugars, carbohydrates, steroids, vitamins, and other natural products. The 5'-chromophoric-silyl protecting groups have been designed and optimized to be rapidly labile to fluoride ion under mildly basic conditions. As such, they may be productively used in combination with a variety of other protecting groups, including the more stable silyl ethers such as TBDMS, and selectively deprotected under conditions which leave the group intact. Alternatively, they may be utilized as protecting groups for substrates which are chemically incompatible with more stable silyl ethers. Additionally, the chromophoric-silyl protecting groups of the invention can be used to impart a visible detectability or traceability to substrates that are largely unobservable on their own merits except with special stains or equipment.

The present invention provides compounds of the formula (I) C-Q-O—Si($R_1$)($R_2$)—N. Exemplary embodiments include:

5'-DR(OiPr)-2-silyl-nucleoside phosphoramidites;
5'-DR(Me)$_2$-silyl-nucleoside phosphoramidites; and
5'-DR(OTMS)$_2$-silyl-nucleoside phosphoramidites.

Essentially, the methods described herein comprise reacting an intermediate of formula (II) $L_1$-O—Si($R_1$)($R_2$)—N with an intermediate of the general formula (III) $L_2$-C, wherein $L_1$ is selected from the group consisting of azide, alkyne, alkene, maleimide, nitrile oxide, aldehyde or imine; and $R_1$, $R_2$ and N are as described above for formula (I). The reaction results in the product formula (I) where $L_1$ and $L_2$ react to form Q. Preferably Q is any group resulting in the covalent reaction between $L_1$ and $L_2$. In one preferred embodiment, $L_1$ and $L_2$ are an azide or alkyne, wherein the resulting product Q is a triazole.

Methods of synthesizing the protected nucleosides of the present invention are disclosed herein and others will be apparent to those skilled in the art. Preferred methods include metal-catalyzed 1,3-dipolar cycloaddition, olefin metathesis and the hetero-Diels-Alder family of reactions. These types of reactions are generally known as "click" reactions (see Kolb et al., *Drug Discovery Today* 8, 1128-1137 (2003).) One example of "click" chemistry is the Huisgen 1,3-dipolar cycloaddition of an azide compound with an alkyne compound in the presence a copper (I) salt to yield a 1,2,3-triazole. Other means or methods may be used provided that the groups selected on the intermediate chlorosilane are unreactive toward the chlorosilane itself as well as provide the requisite lability to fluoride ion for rapid deprotection during the oligonucleotide synthesis process. Additionally, the chromophore should be covalently reacted with the 5'-silyl protected nucleoside in such a way that it does not react with the free 3'-hydroxyl (the site of subsequent conversion to the phosphoramidite) as well as not affect any of the already installed protecting groups (e.g., 2'-ACE or nucleobase protecting groups).

FIG. 1 describes the application of the azide-alkyne "click" reaction to the installation of a chromophore into a 5'-silyl-protected nucleoside. In this example, the chromophore component comprises the azide and the 5'-silyl-protecting group comprises the alkyne. Copper (I) catalyzed cycloaddition yields the desired 5'-chromophoric-silyl-protected nucleoside. The 5'-chromophoric-silyl-protected nucleoside is subsequently elaborated into desired phosphoramidite composition under standard conditions well-known to those skilled in the art.

By way of example, a 5'-Disperse Red-silyl protecting group (DR(OiPr)$_2$sil) is depicted below:

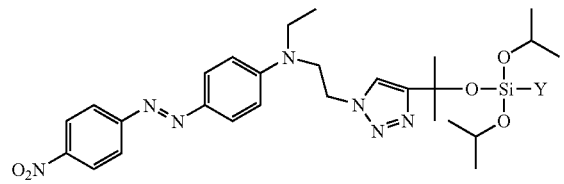

wherein "Y" is the alcohol to be protected; in the case of RNA or DNA synthesis, Y is a umnodified or modified nucleoside or abasic. This novel protecting group is stable to standard phosphoramidite synthesis methods and is also stable to the conventional reagents used in 5'-silyl-2'-orthoester RNA synthesis chemistry. This group is removed conveniently with fluoride ion in as little as 35 seconds to release the Disperse Red (DR) chromophore that can be easily monitored spectrophotometrically to determine the step-wise coupling efficiency of each synthetic cycle. The general structure of the 5'-DR(OiPr)$_2$Sil-2'-ACE-ribonucleotide amidites of the invention is shown below:

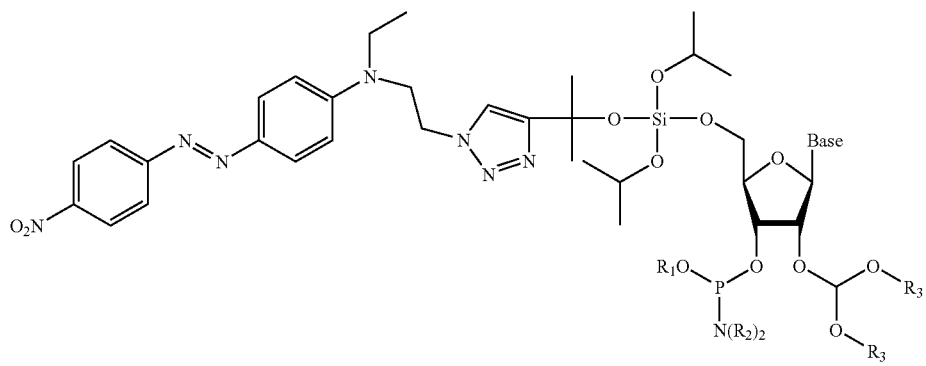

wherein "$R_1$" is an alkyl or aryl group, or heteroatom-substituted alkyl or aryl group, particularly methyl or 2-cyanoethyl, most particularly methyl; "$R_2$" is an alkyl or aryl group, or heteroatom-substituted alkyl or aryl group, particularly isopropyl; "$R_3$" is an alkyl or aryl group, or heteroatom-substituted alkyl or aryl group, particularly 2'-acetoxyethyl; and "Base" represents a common nucleobase, for example but not limited to, adenine, guanine, uracil, thymine or cytosine, or an uncommon nucleobase, for example but not limited to, 2-aminopurine, xanthosine, imidazole, benzimidazole, 5-fluorouracil, 5-bromouracil, 5-iodouracil, 7-deaza-adenine, 7-deazaguanine, pseudouracil, and 6,6-dimethyladenine, suitably protected for use in oligonucleotide synthesis.

Oligonucleotide assembly with 5'-DR(OiPr)$_2$Sil-protected phosphoramidites follows exactly the conditions for 5'-silyl-2'-orthoester RNA synthesis described in the prior art (see generally *Methods in Molecular Biology, Volume 20: Protocols for Oligonucleotides and Analogs* (Agrawal, Ed., Humana Press, 1993); *Oligonucleotides and Analogues: A Practical Approach* (Eckstein, Ed., IRL Press, 1991); *Oligonucleotide Synthesis: A Practical Approach* (Gait, Ed., IRL Press, 1984); Reese, *Tetrahedron Lett.* 22, 1859-1862 (1981); Agrawal U.S. Pat. No. 5,149,798).

Deprotection of the phosphate protecting group, exocyclic amines, cleavage from the support, and the eventual deprotection of the 2'-orthoester group all follow previously reported procedures. As described previously, the colored 5'-deprotection solution may be collected for quantification, or if a visual confirmation that the synthesis is proceeding normally is all that is needed, collection is not necessary. Quantification of the collected chromophore is accomplished by diluting the solution obtained from the synthesis instrument and measuring the absorbance at the appropriate wavelength, which is specific to the particular chromophore used and solution employed for dilution. For example, if the Disperse Red chromophore is diluted with acetonitrile, the $\lambda_{max}$ of the solution is 470 nm; in water it is 490 nm; and in 0.5 M $H_2SO_4$ it is 540 nm.

The coupling efficiency for a particular step is calculated from the ratio of the absorbance of the current coupling step to the absorbance of the previous coupling step. The average stepwise yield for the synthesis of the entire oligonucleotide is calculated by the following equation:

Average Stepwise Yield %=(Absorbance of the last coupling step/Absorbance of the first coupling step)$^{1/n}$×100 wherein "n" is the total number of coupling steps.

The following examples are meant to be illustrative of certain embodiments of the invention only and are not limiting in any way.

EXAMPLES

Example 1

Synthesis of Ancillary Reagents

A. Synthesis of DPMBSiCl:

Diisopropoxydichlorosilane (1): This material is prepared after the manner of Chappelow et al. (*J. Org. Chem.* 1960, 25, 435-459.) 2-Propanol (887 g, 14.8 mol) was added slowly over a period of three hours under an atmosphere of Ar to SiCl$_4$ (1475 g, 8.7 mol) at 0° C. The vented HCl gas from the reaction was neutralized by bubbling through a 25% (w/v) solution of KOH in water. The solution was allowed to react for 3 h whereupon, Ar was bubbled through the solution for 30 min. The solution was then distilled through a 30 cm Hemple column packed with 3 mm glass beads (Pot Temp: 180° C., Vapor Temp: 120° C.). The resulting fractions were analyzed by $^1$H NMR. Fraction A: 411 g (95% Mono: 5% Di); Fraction B: 184 g (22% Mono, 76% Di, 2% Tri); Fraction C: 511 g—27% yield, (95% Di, 5% Tri); and Fraction D: 393 g (50% Di, 50% Tri). Fractions B and D were pooled with other impure cuts from other runs and redistilled at a latter date. $^1$H NMR (CDCl$_3$, 300 mHz) δ Mono: 4.53 (h, J=6.2 Hz, 1 H), 1.31 (d, J=6.2 Hz, 6 H). Di: 4.41 (h, J=6.2 Hz, 2 H), 1.26 (d, J=6.2 Hz, 12 H); Tri: 4.29 (h, J=6.2 Hz, 3 H), 1.21 (d, J=6.2 Hz, 12 H). $^{13}$C NMR (CDCl$_3$, 75.5 mHz) δ Di: 69.27, 24.85.

Diisopropoxy-(2-methyl-3-butyn-2-oxy) chlorosilane (DPMBSiCl): A dry-3-Neck flask was charged with 1 (695 g, 3.2 mol), 500 mL of CH$_2$Cl$_2$ and Et$_3$N (552 g, 5.4 mol). The flask was placed under an atmosphere of Ar, equipped with an overhead stirrer and cooled to 0° C. A solution of 2-Methyl-3-butyn-2-ol (270 g, 3.2 mol) in 1200 mL CH$_2$Cl$_2$ was added slowly to the above solution over 4 h. The reaction was maintained at 0° C. and allowed to slowly warm to 15° C. After stirring for 18 h the salts were filtered away and the light brown solution was concentrated. The resulting oil was filtered into a dry 2 L flask and vacuum distilled (Pot Temp: 63° C., Vacuum: 63 mTorr, Vapor Temp: 40° C.). The resulting fractions were analyzed by $^1$H NMR. Fraction A: 187 g (Product with slight impurity); Fraction B: 467 g—55% yield, (Pure product) $^1$H NMR (CDCl$_3$, 300 mHz) δ 4.33 (h, J=6.2 Hz, 2 H), 2.44 (s, 1 H), 1.60 (s, 6 H), 1.23 (d, J=6.2 Hz, 12 H), $^{13}$C NMR (CDCl$_3$, 75.5 mHz) δ 87.32, 71.30, 69.04, 67.69, 32.13, 25.10.

B. Synthesis of DMMBSiCl:

Dimethyl-(2-methyl-3-butyn-2-oxy) chlorosilane (DMMBSiCl): A dry-3-Neck flask was charged with Dichlordimethylsilane (684 g, 5.3 mol), 1000 mL of CH$_2$Cl$_2$ and Et$_3$N (914 g, 9.01 mol). The flask was placed under an atmosphere of Ar, equipped with an overhead stirrer and cooled to 0° C. A solution of 2-Methyl-3-butyn-2-ol (446 g, 5.3 mol) in 500 mL CH$_2$Cl$_2$ was added slowly to the above solution over 3 h. The reaction was maintained at 0° C. and allowed to slowly warm to 15° C. After stirring for 24 h the salts were filtered away and the dark brown solution was concentrated. The resulting oil was filtered into a dry 2 L flask and fractionally distilled (Pot Temp: 40° C., Vacuum: 7 mBar, Vapor Temp: 26° C.). The early fractions are discarded and the major fraction was kept, (421 g, 2.06 mol, 39%). $^1$H NMR (CDCl$_3$, 300 mHz) δ 2.47 (s, 1 H), 1.56 (s, 6 H), 0.52 (s, 6 H); $^{13}$C NMR (CDCl$_3$, 75.5 mHz) δ 87.76, 72.14, 68.52, 32.62, 4.39.

C. Synthesis of BTMBSiCl:

Bis-trimethylsilyloxy-(2-methyl-3-butyn-2-oxy) chlorosilane (BTMBSiCl): A dry-3-Neck flask was charged with Bis-trimethylsilyloxydichlorosilane (909 g, 3.28 mol), 1000 mL of CH$_2$Cl$_2$ and Et$_3$N (563 g, 5.57 mol). The flask was placed under an atmosphere of Ar, equipped with an overhead stirrer and cooled to 0° C. A solution of 2-Methyl-3-butyn-2-ol (276 g, 3.28 mol) in 740 mL CH$_2$Cl$_2$ was added slowly to the above solution over 5 h. The reaction was maintained at 0° C. and allowed to slowly warm to 15° C. After stirring for 48 h the salts were filtered away and the light brown solution was concentrated. The resulting oil was filtered into a dry 2 L flask and fractionally distilled (Pot Temp: 65° C., Vacuum: 86 mTorr, Vapor Temp: 35° C.). The early fractions are discarded and the major fraction was kept, (521 g, 1.6 mol, 49%). $^1$H NMR (CDCl$_3$, 300 mHz) δ 2.41 (s, 1 H), 1.57 (s, 6 H), 0.15 (s, 18 H); $^{13}$C NMR (CDCl$_3$, 75.5 mHz) δ 87.41, 71.27, 68.62, 32.19, 1.59.

D. Synthesis of DR-N$_3$:

N-Ethyl-N-(2-Azidoethyl)aniline (2): N-Ethyl-(2-anilino)ethanol (91.5 g, 554 mmol) was dissolved in 1400 mL of CH$_2$Cl$_2$ and Et$_3$N (192.4 mL, 1385 mmol) was added. The solution was cooled to 0° C. and Methanesulfanonyl chloride (51.8 mL, 665 mmol) was slowly added over 30 min. After 0.5 h, the reaction was diluted with 500 mL CH$_2$Cl$_2$ and washed successively with 500 mL of 2% HCl (×2), then 500 mL water, and 500 mL of saturated NaCl. The organic phase was passed over a pad of Na$_2$SO$_4$, and evaporated to light brown-colored oil (135 g, 554 mmol, 100%). $^1$H NMR (CDCl$_3$, 300 mHz) δ 7.25-7.19 (m, 2 H), 6.73-6.68 (m, 3 H), 4.33 (t, J=6.2

Hz, 2 H), 3.65 (t, J=6.2 Hz, 1 H), 3.41 (q, J=7.1 Hz, 2 H), 2.96 (s, 3 H), 1.16 (t, J=7.1 Hz, 3 H).

Sodium Azide (17.4 g, 267 mmol) was added to the above material and diluted with 600 mL of DMSO. The flask was heated to 70° C. and stirred for 1.5 h and cooled to room temperature. The solution was diluted with 1500 mL of water and extracted with 600 mL of $Et_2O$ three times. The combined organic phase was washed three times with 800 mL of water and then once with 800 mL of saturated NaCl. The organic phase was passed over $Na_2SO_4$ and evaporated to leave 2 as a thick oil (101 g, 531 mmol, 96%.) $^1$H NMR ($CDCl_3$, 300 mHz) δ 7.31-7.22 (m, 2 H), 6.77-6.69 (m, 3 H), 3.56-3.42 (m, 6 H), 1.19 (t, J=10.6 Hz, 3 H).

N-Ethyl-N-(2-Azidoethyl)-4-(4-nitrophenylazo)aniline (DR-$N_3$): In a 2 L flask, 100 mL of concentrated $H_2SO_4$ was cooled to 0° C. and $NaNO_2$ (40.7 g, 590 mmol) was added portion wise over a period of 15 min. The light-purple solution was stirred a further 10 min and diluted with 1000 mL of AcOH and 300 mL of PrOH. The reaction was maintained at 0° C. and 4-Nitroaniline (81.5 g, 590 mmol) was added over a period of 15 min. The yellowish-brown solution was stirred for 2 h and then added to the solution below.

A 5 L 3-neck flask equipped with an overhead stirrer, was charged with 2 (112.3 g, 590 mmol), 180 g of NaOAc, 800 mL of AcOH, and 800 mL of $H_2O$ and cooled to 0° C. The above diazonium species was transferred to a separatory funnel and slowly added over 20 min to the azide solution. This generated an immediate red color that precipitated out of solution. The solution was then diluted with 1 L of 20% (w/v) solution of NaOAc in water and stirred for an additional 3 h at 0° C. The red paste was filtered and washed with 8 L of $H_2O$. (206.5 g). This material was dissolved in 1200 mL of $CH_2Cl_2$ and washed 5 times with 800 mL water. The combined aqueous washes were back extracted once with 300 mL $CH_2Cl_2$ and the combined organic phase was washed with 1000 mL of saturated NaCl. The organic phase was dried over $Na_2SO_4$, filtered, and dried to leave a sheeny-red solid which was recrystallized in five portions from 900 mL of hot EtOH. Filtration of solids and washing with cold EtOH leaves a dull red solid that was dried overnight in a vacuum desiccator (150.8 g, 75%). $^1$H NMR ($CDCl_3$, 300 mHz) δ 8.30 (d, J=14.1 Hz, 2 H), 7.91 (d, J=9.5 Hz, 2 H), 7.84 (d, J=7.8 Hz, 2 H), 6.72 (d, J=10.1 Hz, 2 H), 3.68-3.46 (m, 6 H), 1.25 (t, J=7.1 Hz, 3 H); $^{13}$C NMR ($CD_3CN$, 75.5 Hz) δ 156.90, 150.60, 147.32, 143.86, 126.27, 124.62, 122.65, 111.46, 49.49, 48.93, 45.83, 12.26.

E. Synthesis of DB-$N_3$:

N-Ethyl-N-(2-Azidoethyl)-4-(5-nitro-2-thiazole-azo) aniline: A solution of nitrosulfuric acid (4.1 mL, 20.54 mmol) was slowly added to 70 mL of a solution of 6:1 AcOH/PrOH at 0° C. After stirring for 30 min 2-amino-5-nitrothiazole (2.60 g, 17.86 mmol) was added in small portions over 30 min. The solution was stirred for an additional 50 min and slowly added to the solution described below.

In a separate flask, 2 (4.93 g, 25.9 mmol) was diluted with 120 mL water, 5 mL AcOH, and 1 mL of concentrated HCl. The solution was cooled to 0° C. and the diazonium species from above was added over 15 min to generate an immediate dark blue color. The reaction was warmed to room temperature and stirred for 1 h. The reaction was neutralized with 50 mL of 10 M NaOH on an ice bath. The solution was filtered and washed with water to leave a black tar-like substance that was dissolved in acetone and crystallized by the addition of water. Filtration leaves a black solid that was further washed with $Et_2O$. Drying of the powder leaves 2.49 g (40%) $^1$H NMR ($CDCl_3$, 300 mHz) δ 8.60 (s, 1 H), 7.95 (d, J=9.3 Hz, 2 H), 6.78 (d, J=9.3 Hz, 2 H), 3.68-3.57 (m, 6 H), 1.29 (t, J=7.1 Hz, 3 H).

F. Synthesis of AR-$N_3$:

1-[(2-Azidoethyl)amino]anthracene-9,10-dione (AR-$N_3$): Compound 3 (12.88 g, 48.2 mmol) was prepared as described by Krapch, A. P., and Shaw, K. J. (*J. Org Chem.* 1983, 48, 3341-3343) and dissolved in 500 mL of $CH_2Cl_2$ and $Et_3N$ (12.20 g, 120.2 mmol). The solution was cooled to 0° C. and methanesulfonyl chloride (6.63 g, 57.84 mmol was added dropwise. After 2 h the reaction was diluted with 500 mL of $CH_2Cl_2$ and washed with 10% HCl. The organic layer was washed with saturated NaCl, and dried over $Na_2SO_4$. The red solution was evaporated to dryness leaving a red solid (16.0 g, 96%). $^1$H NMR ($CDCl_3$, 300 mHz) δ 9.93 (b, 1 H), 8.32-8.22 (m, 2 H), 7.80-7.50 (m, 4 H), 7.08 (d, J=8.4 Hz, 1 H), 4.48 (t, J=5.6 Hz, 2 H), 3.75 (q, J=5.7 Hz, 2 H), 3.07 (s, 3 H).

The above material was mixed with $NaN_3$ (3.60 g, 55.6 mmol) and suspended in 150 mL of 95% EtOH. The mixture was heated to 80° C. for 18 h and evaporated to dryness. The resulting red paste was dissolved in $CH_2Cl_2$ and washed with water. The aqueous phase was back extracted once with $CH_2Cl_2$ and the combined organic phase was washed with saturated NaCl. The organics were dried over $Na_2SO_4$ and evaporated to dryness. The red solid was crystallized from $CH_2Cl_2$ to yield 9.13 g of red needles (65%). $^1$H NMR ($CDCl_3$, 300 mHz) δ 9.95 (b, 1 H), 8.30-8.21 (m, 2 H), 7.78-7.54 (m, 4 H), 7.07 (d, J=7.4 Hz, 1 H), 3.66-3.54 (m, 4 H); $^{13}$C NMR ($CDCl_3$, 75.5 Hz) δ 185.44, 183.71, 151.28, 135.56, 135.40, 134.95, 134.94, 134.15, 133.28, 133.11, 132.78, 126.97, 117.45, 116.41, 113.76, 50.52, 42.15.

G. Synthesis of MP Orthoformate:

Tris-(2-Butyn-1-oxy)-orthoformate (MP-orthoformate): This material was prepared in a similar fashion as described by Scaringe (see U.S. Pat. No. 5,889,136). A 3 L round bottom flask was charged with 2-Butyn-1-ol (334 g, 4.77 mol), p-toluenesulfonic acid monohydrate (6.0 g, 32 mmol), and triethyl orthoformate (235.6 g, 1.59 mol) was diluted with 800 mL of dioxane. The reaction was gently heated under vacuum (75 mBar) to sustain a constant drip rate of 1-2 drops/sec. After 18 h, the flask was recharged with 800 mL of dioxane and 2-Butyn-1-ol (23.2 g, 0.33 mol) and the heating and vacuum were resumed. After 8 h, the volatile solvents were removed under "full-vacuum" (6 mBar) and the reaction was stopped by the addition of 20 mL of $Et_3N$. The product was fractionally distilled (Pot Temp: 175° C., Vacuum: 300 mTorr, Vapor Temp: 105° C.) to give 264 g, 75%) as a colorless oil that would solidify upon sitting at −20° C. $^1$H NMR ($CDCl_3$, 300 mHz) δ 5.51 (s, 1 H), 4.18 (s, 6 H), 1.79 (s, 9 H); $^{13}$C NMR ($CDCl_3$, 75.5 mHz) δ 110.20, 82.62, 74.41, 52.89, 3.68.

Example 2

Synthesis of 5'-DR(OiPr)$_2$Silyl Amidites

A. 5'-DR(OiPr)$_2$-Silyl-rA(NiBu) Amidite (4d):

Silylation of 4a: Diisopropylamine (18.2 g, 180.0 mmol) was added to a solution of 4a (50.0 g, 90.0 mmol) in 1 L of $CH_2Cl_2$ and the solution was cooled to 0° C. In a separate flask DPMBSiCl (31.0 g, 117.0 mmol) was diluted in 240 mL of $CH_2Cl_2$. Diisopropylamine (14.2 g, 140.4 mmol) was added to the silylating solution and the solution was allowed to stir for 2 min before being added dropwise to the nucleoside solution. The addition was completed within 30 min and the reaction was allowed to slowly warm to room temperature overnight. The following morning TLC analysis showed consumption of starting material. The reaction was stopped by addition of 30 mL of MeOH and evaporated to dryness. The crude material was purified by flash chromatography on 1.5 L silica gel using a gradient of ethyl acetate and acetone in hexanes [0:2:8 (v/v/v) to 4:2:4 (v/v/v] containing 0.1% (v/v) Et$_3$N. Product fractions were pooled and evaporated to afford 4b as a colorless oil. The yield was 62.5 g (89%). $^1$H NMR (CD$_3$CN, 300 mHz) δ 8.79 (b, 1 H), 8.61 (s, 1 H), 8.43 (s, 1 H), 6.19 (d, J=5.6 Hz, 1 H), 5.37 (s, 1 H), 4.93 (t, J=5.3 Hz, 1 H), 4.48-4.43 (m, 1 H), 4.31-4.21 (m, 2 H), 4.17-3.94 (m, 7 H), 3.72-3.59 (m, 3 H), 3.52-3.44 (m, 2 H), 3.17-3.08 (m, 1 H), 2.75 (s, 1 H), 1.96 (s, 1 H), 1.95 (s, 1 H), 1.56 (s, 6H), 1.22-1.16 (m, 18 H); $^{13}$C NMR (CD$_3$CN, 75.5 mHz) δ 177.17, 171.90, 153.43, 153.09, 150.98, 143.62, 124.48, 113.92, 89.37, 87.84, 86.49, 77.31, 72.52, 71.80, 68.82, 67.58, 64.41, 64.27, 64.19, 64.09, 61.35, 36.71, 32.91, 31.31, 26.08, 21.45, 19.97, 14.93; ESI-TOF MS (M+H$^+$) calculated 784.3437, observed 784.3417.

Dye conjugation of 4b with DR-N$_3$: Copper Iodide (1.57 g, 8.0 mmol) was added to a solution of 4b (62.5 g, 80.0 mmol), DR-N$_3$ (35.3 g, 104.0 mmol), and iPr$_2$NEt (10.34 g, 80.0 mmol) in 1.6 L of Toluene. The solution was sonicated for 1 min and then stirred at room temperature for 3 h. The solution was then partitioned between ethyl acetate and saturated NaCl. The aqueous phase was back extracted once with ethyl acetate to remove all red color from the water layer. The organic phases were combined and concentrated. The crude material was purified by flash chromatography on 1.8 L silica gel using a gradient of ethyl acetate and acetone in hexanes [2:2:6 (v/v/v) to 6:2:2 (v/v/v)] containing 0.1% (v/v) Et$_3$N. Product fractions were pooled and evaporated to afford 4c as a red foam. The yield was 69.0 g (77%). $^1$H NMR (CD$_3$CN, 300 mHz) δ 8.75 (b, 1 H), 8.57 (s, 1 H), 8.28 (s, 1 H), 8.30 (d, J=10.6 Hz, 2 H), 7.88 (d, J=9.7 Hz, 2 H), 7.76 (d, J=10.6 Hz, 2 H), 7.64, s, 1 H), 6.6 d, J=9.3 Hz, 2 H), 6.16 (d, J=5.2 Hz, 1 H), 5.39 (s, 1 H), 4.88 (t, J=5.1 Hz, 1 H), 4.56 (t, J=6.0 Hz, 2 H), 4.42 (q, J=9.4 Hz, 1 H), 4.22-4.08 (m, 3 H), 4.04-3.94 (m, 5 H), 3.90-3.84 (m, 3 H), 3.67-3.60 (m, 4 H), 3.54-3.47 (m, 1 H), 3.30 (q, J=14.2 Hz, 2 H), 3.15-3.06 (m, 1 H), 1.94 (s, 3 H), 1.93 (s, 3 H), 1.61 (s, 6 H), 1.19 (d, J=8.6 Hz, 6 H), 1.10 (d, J=6.1 Hz, 12 H), 1.07 (t, J=7.1 Hz, 3 H); $^{13}$C NMR (CD$_3$CN, 75.5 mHz) δ 177.14, 171.87, 157.94, 156.52, 153.39, 152.96, 152.62, 150.87, 148.84, 144.87, 143.48, 127.27, 126.10, 123.78, 122.83, 113.94, 112.81, 87.95, 86.25, 77.43, 73.40, 71.48, 67.45, 64.36, 64.19, 64.34, 64.19, 64.14, 64.10, 51.38, 48.81, 46.41, 36.68, 31.47, 34.41, 26.07, 21.43, 21.41, 19.97, 12.69. ESI-TOF MS (M+Na$^+$) calculated 1145.4694, observed 1145.4696.

Phosphitylation of 4c: Bis(diisopropylamino) methoxy phosphine (24.0 g, 91.5 mmol) was dissolved in 200 mL of CH$_2$Cl$_2$ and a 0.5 M solution of 5-ethylthio-1-H-tetrazole in anhydrous acetonitrile (61.4 mL, 30.7 mmol) was added. Diisopropylamine (6.1 g, 61.4 mmol) was then added and the phosphine solution was allowed to stir for 5 min at ambient temperature. In a separate flask, 4c (69.0 g, 61.4 mmol) and diisopropylamine (6.1 g, 61.4 mmol) were dissolved in 300 mL of CH$_2$Cl$_2$. The activated phosphine solution was added into the nucleoside solution and the reaction was stirred at room temperature. After 16 h the reaction was quenched with 50 mL of absolute ethanol and concentrated to dryness. The resulting paste was purified by flash chromatography on 2 L of silica gel using a mixture of CH$_2$Cl$_2$ in hexanes (5:95 (v/v) containing 2% (v/v) Et$_3$N followed by acetone in hexanes (2:8 (v/v) to 4:6 (v/v) containing 0.5% (v/v) Et$_3$N. Product fractions were pooled and evaporated to afford 4d as a red foam. The yield was 67.5 g (86%). $^1$H NMR (CD$_3$CN, 300 mHz) δ 8.67 (s, 1 H), 8.55 (s, 1 H), 8.38 and 8.37 (each as s, 1H), 8.32 (d, J=8.9 Hz, 2 H), 7.89 (d, J=8.9 Hz, 2 H), 7.76 (d, J=8.3 Hz, 2 H), 7.63 and 7.62 (each as s, 1 H), 6.65 (d, J=9.2 Hz, 2 H), 6.19-6.15 (m, 1 H), 5.37 and 5.30 (each as s, 1 H), 4.99-4.92 (m, 1 H), 4.67-4.53 (m, 3 H), 4.26-4.18 (m, 3 H), 4.03-3.84 (m, 8 H), 3.72-3.50 (m, 5 H), 3.46-3.26 (m, 6 H), 3.14-3.05 (m, 1 H), 1.96-1.90 (m, 6 H), 1.62 and 1.60 (each as s, 6 H), 1.22-1.04 (m, 33 H); $^{31}$P NMR (CD$_3$CN, 121.5 Hz) δ 150.99, 150.34; ESI-TOF MS (M+Na$^+$) calculated 1306.5664, observed 1306.5657.

B. 5'-DR(OiPr)$_2$-Silyl-rG(NiBu) Amidite (5d):

Silylation of 5a: Following similar procedural details described for the silylation of 4a in Example 2A, 5b was produced in a 78% yield from 5a (50.0 g, 87.5 mmol). $^1$H NMR (CD$_3$CN, 300 Hz) δ 9.54 (b, 1 H), 8.10 (s, 1 H), 5.96 (d, J=5.7 Hz, 1 H), 5.36 (s, 1 H), 4.73 (t, J=5.4 Hz, 1 H), 4.42 (q, J=8.6 Hz, 1 H), 4.32-4.24 (m, 2 H), 4.12-3.93 (m, 7 H), 3.72-3.62 (m, 3 H), 3.56 (m, 1 H), 3.43-3.41 (m, 1 H), 2.75 (s, 1 H), 2.70 (p, J=6.8 Hz, 1 H), 1.98 (s, 3 H), 1.97 (s, 3 H), 1.56 (s, 6 H), 1.21-1.17 (m, 18 H); $^{13}$C NMR (CD$_3$CN, 75.5 Hz) δ 181.44, 172.04, 156.81, 150.22, 149.69, 139.05, 122.16, 113.85, 89.36, 87.17, 86.48, 77.81, 72.52, 71.91, 68.83, 67.41, 64.64, 64.44, 64.26, 64.21, 64.16, 37.06, 32.92, 26.09, 21.46, 19.68, 19.61; ESI-TOF MS (M+H$^+$) calculated 800.3386, observed 800.3392.

Dye conjugation of 5b with DR-N$_3$: Following similar procedural details described for the dye conjugation of 4b in Example 2A, 5c was produced in a 71% yield from 5b (54.4 g, 68.0 mmol). $^1$H NMR (CD$_3$CN, 300 Hz) δ 9.61 (b, 1 H), 8.31 (d, J=7.1 Hz, 2 H), 8.04 (s, 1 H), 7.88 (d, J=7.1 Hz, 2 H), 7.77 (d, J=9.2 Hz, 2 H), 7.59 (s, 1 H), 6.64 (d, J=9.2 Hz, 2 H), 5.92 (d, J=5.2 Hz, 1 H), 5.42 (s, 1 H), 4.70 (t, J=5.1 Hz, 1 H), 4.57 (t, J=6.0 Hz, 2 H), 4.40 (q, J=4.7 Hz, 1 H), 4.25-4.11 (m, 2 H), 4.09-3.99 (m, 5 H), 3.94-3.82 (m, 4 H), 3.73-3.52 (m, 5 H), 3.34 (q, J=6.2 Hz, 2 H), 3.08 (q, J=7.3 Hz, 1 H), 2.69 (p, J=6.8 Hz, 1 H), 1.96 (s, 3 H), 1.94 (s, 3 H), 1.57 (s, 6 H), 1.18-1.06 (m, 21 H); $^{13}$C NMR (CD$_3$CN, 75.5 Hz) δ 181.51, 171.97, 157.85, 156.82, 156.51, 152.58, 150.10, 149.62, 148.66, 144.83, 144.83, 129.18, 127.31, 126.03, 123.78, 122.91, 122.10, 112.61, 112.78, 87.46, 86.20, 77.86, 73.42, 71.46, 67.46, 64.34, 64.28, 64.20, 63.99, 51.46, 48.83, 47.58, 46.51, 36.92, 31.56, 31.50, 26.15, 19.78, 19.73, 12.83, 9.57; ESI-TOF MS (M+Na$^+$) calculated 1161.4643, observed 1161.4640.

Phosphitylation of 5c: Following similar procedural details described for the phosphitylation of 4c in Example 2A, 5d was produced in a 81% yield from 5c (50.4 g, 44.2 mmol). $^1$H NMR (CD$_3$CN, 300 Hz) δ 9.61 (b, 1 H), 8.32 (d, J=9.7 Hz, 2 H), 8.13 and 8.12 (each as s, 1 H), 7.88 (d, J=9.7 Hz, 2 H), 7.78 (d, J=9.1 Hz, 2 H), 7.72 and 7.67 (each as s, 1 H), 6.68 (d, J=9.2 Hz, 2 H), 5.97 (t, J=6.7 Hz, 1 H), 5.43 and 5.38 (each as s, 1 H), 4.78-4.72 (m, 1 H), 4.62-4.46 (m, 3 H), 4.30-4.25 (m, 3 H), 4.06-3.90 (m, 7 H), 3.87-3.82 (m, 5 H), 3.73-3.44 (m, 4 H), 3.40-3.38 (m, 4 H), 2.78-2.64 (m, 1 H), 1.98 and 1.97 (each as s, 3 H), 1.95 and 1.94 (s, 3 H), 1.67 and 1.65 (each as s, 6 H), 1.23-1.03 (m, 33 H). $^{31}$P NMR (CD$_3$CN, 121.5 Hz) δ 151.98, 150.88; ESI-TOF MS (M+Na$^+$) calculated 1322.5613; observed 1322.5626.

C. 5'-DR(OiPr)$_2$-Silyl-rC(NAc) Amidite (6d):

Silylation of 6a: Following similar procedural details described for the silylation of 4a in Example 2A, 6b was produced in an 86% yield from 6a (50.0 g, 99.4 mmol). $^1$H NMR (CD$_3$CN, 300 mHz) δ 9.01 (b, 1 H), 8.36 (d, J=7.5 Hz, 1 H), 7.33 (d, J=7.5 Hz, 1 H), 5.93 (d, J=2.1 Hz, 1 H), 5.67 (s, 1 H), 4.34-4.20 (m, 3 H), 4.18-4.10 (m, 5 H), 4.07-3.96 (m, 3 H), 3.84-3.75 (m, 4 H), 3.33-3.31 (m, 1 H), 2.75 (s, 1 H), 2.13 (s, 3 H), 2.01 (s, 3 H), 1.99 (s, 3 H), 1.57 (s, 6 H), 1.21 (d, J=6.1 Hz, 12 H); $^{13}$C NMR (CD$_3$CN, 75.5 mHz) δ 172.42, 171.99, 164.21, 156.51, 146.40, 113.88, 97.25, 90.43, 89.28, 85.11, 78.95, 72.68, 69.32, 68.84, 67.64, 65.20, 64.46, 64.37, 63.91, 63.76, 62.79, 61.36, 32.99, 26.15, 25.51, 21.51, 14.99; ESI-TOF MS (M+Na$^+$) calculated 754.2825, observed 754.2839.

Dye conjugation of 6b with DR-N$_3$: Following similar procedural details described for the dye conjugation of 4b in Example 2A, 6c was produced in an 80% yield from 6b (59.7 g, 68.0 mmol). $^1$H NMR (CD$_3$CN, 300 mHz) δ 8.85 (b, 1 H), 8.31 (d, J=9.0 Hz, 2 H), 8.28 (d, J=7.6 Hz, 1 H), 7.89 (d, J=9.0 Hz, 2 H), 7.79 (d, J=8.9 Hz, 2 H), 7.63 (s, 1 H), 7.24 (d, J=7.5 Hz, 1 H), 6.69 (d, J=9.2 Hz, 2 H), 5.88 (m, 1 H), 5.69 (s, 1 H), 4.57 (t, J=6.0 Hz, 2 H), 4.28-4.12 (m. 8 H), 4.07-3.99 (m, 2 H), 3.91-3.68 (m, 8 H), 3.34 (q, J=7.0 Hz, 2 H), 2.10 (s, 3 H), 2.00 (s, 3 H), 1.98 (s, 3 H), 1.62 (s, 6 H), 1.14 (d, J=6.1 Hz, 12 H), 1.10 (t, J=7.1 Hz, 3 H); $^{13}$C NMR (CD$_3$CN, 75.5 mHz) δ 171.17, 171.95, 163.94, 157.93, 156.40, 156.29, 152.65, 148.94, 146.11, 144.89, 127.30, 127.11, 123.78, 122.71, 113.83, 112.83, 96.91, 90.50, 84.91, 78.90, 73.34, 69.03, 67.50, 64.45, 64.36, 63.73, 62.53, 51.36, 48.81, 46.42, 31.46, 31.41, 31.29, 26.11, 25.43, 21.45, 12.72; ESI-TOF MS (M+Na$^+$) calculated 1093.4269, observed 1093.4259.

Phosphitylation of 6c: Following similar procedural details described for the phosphitylation of 4c in Example 2A, 6d was produced in an 80% yield from 6c (73.6 g, 69.0 mmol). $^1$H NMR (CD$_3$CN, 300 mHz) δ 8.92 (s, 1 H), 8.34-8.27 (m, 3 H), 7.88 (d, J=10.2 Hz, 2 H), 7.78 (d, J=9.4 Hz, 2 H), 7.60 and 7.58 (each as s, 1 H), 7.28-7.14 (m, 2 H), 6.67 (d, J=9.7 Hz, 2 H), 5.97-5.92 (m, 1 H), 5.66 and 5.60 (each as s, 1 H), 4.60-4.55 (m, 2 H), 4.36-4.29 (m, 2 H), 4.24-4.01 (m, 7 H), 3.94-3.84 (m, 3 H), 3.81-3.61 (m, 4 H), 3.61-3.50 (m, 2 H), 3.37-3.27 (m, 5 H), 2.10 (s, 3 H), 1.99-1.97 (m, 6 H), 1.64 and 1.62 (each as s, 6 H), 1.19-1.07 (m, 27 H); $^{31}$P NMR (CD$_3$CN, 121.5 Hz)δ; 151.36, 150.55. ESI-TOF MS (M+Na$^+$) calculated 1254.5238, observed 1254.5253.

D. 5'DR(OiPr)$_2$-Silyl-rU Amidite (7d):

Silylation of 7a: Following similar procedural details described for the silylation of 4a in Example 2A, 7b was produced in an 80% yield from 7a (28.2 g, 60.9 mmol). $^1$H NMR (CD$_3$CN, 300 mHz) δ 9.12 (s, 1 H), 7.78 (d, J=8.1 Hz, 1 H), 5.95 (d, J=5.2 Hz, 1 H), 5.61 (d, J=8.1 Hz, 1 H), 5.44 (s, 1 H), 4.34-3.92 (m, 12 H), 3.82-3.66 (m, 4 H), 2.76 (s, 1 H), 2.01 (s, 3 H), 2.00 (s, 3 H), 1.58 (s, 6 H), 1.20 (d, J=6.1 Hz, 12 H); $^{13}$C NMR (CD$_3$CN, 75.5 mHz) δ 172.00, 164.53, 152.07, 141.81, 113.80, 103.38, 89.34, 88.06, 85.84, 77.26, 72.56, 71.02, 68.87, 67.65, 64.32, 64.27, 64.05, 61.36, 32.95, 32.93, 26.11, 21.48, 14.93; ESI-TOF MS (M+Et$_3$NH$^+$) calculated 792.3950, observed 792.3963.

Dye conjugation of 7b with DR-N$_3$: Following similar procedural details described for the dye conjugation of 4b in Example 2A and with the exception of the use of 3 equivalents of DRN$_3$, 7c was produced in a 70% yield from 7b (27.4 g, 39.6 mmol). $^1$H NMR (CD$_3$CN, 300 mHz) δ 9.22 (b, 1 H), 8.30 (d, J=7.1 Hz, 2 H), 7.89 (d, J=9.1 Hz, 2 H), 7.82 (d, J=10.3 Hz, 2 H), 7.73 (d, J=8.2 Hz, 1 H), 7.62 (s, 1 H), 6.70 (d, J=9.3 Hz, 2 H), 5.90 (d, J=4.8 Hz, 1 H), 5.54 (d, J=8.1 Hz, 1 H), 5.47 (s, 1 H), 4.57 (t, J=6.0 Hz, 2 H), 4.32 (t, J=5.0 Hz, 1 H), 4.22-4.00 (m, 7 H), 3.96-3.78 (m, 5 H), 3.74-3.56 (m, 5 H), 3.34 (q, J=14.1 Hz, 2 H), 1.99 (s, 3 H), 1.97 (s, 3 H), 1.62 (s, 6 H), 1.14-1.09 (m, 15 H); $^{13}$C NMR (CD$_3$CN, 75.5 Hz) δ 171.94, 164.53, 157.93, 156.45, 152.63, 151.96, 148.84, 144.90, 141.68, 127.32, 126.12, 123.80, 122.73, 113.78, 112.83, 103.19, 88.29, 85.59, 77.52, 73.39, 70.65, 67.50, 64.27, 64.16, 64.14, 63.69, 51.38, 48.81, 46.43, 31.45, 26.13, 21.47, 12.74; ESI-TOF MS (M+Na$^+$) calculated 1052.4003, observed 1052.4000.

Phosphitylation of 7c: Following similar procedural details described for the phosphitylation of 4c in Example 2A, 7d was produced in an 80% yield from 7c (73.6 g, 69.0 mmol). $^1$H NMR (CD$_3$CN, 300 mHz) δ 9.25 (b, 1 H), 8.30 (d, J=9.0 Hz, 2 H), 7.88 (d, J=9.0 Hz, 2 H), 7.80-7.72 (m, 3 H), 7.60 and 7.58 (each as s, 1 H), 6.68 (d, J=9.1 Hz, 2 H), 5.98-5.94 (m, 1 H), 5.58-5.54 (m, 1 H), 5.45 and 5.39 (each as s, 1 H), 4.60-4.56 (m, 2 H), 4.38-4.32 (m, 2 H), 4.23-4.04 (m, 7 H), 3.94-3.55 (m, 10 H), 3.38-3.28 (m, 5 H), 1.98 and 1.97 (each as s, 6H), 1.63 and 1.62 (each as s, 6 H), 1.18-1.08 (m, 27 H); $^{31}$P NMR (CD$_3$CN, 121.5 Hz). δ 151.03, 150.81; ESI-TOF MS (M+Na$^+$) calculated 1213.4973, observed 1213.4984.

E. 5'-DR(OiPr)$_2$-Silyl-2'-OMe-A(NiBu) Amidite (8d):

Silylation of 8a: Following similar procedural details described for the silylation of 4a in Example 2A, 8b was produced in an 85% yield from 8a (17.5 g, 50.0 mmol). $^1$H NMR (CDCl$_3$, 300 mHz) δ 8.70 (s, 1 H), 8.50 (s, 1 H), 8.37 (b, 1 H), 6.25 (d, J=4.4 Hz, 1 H), 4.51 (d, J=4.7 Hz, 1 H), 4.34-4.24 (m, 3 H), 4.21-4.18 (m, 1 H), 4.14 (dd, J=11.8 Hz, J=2.8 Hz, 1 H), 4.04 (dd, J=11.8 Hz, J=2.4 Hz, 1 H), 3.50 (s, 2 H), 3.47 (d, J=5.4 Hz, 1 H), 3.28 (p, J=6.4 Hz, 1 H), 2.74 (d, J=5.0 Hz, 1 H), 2.43 (s, 1 H), 1.59 (s, 6 H), 1.29 (d, J=6.8 Hz, 6 H), 1.22 (d, J=6.1 Hz, 12 H); $^{13}$C NMR (CD$_3$CN, 75.5 mHz) δ 177.35, 153.46, 151.00, 143.40, 124.56, 89.32, 87.55, 86.49, 84.91, 72.58, 70.66, 68.84, 67.60, 64.27, 59.52, 36.73, 32.96, 26.10, 20.02.

Dye conjugation of 8b with DR-N$_3$: Following similar procedural details described for the dye conjugation of 4b in Example 2A, 8c was produced in a 79% yield from 8b (22.9 g, 39.5 mmol). $^1$H NMR (CDCl$_3$, 300 mHz) δ 8.64 (s, 1 H), 8.38 (s, 2 H), 8.29 (d, J=9.0 Hz, 2 H), 7.88 (d, J=9.0 Hz, 2 H), 7.82 (d, J=9.1 Hz, 2 H), 7.43 (s, 1 H), 6.64 (d, J=9.2 Hz, 2 H), 6.17 (d, J=3.4 Hz, 1 H), 4.52 (t, J=6.2 Hz, 2 H), 4.45 (q, J=5.6 Hz, 1 H), 4.24-4.15 (m, 3 H), 4.11-4.02 (m, 2 H), 3.97-3.86 (m, 3 H), 3.52 (s, 3 H), 3.30-3.22 (m, 4 H), 1.67 (s, 6 H), 1.26 (d, J=6.8 Hz, 6 H), 1.14 (d, J=6.0 Hz, 12 H), 1.08 (t, J=7.1 Hz, 3H); $^{13}$C NMR (CDCl$_3$, 75.5 mHz) δ 176.44, 156.74, 156.10, 152.75, 151.05, 150.62, 149.32, 147.81, 144.27, 141.44, 126.43, 124.89, 122.93, 122.52, 121.20, 111.55, 86.69, 84.98, 84.25, 72.63, 69.06, 66.61, 62.26, 59.01, 50.72, 47.74, 46.01, 36.19, 30.95, 30.78, 25.57, 25.53, 19.38, 12.34.

Phosphitylation of 8c: Following similar procedural details described for the phosphitylation of 4c in Example 2A, 8d was produced in a 92% yield from 8c (28.6 g, 31.1 mmol). $^1$H NMR (CD$_3$CN, 300 mHz) δ 8.67 (b, 1 H), 8.56 (s, 1 H), 8.38 (s, 1 H), 8.31 (d, J=9.0 Hz, 2 H), 7.89 (d, J=9.0 Hz, 2 H), 7.76 (d, J=9.2 Hz, 2 H), 7.65 and 7.63 (each as s, 1 H), 6.66 (d, J=9.2 Hz, 2 H), 6.09 (t, J=5.1 Hz, 1 H), 4.67-4.53 (m, 3 H), 4.43 (q, J=5.6 Hz, 1 H), 4.25-4.13 (m, 3 H), 3.98 (dd, J=11.6 Hz, J=3.4 Hz, 1 H), 3.87-3.83 (m, 3 H), 3.69-3.57 (m, 2 H), 3.40 and 3.38 (each as d, J=13.1 Hz, 3 H), 3.33-3.25 (m, 5 H), 3.09 (p, J=6.8 Hz, 1 H), 1.62 and 1.61 (each as s, 6H), 1.21-1.11 (m, 24 H), 1.07 and 1.06 (each as t, J=7.0 Hz, 3 H); $^{31}$P NMR (CD$_3$CN, 121.5 mHz) δ 151.22, 149.97.

E. 5'-DR(OiPr)$_2$-Silyl-2'-OMe-G(NiBu) Amidite (9d):

Silylation of (9a): Following similar procedural details described for the silylation of 4a in Example 2A, 9b was produced in a 67% yield from 9a (18.4 g, 50.0 mmol). $^1$H NMR (CDCl$_3$, 300 mHz) δ 9.44 (b, 1 H), 8.16 (s, 1 H), 5.91 (d, J=5.7 Hz, 1 H), 4.49-4.44 (m, 1 H), 4.31-4.21 (m, 3 H), 4.22-4.15 (m, 1 H), 4.05-3.95 (m, 2 H), 3.33 (s, 3 H), 3.07 (d, J=3.9 Hz, 1 H), 2.72 (p, J=6.9 Hz, 1 H), 2.43 (s, 1 H), 1.54 (s, 6 H), 1.22-1.16 (m, 18 H); $^{13}$C NMR (CDCl$_3$, 75.5 mHz) δ 179.35, 155.98, 148.61, 148.03, 137.93, 121.46, 88.19, 85.95, 85.63, 84.52, 70.94, 70.35, 67.78, 66.74, 63.53, 58.86, 36.50, 32.36, 25.50, 19.24.

Dye conjugation of 9b with DR-N$_3$: Following similar procedural details described for the dye conjugation of 4b in Example 2A, 9c was produced in a 60% yield from 9b (20.0 g, 33.6 mmol). $^1$H NMR (CDCl$_3$, 300 mHz) δ 8.61 (b, 1 H), 8.31 (d, J=9.0 Hz, 2 H), 8.06 (s, 1 H), 7.90 (d, J=9.0 Hz, 2 H), 7.81 (d, J=9.1 Hz, 2 H), 7.66 (s, 1 H), 6.64 (d, J=9.2 Hz, 2 H), 5.87 (d, J=4.7 Hz, 1 H), 4.64-4.60 (m, 2 H), 4.38 (q, J=4.6 Hz, 1 H), 4.24-4.11 (m, 5 H), 4.07-4.05 (m, 1 H), 3.96-3.85 (m, 2 H), 3.42 (s, 3 H), 3.36 (d, J=7.1 Hz, 2 H), 2.98 (d, J=4.7 Hz, 1 H), 2.60 (p, J=6.9 Hz, 1 H), 1.67 (s, 6 H), 1.23 (d, J=6.9 Hz, 6 H), 1.18-1.10 (m, 15 H); $^{13}$C NMR (CDCl$_3$, 75.5 mHz) δ 179.03, 156.86, 155.78, 155.75, 150.96, 148.29, 147.91, 147.69, 144.17, 137.79, 126.41, 124.89, 122.90, 121.74, 121.65, 111.55, 86.22, 85.01, 84.41, 72.60, 69.72, 66.67, 66.63, 62.62, 58.90, 50.58, 47.91, 45.77, 36.54, 30.98, 30.74, 25.62, 25.55, 25.50, 19.30, 19.15, 12.30.

Phosphitylation of 9c: Following similar procedural details described for the phosphitylation of 4c in Example 2A, 9d was produced in an 87% yield from 9c (18.7 g, 20.0 mmol). $^1$H NMR (CD$_3$CN, 300 mHz) δ 9.35 (b, 1 H), 8.32 (d, J=9.1 Hz, 2 H), 8.10 (s, 1 H), 7.90 (d, J=7.2 Hz, 2 H), 7.77 (d, J=9.2 Hz, 2 H), 7.70 and 7.69 (each as s, 1 H), 6.67 (d, J=9.2 Hz, 2 H), 5.89-5.85 (m, 1 H), 4.58 (t, J=5.9 Hz, 2 H), 4.54-4.45 (m, 1 H), 4.27-4.15 (m, 4 H), 3.94-3.80 (m, 4 H), 3.74-3.55 (m, 2 H), 3.41-3.29 (m, 8H), 2.71-2.61 (m, 1 H), 1.64 (s, 6 H), 1.20-1.14 (m, 30 H), 1.09 (t, J=7.1 Hz, 3 H); $^{31}$P NMR (CD$_3$CN, 121.5 mHz) δ 151.19, 150.37.

G. 5'-DR(OiPr)$_2$-Silyl-2'-OMe-C(NAc) Amidite (10d):

Silylation of (10a): Following similar procedural details described for the silylation of 4a in Example 2A, 10b was produced in a 55% yield from 10a (18.4 g, 50.0 mmol). $^1$H NMR (CDCl$_3$, 300 mHz) δ 8.57 (d, J=7.5 Hz, 1 H), 8.30 (b, 1 H), 7.39 (d, J=7.5 Hz, 1 H), 5.99 (s, 1 H), 4.33-4.21 (m, 4 H), 4.05 (dd, J=12.2 Hz, J=1.7 Hz, 1 H), 4.03-3.97 (m, 1 H), 3.76 (d, J=5.2 Hz, 1 H), 3.71 (s, 3 H), 2.62 (d, J=9.4 Hz, 1 H), 2.43 (s, 1 H), 2.20 (s, 3 H), 1.58 (s, 3 H), 1.54 (s, 3 H), 1.22 (d, J=6.1 Hz, 12 H); $^{13}$C NMR (CD$_3$CN, 75.5 mHz) δ 172.07, 163.87, 156.28, 146.27, 96.73, 89.73, 89.29, 85.22, 84.87, 75.56, 68.84, 67.64, 62.57, 59.43, 32.92, 26.06, 25.37.

Dye conjugation of 10b with DR-N$_3$: Following similar procedural details described for the dye conjugation of 4b in Example 2A, 10c was produced in an 87% yield from 10b (14.6 g, 27.7 mmol). $^1$H NMR (CDCl$_3$, 300 mHz) δ 9.95 (b, 1 H), 8.45 (d, J=7.5 Hz, 1 H), 8.26 (d, J=8.9 Hz, 2 H), 7.86 (d, J=8.9 Hz, 2 H), 7.83 (d, J=9.0 Hz, 2 H), 7.42 (s, 1 H), 7.35 (d, J=7.4 Hz, 1 H), 6.65 (d, J=9.1 Hz, 2 H), 5.91 (s, 1 H), 4.55 (t, J=6.1 Hz, 2 H), 4.23-4.10 (m, 4 H), 3.97-3.88 (m, 4 H), 3.69 (d, J=5.0 Hz, 1 H), 3.64 (s, 3 H), 3.35-3.24 (m, 3 H), 2.21 (s, 3 H), 1.66 (s, 6 H), 1.14 (d, J=6.0 Hz, 12 H), 1.08 (t, J=6.9 Hz, 3 H); $^{13}$C NMR (CDCl$_3$, 75.5 mHz) δ 171.03, 163.11, 156.70, 155.99, 155.11, 150.64, 147.72, 145.19, 144.23, 126.41, 124.84, 122.89, 121.11, 111.53, 96.54, 88.38, 84.11, 83.76, 72.54, 67.05, 66.57, 60.71, 58.92, 50.70, 47.69, 45.98, 30.90, 30.72, 25.52, 25.04, 12.32;

Phosphitylation of 10c: Following similar procedural details described for the phosphitylation of 4c in Example 2A, 10d was produced in an 85% yield from 10c (20.8 g, 24.0 mmol). $^1$H NMR (CD$_3$CN, 300 mHz) δ 8.81 (b, 1 H), 8.34-8.31 (m, 3 H), 7.90 (d, J=9.2 Hz, 2 H), 7.79 (d, J=9.2 Hz, 2 H), 7.59 and 7.57 (each as s, 1 H), 7.24 (d, J=7.5 Hz, 1H), 6.68 (d, J=9.2 Hz, 2H), 5.88-5.86 (m, 1 H), 4.52 (t, J=5.9 Hz, 2 H), 4.33-4.15 (m, 3 H), 4.11-4.02 (m, 3H), 3.91-3.87 (m, 2 H), 3.80-3.78 (m, 1 H), 3.63-3.53 (m, 2 H), 3.51 and 3.49 (each as s, 3 H), 3.38-3.28 (m, 5H), 2.14 and 2.10 (each as s, 3 H), 1.63 and 1.62 (each as s, 6 H), 1.17-1.08 (m, 27 H); $^{31}$P NMR (CD$_3$CN, 121.5 mHz) δ 150.75, 150.21.

H. 5'-DR(OiPr)$_2$-Silyl-2'-OMe-U Amidite (11d):

Silylation of (11a): Following similar procedural details described for the silylation of 4a in Example 2A, 11b was produced in a 27% yield from 11a (11.7 g, 45.3 mmol). $^1$H NMR (CDCl$_3$, 300 mHz) δ 8.06 (d, J=8.2 Hz, 1 H), 5.99 (d, J=3.0 Hz, 1 H), 5.71 (d, J=8.2 Hz, 1 H), 4.33-4.26 (m, 3 H), 4.22-4.15 (m, 1 H), 4.04-4.00 (m, 2 H), 3.78 (dd, J=5.1 Hz, J=3.0 Hz, 1 H), 3.57 (s, 3H), 2.41 (s, 1 H), 1.56 (s, 6 H), 1.20 (d, J=6.1 Hz, 12 H).

Dye conjugation of 11b with DR-N$_3$: Following similar procedural details described for the dye conjugation of 4b in Example 2A and with the exception of the use of 3 equivalents of DRN$_3$, 11c was produced in a 67% yield from 11b (7.3 g, 14.9 mmol). $^1$H NMR (CDCl$_3$, 300 mHz) δ 9.37 (b, 1 H), 8.28 (d, J=8.8 Hz, 2 H), 7.96 (d, J=8.2 Hz, 1 H), 7.88 (d, J=8.7 Hz, 2 H), 7.84 (d, J=9.1 Hz, 2 H), 7.38 (s, 1 H), 6.66 (d, J=9.1 Hz, 2 H), 5.89 (d, J=1.5 Hz, 1 H), 5.59 (d, J=8.1 Hz, 1 H), 4.54 (t, J=6.2 Hz, 2 H), 4.26-4.03 (m, 5 H), 3.94-3.89 (m, 4 H), 3.70 (dd, J=5.1 Hz, J=1.5 Hz, 1 H), 3.56 (s, 3H), 3.28 (q, J=6.8 Hz, 2 H), 1.66 (s, 6 H), 1.14-1.07 (m, 15 H).

Phosphitylation of 11c: Following similar procedural details described for the phosphitylation of 4c in Example 2A, 11d was produced in a 90% yield from 11c (8.4 g, 10.0 mmol). $^1$H NMR (CD$_3$CN, 300 mHz) δ 8.91 (b, 1 H), 8.33 (d, J=9.0 Hz, 2 H), 7.91 (d, J=9.1 Hz, 2 H), 7.81 (d, J=9.2 Hz, 2 H), 7.75 and 7.74 (each as d, J=8.2 Hz, 1 H), 7.58 and 7.57 (each as s, 1 H), 6.70 (d, J=9.2 Hz, 2 H), 5.87 (d, J=4.9 Hz, 1 H), 5.53 (d, J=8.1 Hz, 1 H), 4.57 (t, J=6.0 Hz, 2 H), 4.39-4.30 (m, 1 H), 4.24-4.15 (m, 2 H), 4.10-4.06 (m, 1 H), 3.93-3.79 (m, 5 H), 3.67-3.53 (m, 2 H), 3.40-3.28 (m, 8 H), 1.63 and 1.62 (each as s, 6 H), 1.17-1.08 (m, 27 H); $^{31}$P NMR (CD$_3$CN, 121.5 mHz) δ 151.12, 150.22.

I. 5'-DR(OiPr)$_2$-Silyl-2'-F-C(NAc) Amidite (12d):

N-acetyl protection of 12a: A suspension of 12a (24.5 g, 100.0 mmol) in 500 mL of EtOH with acetic anhydride (71.5 g, 700 mmol) was heated to 70° C. for 3 h. The flask was allowed to cool and the solvents were in vacuo. The resulting oil was coevaporated copiously with absolute EtOH followed by Toluene. The resulting white powder was taken onto the silylation step without any further purification.

Silylation of N-acetyl protected (12a): Following similar procedural details described for the silylation of 4a in Example 2A and with the exception of adding 100 mL of Dimethylformamide to help dissolve 12a, 12b was produced in a 55% yield from 12a (24.5 g, 100 mmol). $^1$H NMR (CDCl$_3$, 300 mHz) δ 8.93 (b, 1 H), 8.38 (d, J=7.5 Hz, 1 H), 7.35 (d, J=7.5 Hz, 1 H), 5.95 (d, J=16.9 Hz, 1 H), 4.96 (dd, J=52.6 Hz, J=3.9 Hz, 1 H), 4.37-4.24 (m, 4 H), 4.11-4.00 (m, 2 H), 3.61 (d, J=7.5 Hz, 1 H,), 2.77 (s, 1 H), 2.15 (s, 3 H), 1.60 (s, 6 H), 1.24 (d, J=6.1 Hz, 12 H); $^{19}$F NMR (CDCl$_3$, 282.4 mHz) δ −203.31.

Dye conjugation of 12b with DR-N$_3$: Following similar procedural details described for the dye conjugation of 4b in Example 2A, 12c was produced in a 67% yield from 12b (28.39 g, 55.0 mmol). $^1$H NMR (CDCl$_3$, 300 mHz) δ 8.76 (b, 1 H), 8.33 (d, J=9.1 Hz, 2 H), 8.30 (d, J=5.4 Hz, 1 H), 7.92 (d, J=9.1 Hz, 2 H), 7.80 (d, J=9.2 Hz, 2 H), 7.62 (s, 1 H), 7.25 (d, J=7.5 Hz, 1 H), 6.71 (d, J=9.3 Hz, 2 H), 5.89 (d, J=17.0 Hz, 1 H), 4.91 (dd, J=52.7 Hz, J=3.9 Hz, 1 H), 4.58 (t, J=6.1 Hz, 2 H), 4.30-4.22 (m, 2 H), 4.21-4.14 (m, 4 H), 4.10-4.05 (m, 1 H), 3.94-3.87 (m, 2 H), 3.35 (q, J=7.1 Hz, 2 H), 2.14 (s, 3 H), 1.62 (s, 6 H), 1.17-1.14 (m, 15 H); $^{19}$F NMR (CDCl$_3$, 282.4 mHz) δ −203.13.

Phosphitylation of 12c: Following similar procedural details described for the phosphitylation of 4c in Example 2A, 12d was produced in a 92% yield from 12c (13.0 g, 28.1 mmol). $^1$H NMR (CD$_3$CN, 300 mHz) δ 8.80 (b, 1 H), 8.35 (d, J=9.0 Hz, 2 H), 8.28 and 8.27 (each as d, J=7.5 Hz, 1 H), 7.92 (d, J=9.0 Hz, 2 H), 7.82 (d, J=9.2 Hz, 2 H), 7.61 and 7.60 (each as s, 1 H), 7.27 (d, J=7.5 Hz, 1 H), 6.71 (d, 9.2 Hz, 1 H), 5.93 (d, J=17.2 Hz, 1 H), 5.02 and 5.00 (each as dd, J=52.2

Hz, J=4.4 Hz, 1 H), 4.60 (t, J=6.0 Hz, 2 H), 4.38-4.13 (m, 5 H), 3.97-3.90 (m, 3 H), 3.64-3.55 (m, 2 H), 3.39-3.32 (m, 5 H), 2.16 and 2.14 (each as s, 3 H), 1.65-1.63 (m, 6 H), 1.19-1.11 (m, 27 H); $^{19}$F NMR (CD$_3$CN, 282.4 mHz) δ −200.66, −200.69, −200.82, −200.85; $^{31}$P NMR (CD$_3$CN, 121.5 mHz) δ 151.52, 151.47, 151.29, 151.23.

J. 5'-DR(OiPr)$_2$-Silyl-2'-F-U Amidite (13d):

Silylation of (13a): Following similar procedural details described for the silylation of 4a in Example 2A, 13b was produced in a 75% yield from 13a (12.3 g, 50.0 mmol). $^1$H NMR (CD$_3$CN, 300 mHz) δ 7.82 (d, J=8.1 Hz, 1 H), 5.95 (dd, J=17.0 Hz, 1.7 Hz, 1 H), 5.61 (d, J=8.1 Hz, 1 H), 4.99 (dd, J=50.3 Hz, J=1.6 Hz, 1 H), 4.33-4.21 (m, 4 H), 4.03-3.96 (m, 4 H), 1.58 (s, 6 H), 1.21 (d, J=6.1 Hz, 12 H).

Dye conjugation of 13b with DR-N$_3$: Following similar procedural details described for the dye conjugation of 4b in Example 2A and with the exception of the use of 3 equivalents of DRN$_3$, 13c was produced in a 59% yield from 13b (24.9 g, 52.0 mmol). $^1$H NMR (CD$_3$CN, 300 mHz) δ 8.93 (b, 1 H), 8.29 (d, J=9.7 Hz, 2 H), 7.87 (d, J=9.1 Hz, 2 H), 7.78 (d, J=9.2 Hz, 2 H), 7.67 (d, J=8.2 Hz, 1 H), 7.58 (s, 1 H), 6.68 (d, J=9.2 Hz, 2 H), 5.84 (dd, J=16.3 Hz, J=1.1 Hz, 1 H), 5.46 (d, J=8.2 Hz, 1 H), 4.89 (dd, J=52.0 Hz, J=4.5 Hz, 1 H), 4.54 (t, J=6.0 Hz, 2 H), 4.25-4.21 (m, 1 H), 4.19-4.13 (m, 3 H), 4.02-3.92 (m, 2 H), 3.88-3.83 (m, 3 H), 3.32 (q, J=7.1 Hz, 2 H), 1.58 (s, 6 H), 1.08-1.05 (m, 15 H); $^{19}$F NMR (CD$_3$CN, 282.4 mHz) δ −203.46

Phosphitylation of 13c: Following similar procedural details described for the phosphitylation of 4c in Example 2A, 13d was produced in an 86% yield from 13c (18.2 g, 22.0 mmol). $^1$H NMR (CD$_3$CN, 300 mHz) δ 8.93 (b, 1H), 8.29 (d, J=9.0 Hz, 2 H), 7.87 (d, J=9.1 Hz, 2 H), 7.77 (d, J=9.2 Hz, 2 H), 7.68 and 7.66 (each as d, J=8.2 Hz, 1 H), 7.54 and 7.53 (each as s, 1 H), 6.67 (d, J=9.3 Hz, 2 H), 5.84 (d, J=28.0 Hz, 1 H), 5.47 and 5.46 (each as d, J=8.1 Hz, 1 H), 4.97 (d, J=48.0 Hz, 1 H), 4.54 (t, J=6.0 Hz, 2 H), 4.18-4.10 (m, 2 H), 4.04-3.99 (m, 2 H), 3.89-3.78 (m, 4 H), 3.62-3.51 (m, 2 H), 3.35-3.27 (m, 5 H), 1.58 and 1.57 (each as s, 6 H), 1.11-1.08 (m, 27 H); $^{19}$F NMR (CD$_3$CN, 282.4 mHz) δ 201.15, −201.19, −201.74, −201.76; $^{31}$P NMR (CD$_3$CN, 121.5 mHz) δ 151.58, 151.53, 151.21, 151.14.

Example 3

Synthesis of 5'-DR(Me)$_2$ Silyl Amidites

A. 5'-DR(Me)$_2$-Silyl-rA(NiBu) Amidite (14d):

Silylation of 14a: Diisopropylamine (21.6 g, 213.1 mmol) was added to a solution of 14a (59.2 g, 106.6 mmol) in 1 L of CH$_2$Cl$_2$ and the solution was cooled to 0° C. In a separate flask DMMBSiCl (26.2 g, 127.9 mmol) was diluted in 240 mL of CH$_2$Cl$_2$ under a gentle stream of Argon. Diisopropylamine (15.5 g, 153.5 mmol) was added to the silylating solution and the solution was allowed to stir for 2 min before being added dropwise to the nucleoside solution. The addition was completed within 30 min and the reaction was allowed to slowly warm to room temperature overnight. The following morning TLC analysis showed consumption of starting material. The reaction was stopped by addition of 30 mL of MeOH and evaporated to dryness. The crude material was purified by flash chromatography on 1.5 L silica gel using a gradient of ethyl acetate and acetone in hexanes [0:2:8 (v/v/v) to 4:2:4 (v/v/v)] containing 0.1% (v/v) Et$_3$N. Product fractions were pooled and evaporated to afford 14b as a colorless oil. The yield was 62.8 g (85%). $^1$H NMR (CDCl$_3$, 300 mHz) δ 8.66 (s, 1 H), 8.42 (s, 1 H), 6.26 (d, J=4.9 Hz, 1 H), 5.38 (s, 1 H), 4.83 (t, J=4.9 Hz, 1 H), 4.45 (q, J=4.5 Hz, 1 H), 4.23-4.12 (m, 1 H), 4.08-4.02 (m, 2 H), 3.95-3.90 (m, 2 H), 3.86-3.82 (m, 1 H), 3.74-3.47 (m, 3 H), 3.44-3.39 (m, 1 H), 3.19-3.14 (m, 1 H), 3.05 (d, J=4.5 Hz, 1 H), 2.42 (s, 1 H), 2.03 (s, 6 H), 1.54 (s, 6 H), 1.20 (s, 6 H), 0.12 (s, 6 H); $^{13}$C NMR (CDCl$_3$, 75.5 mHz) δ 176.10, 170.86, 152.70, 151.24, 149.36, 141.67, 122.32, 112.55, 141.67, 122.32, 112.55, 88.48, 86.95, 85.30, 77.36, 71.48, 70.63, 66.70, 63.24, 62.88, 62.75, 62.01, 60.46, 36.23, 32.76, 20.89, 19.27, 14.27, −0.88.

Dye conjugation of 14b with DR-N$_3$: Copper Iodide (1.7 g, 8.9 mmol) was added to a solution of 14b (61.8 g, 88.8 mmol), DR-N$_3$ (39.2 g, 115.4 mmol), and iPr$_2$NEt (11.5 g, 88.8 mmol) in 1000 mL of Toluene. The solution was sonicated for 1 min and then stirred at room temperature for 3.5 h. The solution was then partitioned between ethyl acetate and saturated NaCl. The aqueous phase was back extracted once with ethyl acetate to remove all red color from the water layer. The organic phases were combined and concentrated. The crude material was purified by flash chromatography on 1.2 L silica gel using a gradient of ethyl acetate and acetone in hexanes [2:2:6 (v/v/v) to 6:2:2 (v/v/v)] containing 0.1% (v/v) Et$_3$N. Product fractions were pooled and evaporated to afford 14c as a red foam. The yield was 82.9 g (90%). $^1$H NMR (CD$_3$CN, 300 mHz) δ 8.63 (b, 1 H), 8.51 (s, 1 H), 8.31 (s, 1 H), 8.26 (d, J=9.1 Hz, 2 H), 7.71 (d, J=9.2 Hz, 2 H), 7.61 (s, 1 H), 6.62 (d, J=9.2 Hz, 2 H), 6.12 (d, J=4.8 Hz, 1 H), 5.35 (s, 1 H), 4.76 (t, J=4.9 Hz, 1 H), 4.49 (t, J=6.1 Hz, 2 H), 4.34 (q, J=4.7 Hz, 1 H), 4.03-3.91 (m, 7 H), 3.84-3.75 (m, 4 H), 3.72-3.55 (m, 4 H), 3.51-3.43 (s, 1 H), 3.28 (q, J=7.1 Hz, 2 H), 3.01 (p, J=6.8 Hz, 1 H), 1.88 (s, 3 H), 1.87 (s, 3 H), 1.51 (s, 6 H), 1.12 (d, J=5.3 Hz, 6 H), 1.02 (t, J=7.0 Hz, 3 H), −0.03 (s, 6 H); $^{13}$C NMR (CD$_3$CN, 75.5 mHz) δ 176.63, 171.40, 157.11, 156.31, 153.13, 151.61, 151.03, 149.77, 148.15, 144.67, 142.09, 126.83, 125.27, 123.33, 122.94, 121.50, 113.04, 111.98, 87.88, 85.19, 71.94, 70.10, 63.74, 63.52, 63.42, 63.33, 61.77, 51.02, 48.20, 46.38, 36.68, 31.75, 31.63, 21.42, 19.78, 12.75, 0.00.

Phosphitylation of 14c: Bis(diisopropylamino) methoxy phosphine (31.2 g, 119.1 mmol) was dissolved in 300 mL of CH$_2$Cl$_2$ and a 0.5 M solution of 5-ethylthio-1-H-tetrazole in anhydrous acetonitrile (79 mL, 39.7 mmol) was added. Diisopropylamine (8.0 g, 79.4 mmol) was then added and the phosphine solution was allowed to stir for 5 min at ambient temperature. In a separate flask, 14c (82.2 g, 79.4 mmol) and diisopropylamine (8.0 g, 79.4 mmol) were dissolved in 700 mL of CH$_2$Cl$_2$. The activated phosphine solution was added into the nucleoside solution and the reaction was stirred at room temperature. After 16 h the reaction was quenched with 50 mL of absolute ethanol and concentrated to dryness. The resulting paste was purified by flash chromatography on 1.5 L of silica gel using a mixture of CH$_2$Cl$_2$ in hexanes (5:95 (v/v) containing 2% (v/v) Et$_3$N followed by acetone in hexanes (2:8 (v/v) to 4:6 (v/v) containing 0.5% (v/v) Et$_3$N. Product fractions were pooled and evaporated to afford 14d as a red foam. The yield was 62.5 g (66%). $^1$H NMR (CDCl$_3$, 300 mHz) δ 8.51 (s, 1 H), 8.32 and 8.31 (each as s, 1 H), 8.27 (d, J=9.1 Hz, 2 H), 7.87 (d, J=8.7 Hz, 2 H), 7.73 (d, J=9.0 Hz, 2 H), 7.61 and 7.59 (each as s, 1 H), 6.63 (d, J=8.1 Hz, 2 H), 6.13 (t, J=5.0 Hz, 1 H), 5.32 and 5.27 (each as s, 1 H), 4.89 (q, J=5.1 Hz, 1 H), 4.58-4.48 (m, 3 H), 4.20-4.18 and 4.14-4.12 (each as m, 1 H), 3.95-3.73 (m, 8 H), 3.62-3.49 (m, 6 H), 3.36-3.26 (m, 6 H), 3.02 (p, J=6.6 Hz, 1 H), 1.96-1.92 (m, 6 H), 1.52 and 1.50 (each as s, 6 H), 1.16-1.10 (m, 18 H), 1.04 (t, J=6.0 Hz, 3 H), −0.01--0.04 (m, 6 H); $^{31}$P NMR (CD$_3$CN, 121.5 MHz) δ 150.74, 150.21.

B. 5'-DR(Me)$_2$-Silyl-rG(NiBu) Amidite (15d):

Silylation of 15a: Following similar procedural details described for the silylation of 14a in Example 3A, 15b was produced in an 83% yield from 15a (57.2 g, 100.0 mmol). $^1$H NMR (CDCl$_3$, 300 mHz) δ 8.11 (s, 1 H), 7.24 (s, 1 H), 6.03 (d, J=4.2 Hz, 1 H), 5.35 (s, 1 H), 4.22-4.15 (m, 1 H), 4.12-4.10 (m, 1 H), 4.04-3.89 (m, 2 H), 3.82-3.70 (m, 7 H), 3.65-3.58 (m, 2 H), 3.05 (d, J=4.1 Hz, 1 H), 2.71 (p, J=6.9 Hz, 1 H), 2.50 (s, 1 H), 2.07 (s, 3 H), 2.06 (s, 3 H), 1.50 (s, 6 H), 1.24-1.21 (m, 6 H), 0.23 (s, 3 H), 0.22 (s, 3 H); $^{13}$C NMR (CDCl$_3$, 75.5 mHz) δ 179.11, 171.66, 171.30, 155.61, 148.10, 147.93, 137.25, 121.16, 112.69, 88.67, 86.19, 84.79, 71.49, 70.39, 60.69, 63.26, 63.15, 62.86, 62.77, 61.71, 36.21, 32.69, 54.01, 19.04, −0.94.

Dye conjugation of 15b with DR-N$_3$: Following similar procedural details described for the dye conjugation of 14b in Example 3A, 15c was produced in a 93% yield from 15b (58.0 g, 81.5 mmol). $^1$H NMR (CD$_3$CN, 300 mHz) δ 9.42 (b, 1 H), 8.28 (d, J=9.1 Hz, 2 H), 7.94 (s, 1 H), 7.85 (d, J=9.0 Hz, 2 H), 7.74 (d, J=9.2 Hz, 2 H), 7.63 (s, 1 H), 6.65 (d, J=9.3 Hz, 2 H), 5.88 (d, J=5.1 Hz, 1 H), 5.36 (s, 1 H), 4.64 (d, J=5.0 Hz, 1 H), 4.52 (t, J=7.1 Hz, 2 H), 4.31 (q, J=4.7 Hz, 2 H), 4.05-3.80 (m, 5 H), 3.74 (t, J=3.5 Hz, 2 H), 3.65 (t, J=4.3 Hz, 2 H), 3.62-3.55 (m, 3 H), 3.54-3.49 (m, 2 H), 3.31 (q, J=7.1 Hz, 2 H), 2.62 (p, J=6.8 Hz, 1 H), 1.93 (s, 3 H), 1.91 (s, 3 H), 1.53 (s, 6 H), 1.18-1.11 (m, 6 H), 1.06 (t, J=7.1 Hz, 3 H), 0.00 (s, 6 H); $^{13}$C NMR (CDCl$_3$, 75.5 mHz) δ 179.84, 172.31, 171.87, 157.19, 156.10, 156.08, 151.24, 148.53, 148.47, 148.08, 137.84, 126.82, 125.26, 123.29, 121.89, 121.76, 113.20, 111.96, 8716, 84.67, 79.08, 71.85, 69.78, 63.80, 63.75, 63.57, 62.86, 61.33, 60.98, 50.96, 48.24, 76.23, 36.50, 31.67, 31.59, 21.64, 21.51, 19.63, 14.77, 12.72, 0.00.

Phosphitylation of 15c: Following similar procedural details described for the phosphitylation of 14c in Example 3A, 15d was produced in an 88% yield from 15c (78.3 g, 74.5 mmol). $^1$H NMR (CD$_3$CN, 300 mHz) δ 8.34 (d, J=9.0 Hz, 2 H), 8.06 and 8.04 (each as s, 1 H), 7.94 (d, J=9.0 Hz, 2 H), 7.80 (d, J=9.0 Hz, 2 H), 7.71 and 7.70 (each as s, 1 H), 6.72 (d, J=9.0 Hz, 2 H), 5.98 (t, J=6.2 Hz, 1 H), 5.40 and 5.36 (each as s, 1 H), 4.80 (t, J=5.7 Hz, 2 H), 4.59 (t, J=6.2 Hz, 3 H), 4.53-4.44 (m, 1 H), 4.24-4.17 and 4.08-4.02 (each as m, 1 H), 4.00-3.92 (m, 4 H), 3.90-3.60 (m, 9 H), 3.58-3.35 (m, 5 H), 1.98 (s, 3 H), 1.96 (s, 3 H), 1.62 and 1.61 (each as s, 6 H), 1.23-1.18 (m, 18 H), 1.13 (t, J=6.4 Hz, 3 H), 0.10-0.08 (m, 6 H); $^{31}$P NMR (CD$_3$CN, 121.5 mHz) δ 150.86, 150.51.

C. 5'-DR(Me)$_2$-Silyl-rC(NAc) Amidite 16d):

Silylation of 16a: Following similar procedural details described for the silylation of 14a in Example 3A, 16b was produced in a 73% yield from 16a (53.4 g, 106.6 mmol). $^1$H NMR (CDCl$_3$, 300 mHz) δ 9.50 (s, 1 H), 8.57 (d, J=7.5 Hz, 1 H), 7.36 (d, J=7.5 Hz, 1 H), 5.94 (s, 1 H), 5.68 (s, 1 H) 4.29-4.07 (m, 8 H), 3.59-3.81 (m, 5 H), 2.98 (d, J=8.1 Hz, 1 H) 2.46 (s, 1 H), 2.23 (s, 3 H), 2.02 (s, 3 H), 2.01 (s, 3 H), 1.51 (s, 6 H), 0.23 (s, 6 H); $^{13}$C NMR (CDCl$_3$, 75.5 mHz) δ 169.86, 161.52, 153.73, 143.79, 111.62, 94.89, 88.24, 87.03, 82391, 70.08, 65.86, 65.36, 61.77, 61.70, 61.68, 61.54, 59.81, 58.43, 31.39, 23.62, 19.57, 12.88, −2.39.

Dye conjugation of 16b with DR-N$_3$: Following similar procedural details described for the dye conjugation of 14b in Example 3A, 16c was produced in a 98% yield from 16b (48.6 g, 75.5 mmol). $^1$H NMR (CDCl$_3$, 300 mHz) δ 8.55 (d, J=7.5 Hz, 1 H), 8.33 (m, 3 H), 7.93 (d, J=9.0 Hz, 2 H), 7.89 (d, J=9.2 Hz, 2 H), 7.37 (s, 1 H), 6.70 (d, J=9.2 Hz, 2 H), 5.93 (s, 1 H), 5.79 (s, 1 H), 5.79 (s, 1 H), 4.58 (t, J=6.3 Hz, 2 H), 4.32-4.08 (m, 8 H), 3.97-3.87 (m, 7 H), 3.71 (d, J=8.0 Hz, 1 H), 3.35 (d, J=7.1 Hz, 2 H), 2.20 (s, 3 H), 2.07 (s, 3 H), 2.04 (s, 3 H), 1.62 (s, 6 H) 1.15 (t, J=7.0 Hz, 3 H), 0.12 (s, 6 H); $^{13}$C NMR (CDCl$_3$, 75.5 mHz) δ 170.97, 169.82, 162.14, 156.55, 155.69, 150.45, 147.33, 145.11, 144.14, 126.27, 124.72, 122.76, 120.80, 112.84, 111.40, 95.55, 89.82, 83.85, 78.31, 71.38, 66.69, 32.21, 63.17, 62.86, 59.39, 50.44, 47.61, 45.50, 31.16, 31.09, 25.06, 20.92, 12.19, −0.50, −0.65.

Phosphitylation of 16c: Following similar procedural details described for the phosphitylation of 14c in Example 3A, 16d was produced in an 86% yield from 16c (71.9 g, 73.1 mmol). $^1$H NMR (CD$_3$CN, 300 mHz) δ 8.75 (b, 1 H), 8.32-8.26 (m, 3 H), 7.85 (d, J=9.1 Hz, 2 H), 7.75 (d, J=9.1 Hz, 2 H), 7.58 and 7.57 (each as s, 1 H), 7.17 (d, J=7.5 Hz, 1H), 6.65 (d, J=8.7 Hz, 2 H), 5.90 (s, 1 H), 5.61 and 5.57 (each as s, 1 H), 4.52 (t, J=6.1 Hz, 2 H), 4.27-4.18 (m, 2 H), 4.12-4.03 (m, 5 H), 3.94-3.66 (m, 8 H), 3.56-3.44 (m, 2 H), 3.37-3.24 (m, 5 H), 2.10 (s, 3 H), 1.94 (s, 6 H), 1.55-1.54 (m, 6 H), 1.13-1.06 (m, 15 H), 0.02- −0.01 (m, 6 H); $^{31}$P NMR (CD$_3$CN, 121.5 mHz) δ 150.88, 150.20.

D. 5'-DR(Me)$_2$-Silyl-rU Amidite (17d):

Silylation of 17a: Following similar procedural details described for the silylation of 14a in Example 3A, 17b was produced in a 94% yield from 17a (47.5 g, 102.8 mmol). $^1$H NMR (CDCl$_3$, 300 mHz) δ 9.26 (b, 1 H), 8.09 (d, J=8.2 Hz, 1 H), 5.99 (d, J=3.1 Hz, 1 H), 5.66 (d, J=8.2 Hz, 1 H), 5.51 (s, 1 H), 4.34-4.31 (m, 1 H), 4.26-4.15 (m, 5 H), 4.10-4.06 (m, 2 H), 3.93-3.90 (m, 1 H), 3.84-3.76 (m, 4 H), 2.94 (b, 1 H), 2.46 (s, 1 H), 2.05 (s, 3 H), 2.03 (s, 3 H), 1.51 (s, 6 H), 0.22 (s, 6 H); $^{13}$C NMR (CDCl$_3$, 75.5 mHz) δ 170.87, 163.80, 150.71, 140.28, 112.58, 102.01, 88.29, 87.74, 84.44, 77.51, 71.53, 68.81, 66.62, 63.15, 63.04, 62.97, 62.93, 60.82, 60.36, 32.67, 20.79, −1.02, −1.13.

Dye conjugation of 17b with DR-N$_3$: Following similar procedural details described for the dye conjugation of 14b in Example 3A, 17c was produced in a 92% yield from 17b (56.4 g, 93.6 mmol). $^1$H NMR (CDCl$_3$, 300 mHz) δ 8.92 (b, 1 H), 8.30 (d, J=9.0 Hz, 2 H), 8.06 (d, J=8.2 Hz, 1 H), 7.90 (d, J=9.0 Hz, 2 H), 7.86 (d, J=9.2 Hz, 2 H), 7.33 (s, 1 H), 6.68 (d, J=9.2 Hz, 2 H), 5.90 (d, J=1.8 Hz, 1 H), 5.60-5.57 (m, 2 H), 4.56 (t, J=7.1 Hz, 2 H), 4.31-4.20 (m, 6 H), 4.06-3.78 (m, 10 H), 3.32 (q, J=7.1 Hz, 2 H), 2.05 (s, 3 H), 2.03 (s, 3 H), 1.61 (s, 6 H), 1.13 (t, J=7.0 Hz, 3 H), 0.08 (s, 3 H), 0.06 (s, 3 H); $^{13}$C NMR (CDCl$_3$, 75.5 mHz) δ 170.91, 163.76, 156.42, 155.45, 150.51, 147.33, 143.92, 140.19, 126.20, 124.59, 122.69, 121.02, 112.43, 111.33, 101.68, 88.16, 83.91, 71.28, 67.98, 63.10, 62.77, 62.63, 60.14, 50.40, 47.63, 45.73, 31.11, 31.02, 20.83, 12.11, −0.66, −0.76.

Phosphitylation of 17c: Following similar procedural details described for the phosphitylation of 14c in Example 3A, 17d was produced in a 92% yield from 17c (79.2 g, 84.1 mmol). $^1$H NMR (CD$_3$CN, 300 mHz) δ 9.08 (b, 1 H), 8.31 (d, J=8.8 Hz, 2 H), 7.90 (d, J=8.70 Hz, 2 H), 7.84-7.78 (m, 3 H), 7.62 and 7.61 (each as s, 1 H), 6.71 (d, J=9.2 Hz, 2 H), 5.97-5.93 (m, 1 H), 5.50 (d, J=8.1 Hz, 1 H), 5.46 and 5.41 (each as s, 1 H), 4.57 (t, J=6.1 Hz, 2 H), 4.38-4.26 (m, 2 H), 4.15-4.07 (m, 6 H), 3.92-3.85 (m, 2 H), 3.82-3.77 (m, 1 H), 3.75-3.64 (m, 5 H), 3.62-3.53 (m, 2 H), 3.41-3.30 (m, 5 H), 1.98 (s, 6 H), 1.59 and 1.58 (each as s, 6 H), 1.17-1.10 (m, 15 H), 0.06-0.03 (m, 6 H); $^{31}$P NMR (CD$_3$CN, 121.5 mHz) δ 150.77, 150.53.

E. 5'-DR(Me)$_2$-Silyl-2'-OMe-A(NiBu) Amidite (18d):

Silylation of 18a: Following similar procedural details described for the silylation of 14a in Example 3A, 18b was produced in a 70% yield from 18a (17.6 g, 50.0 mmol). $^1$H NMR (CDCl$_3$, 300 mHz) δ 9.14 (b, 1 H), 8.63 (s, 1 H), 8.47 (s, 1 H), 6.21 (d, J=3.5 Hz, 1 H), 4.45 (q, J=5.3 Hz, 1 H), 4.15-4.11 (m, 2 H), 4.02 (dd, J=11.7 Hz, J=2.6 Hz, 1 H), 3.90 (dd, J=11.7 Hz, J=2.3 Hz, 1 H), 3.58 (d, J=6.2 Hz, 1 H), 3.47 (s, 3 H), 3.11 (p, J=6.8 Hz, 1 H), 2.42 (s, 1 H), 1.44 (s, 6 H), 1.20 (d, J=6.8 Hz, 6 H), 0.17 (s, 6 H); $^{13}$C NMR (CDCl$_3$, 75.5 mHz) δ 176.41, 152.62, 151.03, 149.41, 122.41, 88.41, 86.53, 85.14, 84.55, 71.44, 69.23, 66.64, 61.43, 58.79, 36.05, 32.72, 19.26, −0.89.

Dye conjugation of 18b with DR-$N_3$: Following similar procedural details described for the dye conjugation of 14b in Example 3A, 18c was produced in an 89% yield from 18b (17.1 g, 35.0 mmol). $^1$H NMR (CDCl$_3$, 300 mHz) δ 8.72 (b, 1 H), 8.65 (s, 1 H), 8.45 (s, 1 H), 8.25 (d, J=9.0 Hz, 2 H), 7.87 (d, J=9.6 Hz, 2 H), 7.84 (d, J=9.4 Hz, 2 H), 7.44 (s, 1 H), 6.65 (d, J=9.2 Hz, 2 H), 6.20 (d, J=2.5 Hz, 1 H), 4.56-4.45 (m, 3 H), 4.11-3.98 (m, 3 H), 3.91-3.86 (m, 3 H), 3.57 (s, 4 H), 3.28 (q, J=7.1 Hz, 2 H), 3.17 (p, J=7.2 Hz, 1 H), 2.49 (m, 1 H), 1.62 (s, 6 H), 1.24 (d, J=7.3 Hz, 6 H), 1.11 (t, J=7.0 Hz, 3 H), 0.01 (s, 6 H); $^{13}$C NMR (CDCl$_3$, 75.5 mHz) δ 176.37, 156.75, 156.06, 152.78, 151.04, 150.72, 149.45, 147.76, 144.28, 141.45, 126.48, 124.91, 122.97, 122.66, 121.31, 111.62, 86.77, 84.70, 84.54, 71.74, 68.82, 60.91, 60.64, 59.06, 50.70, 47.83, 46.04, 36.33, 31.45, 31.37, 19.46, 12.39, −0.20, −0.33.

Phosphitylation of 18c: Following similar procedural details described for the phosphitylation of 14c in Example 3A, 18d was produced in a 79% yield from 18c (25.5 g, 31.0 mmol). $^1$H NMR (CD$_3$CN, 300 mHz) δ 8.85 (b, 1 H), 8.57 (s, 1 H), 8.39 and 8.38 (each as s, 1 H), 8.29 (d, J=9.0 Hz, 2 H), 7.87 (d, J=8.9 Hz, 2 H), 7.75 (d, J=9.2 Hz, 2 H), 7.67 and 7.65 (each as s, 1 H), 6.67 (d, J=9.2 Hz, 2 H), 6.12 and 6.11 (each as d, J=5.0 Hz, 1 H), 4.63-4.53 (m, 3 H), 4.44-4.36 (m, 1 H), 4.22-4.17 (m, 1 H), 3.92-3.74 (m, 4 H), 3.68-3.56 (m, 2 H), 3.42-3.29 (m, 8 H), 3.09 (p, J=6.8 Hz, 1 H), 1.58 and 1.57 (each as s, 6 H), 1.21-1.15 (m, 18 H), 1.08 (t, J=6.9 Hz, 3 H), 0.04-0.02 (m, 6 H); $^{31}$P NMR (CD$_3$CN, 121.5 mHz) δ 151.00, 149.85.

F. 5'-DR(Me)$_2$-Silyl-2'-OMe-G(NiBu) Amidite (19d):

Silylation of 19a: Following similar procedural details described for the silylation of 14a in Example 3A, 19b was produced in a 54% yield from 19a (18.4 g, 50.0 mmol). $^1$H NMR (CDCl$_3$, 300 mHz) δ 8.15 (s, 1 H), 5.80 (d, J=3.7 Hz, 1 H), 4.43 (t, J=16.2, 4.9 Hz, 1 H), 4.06-3.84 (m, 4 H), 3.25 (s, 3 H), 2.92 (p, J=6.8 Hz, 1 H), 2.43 (s, 1 H), 1.42 (s, 6 H), 1.17-1.14 (m, 6 H) 0.14 (s, 6 H); $^{13}$C NMR (CDCl$_3$, 75.5 mHz) δ 180.64, 156.31, 148.70, 148.58, 137.63, 120.70, 88.35, 86.28, 85.26, 84.82, 71.47, 69.38, 66.59, 61.85, 58.48, 35.94, 32.68, 19.11, −0.95.

Dye conjugation of 19b with DR-$N_3$: Following similar procedural details described for the dye conjugation of 14b in Example 3A, 19c was produced in a 44% yield from 19b (13.6 g, 27.0 mmol). $^1$H NMR (CDCl$_3$, 300 mHz) δ 8.20 (d, J=9.0 Hz, 2 H), 7.11 (s, 1 H), 7.82 (d, J=9.0 Hz, 2 H), 7.74 (d, J=9.0 Hz, 2 H), 7.61 (s, 1 H), 6.61 (d, J=9.2 Hz, 2 H), 5.85 (d, J=3.6 Hz, 1 H), 4.62 (t, J=5.9 Hz, 2 H), 4.42-4.39 (m, 1 H), 4.09-3.98 (m, 3 H), 3.90-3.79 (m, 4 H), 3.34-3.29 (m, 5 H), 2.82 (p, J=6.8 Hz, 1 H), 1.58 (s, 6 H), 1.22-1.16 (m, 6 H), 1.07 (t, J=7.1 Hz, 3 H), 0.04 (s, 3 H), 0.03 (s, 3 H). $^{13}$C NMR (CDCl$_3$, 75.5 mHz) δ 180.10, 171.33, 156.67, 155.98, 155.79, 150.79, 148.42, 148.30, 147.44, 144.02, 137.66, 126.28, 124.71, 122.78, 121.57, 121.13, 111.45, 86.23, 84.76, 84.32, 71.53, 69.13, 61.35, 60.50, 58.63, 50.48, 47.80, 45.71, 36.09, 31.28, 31.18, 19.20, 19.11, −0.43, −0.55.

Phosphitylation of 19c: Following similar procedural details described for the phosphitylation of 14c in Example 3A, 19d was produced in a 67% yield from 19c (10.1 g, 11.9 mmol). $^1$H NMR (CD$_3$CN, 300 mHz) δ 8.25 (d, J=8.8 Hz, 2 H), 8.06 and 8.04 (each as s, 1 H) 7.83 (d, J=8.8 Hz, 2 H), 7.74-7.70 (m, 3 H), 6.65 (d, J=8.9 Hz, 2 H), 5.86-5.84 (m, 1 H), 4.57 (t, J=6.0 Hz, 2 H), 4.47-4.42 (m, 1 H), 4.27-4.11 (m, 2 H), 3.90-3.75 (m, 4 H), 3.74-3.53 (m, 2 H), 3.42-3.29 (m, 8 H), 2.72-2.63 (m, 1 H), 1.59 and 1.58 (each as s, 6 H), 1.17-1.04 (m, 21 H), 0.06-0.03 (m, 6 H); $^{31}$P NMR (CD$_3$CN, 121.5 mHz) δ 150.90, 150.12.

G. 5'-DR(Me)$_2$-Silyl-2'-OMe-C(NAc) Amidite (20d):

Silylation of 20a: Following similar procedural details described for the silylation of 14a in Example 3A, 20b was produced in a 74% yield from 20a (15.0 g, 50.0 mmol). $^1$H NMR (CDCl$_3$, 300 mHz) δ 10.59 (b, 1 H), 8.58 (d, J=7.5 Hz, 1 H), 7.34 (d, J=7.5 Hz, 1 H), 5.92 (s, 1 H), 4.15-4.09 (m, 2 H), 3.96-3.89 (m, 2 H), 3.69 (d, J=5.1 Hz, 1 H), 3.62 (s, 3 H), 2.87 (d, J=7.5 Hz, 1 H), 2.44 (s, 1 H), 2.23 (s, 3 H), 1.48 (s, 6 H), 0.20 (s, 6 H); $^{13}$C NMR (CDCl$_3$, 75.5 mHz) δ 171.54, 163.50, 155.08, 145.28, 96.62, 88.41, 88.25, 84.21, 84.09, 71.54, 67.18, 66.74, 59.78, 58.78, 37.79, 24.89, −0.84, −0.98.

Dye conjugation of 20b with DR-$N_3$: Following similar procedural details described for the dye conjugation of 14b in Example 3A, 20c was produced in an 86% yield from 20b (16.1 g, 37.0 mmol). $^1$H NMR (CDCl$_3$, 300 mHz) δ 10.30 (b, 1 H), 8.53 (d, J=7.5 Hz, 1 H), 8.22 (d, J=8.1 Hz, 2 H), 7.83 (d, J=8.3 Hz, 2 H), 7.79 (d, J=8.7 Hz, 2 H), 7.43 (s, 1 H), 7.28 (d, J=7.4 Hz, 1 H), 6.64 (d, J=8.9 Hz, 2 H), 5.89 (s, 1 H), 4.56 (t, J=6.1 Hz, 2 H), 4.15-4.13 (m, 1 H), 4.07-4.01 (m, 1 H), 3.96-3.84 (m, 4 H), 3.69 (d, J=4.9 Hz, 1 H), 3.63 (s, 3 H), 3.39 (d, J=9.1 Hz, 1 H), 3.27 (q, J=6.9 Hz, 2 H), 2.22 (s, 3 H), 1.61 (s, 6 H), 1.08 (t, J=6.9 Hz, 3 H), 0.08 (s, 6 H); $^{13}$C NMR (CDCl$_3$, 75.5 mHz) δ 171.33, 163.20, 156.59, 155.79, 155.01, 150.61, 147.56, 145.16, 144.10, 126.32, 124.74, 122.81, 121.15, 111.46, 96.30, 88.29, 84.00, 83.83, 71.55, 66.83, 60.48, 59.55, 58.76, 50.56, 47.68, 45.87, 31.22, 29.94, 12.25, −0.38, −0.56.

Phosphitylation of 20c: Following similar procedural details described for the phosphitylation of 14c in Example 3A, 20d was produced in a 58% yield from 20c (25.1 g, 32.0 mmol). $^1$H NMR (CD$_3$CN, 300 mHz) δ 9.34 (b, 1 H), 8.38 and 8.36 (each as d, J=6.3 Hz, 1 H), 8.23 (d, J=9.0 Hz, 2 H), 7.82 (d, J=8.9 Hz, 2 H), 7.73 (d, J=9.1 Hz, 2 H), 7.63 and 7.62 (each as s, 1 H), 7.20 (d, J=7.5 Hz, 1 H), 6.65 (d, J=8.9 Hz, 2 H), 5.83 (s, 1 H), 4.54 (t, J=6.1 Hz, 2 H), 4.24-4.18 (m, 1 H), 4.12-3.94 (m, 2 H), 3.88-3.72 (m, 4 H), 3.58-3.51 (m, 5 H), 3.39-3.25 (m, 5 H), 2.10 (s, 3 H), 1.59 and 1.57 (each as s, 6 H), 1.10-1.07 (m, 15 H), 0.06-0.02 (m, 6 H); $^{31}$P NMR (CD$_3$CN, 121.5 mHz) δ 150.28, 149.78.

H. 5'-DR(Me)$_2$-Silyl-2'-OMe-U Amidite (21d):

Silylation of 21a: Following similar procedural details described for the silylation of 14a in Example 3A, 21b was produced in an 81% yield from 21a (12.9 g, 50.0 mmol). $^1$H NMR (CDCl$_3$, 300 mHz) δ 9.76 (b, 1 H), 8.15 (d, J=8.1 Hz, 1 H), 5.95 (d, J=1.8 Hz, 1 H), 5.65 (d, J=8.1 Hz, 1 H), 4.27-4.23 (m, 2 H), 4.10 (dd, J=11.8 Hz, J=1.7 Hz, 1 H), 3.97-3.91 (m, 2 H), 3.73 (dd, J=5.1 Hz, J=1.8 Hz, 1 H), 3.59 (s, 3 H), 2.44 (s, 1 H), 1.51 (s, 6 H), 0.22 (s, 6 H); $^{13}$C NMR (CDCl$_3$, 75.5 mHz) δ 164.74, 163.65, 151.40, 141.30, 102.84, 56.34, 88.02, 85.31, 85.13, 72.35, 68.86, 67.68, 61.28, 59.65, 37.55, 33.73, 33.71, 32.49, −0.49.

Dye conjugation of 21b with DR-$N_3$: Following similar procedural details described for the dye conjugation of 14b in Example 3A, 21c was produced in a 93% yield from 21b (16.1 g, 40.4 mmol). $^1$H NMR (CDCl$_3$, 300 mHz) δ 8.51 (b, 1 H), 8.34 (d, J=8.9 Hz, 2 H), 8.15 (d, J=8.2 Hz, 1 H), 7.93 (d, J=8.9 Hz, 2 H), 7.90 (d, J=9.1 Hz, 2 H), 7.39 (s, 1 H), 6.71 (d, J=9.2 Hz, 2 H), 5.91 (s, 1 H), 5.61 (d, J=8.2 Hz, 1 H), 4.59 (t, J=6.2 Hz, 2 H), 4.26-4.22 (m, 1 H), 4.26-4.16 (m, 1 H), 4.07-3.87 (m, 5 H), 3.72 (d, J=5.1 Hz, 1 H), 3.63 (s, 3 H), 3.33 (q, J=7.1 Hz, 3 H), 3.23 (d, J=8.6 Hz, 1 H), 1.62 (s, 6 H), 1.15 (t, J=7.2 Hz, 3 H), 0.12 (s, 3 H), 0.11 (s, 3H); $^{13}$C NMR (CDCl$_3$, 75.5 mHz) δ 171.85, 163.61, 157.21, 156.44, 151.10, 150.56, 148.35, 140.85, 126.95, 125.40, 123.45, 121.56, 112.10, 102.19, 87.82, 84.78, 84.52, 72.19, 67.96, 61.09, 60.34, 59.33, 51.16, 48.30, 46.55, 31.92, 31.82, 12.86, 0.68, 0.18.

Phosphitylation of 21c: Following similar procedural details described for the phosphitylation of 14c in Example 3A, 21d was produced in a 75% yield from 21c (17.7 g, 24.0 mmol). $^1$H NMR (CD$_3$CN, 300 mHz) δ 9.38 (b, 1 H), 8.31 (d, J=8.8 Hz, 2 H), 7.91-7.81 (m, 3 H), 7.80 (d, J=9.0 Hz, 2 H), 7.65 and 7.64 (each as s, 1 H), 6.71 (d, J=9.1 Hz, 2 H), 5.88 (d, J=3.5 Hz, 1 H), 5.60 (d, J=8.1 Hz, 1 H), 4.59 (t, J=6.0 Hz, 2 H), 4.32-4.30 (m, 1 H), 4.11-4.07 (m, 1 H), 3.93-3.77 (m, 4 H), 3.54-3.56 (m, 3 H), 3.44-3.36 (m, 8 H), 1.62 and 1.61 (each as s, 6 H), 1.18-1.13 (m, 15 H), 0.08-0.06 (m, 6 H); $^{31}$P NMR (CD$_3$CN, 121.5 mHz) δ 150.95, 149.92.

I. 5'-DR(Me)$_2$-Silyl-2'-F-C(NAc) Amidite (22d):

Silylation of 22a: N-acetyl protection of 22a (24.5 g, 100 mmol) was carried out in the same fashion as described in Example 2I. The silylation was performed following similar procedural details described for the silylation of 14a in Example 3A and with the exception of adding 100 mL of Dimethylformamide to help dissolve 22a, 22b was produced in a 30% yield from 22a (24.5 g, 100 mmol). $^1$H NMR (CDCl$_3$, 300 mHz) δ 8.52 (d, J=7.5 Hz, 1 H), 7.38 (d, J=7.5 Hz, 1 H), 6.01 (d, J=1.5 Hz, 1 H), 5.07 (dd, J=51.9 Hz, J=3.8 Hz, 1 H), 4.35-4.28 (m, 1 H), 4.26-4.13 (m, 3 H), 3.95 (d, J=11.8 Hz, 1 H), 2.47 (s, 1 H), 2.24 (s, 3 H), 1.50 (s, 6 H), 0.22 (s, 6 H); $^{13}$C NMR (CDCl$_3$, 75.5 mHz) δ 171.31, 163.29, 155.34, 145.11, 96.86, 95.51, 93.03, 89.31, 88.87, 88.45, 83.28, 71.64, 67.57, 67.35, 66.85, 59.68, 46.17, 32.84, 25.07, 11.36, −0.75, −0.93; $^{19}$F NMR (CDCl$_3$, 282.4 mHz) δ −202.31.

Dye conjugation of 22b with DR-N$_3$: Following similar procedural details described for the dye conjugation of 14b in Example 3A, 22c was produced in a 50% yield from 22b (12.6 g, 29.5 mmol). $^1$H NMR (CDCl$_3$, 300 mHz) δ 9.69 (b, 1 H), 8.55 (d, J=7.5 Hz, 1 H), 8.30 (d, J=9.0 Hz, 2 H), 7.91 (d, J=9.7 Hz, 2 H), 7.85 (d, J=9.0 Hz, 2 H), 7.36 (s, 1 H), 7.33 (d, J=7.4 Hz, 1 H), 6.67 (d, J=9.2 Hz, 2 H), 6.01 (d, J=15.3 Hz, 1 H), 5.38-5.33 (m, 1 H), 5.05 (dd, J=51.8 Hz, J=5.9 Hz, 1 H), 4.58 (t, J=6.2 Hz, 3 H), 4.21-4.01 (m, 2 H), 3.97-3.88 (m, 3 H), 3.32 (q, J=7.0 Hz, 2 H), 2.26 (s, 3 H), 1.61 (s, 6 H), 1.12 (t, J=6.9 Hz, 3 H), 0.10 (s, 3 H), 0.08 (s, 3 H); $^{13}$C NMR (CDCl$_3$, 75.5 mHz) δ 171.90, 163.69, 157.21, 155.90, 155.66, 151.12, 148.31, 145.75, 144.83, 126.97, 125.41, 123.48, 121.45, 112.12, 96.96, 96.13, 96.63, 90.01, 89.57, 83.52, 71.39, 67.27, 67.07, 65.09, 61.12, 59.81, 51.06, 48.51, 46.53, 31.77, 31.35, 25.70, 21.78, 19.84, 14.92, 14.43, 12.88, 0.72, 0.60; $^{19}$F NMR (CDCl$_3$, 282.4 mHz) δ −202.68.

Phosphitylation of 22c: Following similar procedural details described for the phosphitylation of 14c in Example 3A, 22d was produced in a 63% yield from 22c (11.3 g, 14.7 mmol). $^1$H NMR (CD$_3$CN, 300 mHz) δ 8.90 (s, 1 H), 8.32-8.29 (m, 3 H), 7.88 (d, J=7.2 Hz, 2 H), 7.78 (d, J=9.2 Hz, 2 H), 7.62 and 7.61 (each as s, 1 H), 7.21 (d, J=7.5 Hz, 1 H), 6.69 (d, J=9.2 Hz, 2 H), 5.89 (d, J=16.8 Hz, 1 H), 4.95 (dt, J=54.0 Hz, J=3.8 Hz, 1 H), 4.56 (t, J=6.0 Hz, 2 H), 4.38-4.26 (m, 2 H), 4.13-4.02 (m, 2 H), 3.90-3.75 (m, 3 H), 3.60-3.49 (m, 2 H), 3.41-3.28 (m, 5 H), 2.15 (s, 3 H), 1.59-1.58 (m, 6 H), 1.17-1.09 (m, 15 H), 0.06-0.03 (m, 6 H); $^{19}$F NMR (CD$_3$CN, 282.4 mHz) δ −200.94, −200.97, −201.05, −201.07; $^{31}$P NMR (CD$_3$CN, 121.5 mHz) 151.05, 151.00, 150.86, 150.81.

J. 5'-DR(Me)$_2$-Silyl-2'-F-U Amidite (23d):

Silylation of 23a: Following similar procedural details described for the silylation of 14a in Example 3A, 23b was produced in ~90% yield (wet with solvent) from 23a (12.3 g, 50.0 mmol). $^1$H NMR (CDCl$_3$, 300 mHz) δ 8.16 (d, J=8.1 Hz, 1 H), 7.25 (b, 2 H), 6.15 (d, J=15.0 Hz, 1H), 5.77 (d, J=8.1 Hz, 1 H), 5.07 (d, J=54.8 Hz, 1 H), 4.53-4.43 (m, 1 H), 4.23-4.02 (m, 3 H), 2.64 (s, 1 H), 1.61 (s, 6 H), 0.32 (s, 6 H); $^1$H NMR (CDCl$_3$, 75.5 mHz) δ 164.93, 150.85, 140.50, 102.09, 95.29, 92.80, 88.36, 87.76, 87.32, 83.39, 77.79, 77.36, 76.94, 71.72, 68.35, 68.13, 66.74, 60.33, 45.90, 45.22, 21.56, 21.46, 10.14, −0.96, −1.05; $^{19}$F NMR (CDCl$_3$, 282.4 mHz) δ −202.86.

Dye conjugation of 23b with DR-N$_3$: Following similar procedural details described for the dye conjugation of 14b in Example 3A, 23c was produced in a 49% yield from 23a (12.3 g, 50.0 mmol). $^1$H NMR (CDCl$_3$, 300 mHz) δ 8.25 (d, J=9.0 Hz, 2 H), 8.08 (d, J=8.2 Hz, 1 H), 7.88 (d, J=9.1 Hz, 2 H), 7.85 (d, J=8.8 Hz, 2 H), 7.45 (s, 1 H), 6.67 (d, J=9.2 Hz, 2 H), 5.99 (d, J=15.5 Hz, 1 H), 5.60 (d, J=8.1 Hz, 1 H), 4.95 (dd, J=52.4 Hz, J=3.5 Hz, 1 H), 4.60 (t, J=5.9 Hz, 2 H), 4.14-4.03 (m, 2 H), 3.97-3.94 (m, 4 H), 3.32 (q, J=6.9 Hz, 2 H), 1.62 (s, 6 H), 1.12 (t, J=7.1 Hz, 3 H). 0.09 (s, 3 H), 0.07 (s, 3 H); $^{13}$C NMR (CDCl$_3$, 75.5 mHz) δ 172.00, 163.36, 157.25, 155.96, 151.22, 150.85, 148.28, 14.84, 140.94, 127.02, 125.45, 123.54, 121.64, 112.18, 102.45, 96.30, 96.87, 88.89, 88.44, 83.59, 71.56, 67.96, 67.75, 65.15, 61.19, 60.21, 51.14, 48.58, 48.41, 46.60, 37.33, 31.85, 21.84, 14.97, 12.96, 0.78, 0.51; $^{19}$F NMR (CDCl$_3$, 282.4 mHz) δ −202.43.

Phosphitylation of 23c: Following similar procedural details described for the phosphitylation of 14c in Example 3A, 23d was produced in a 75% yield from 23c (17.7 g, 24.4 mmol). $^1$H NMR (CD$_3$CN, 300 mHz) δ 9.27 (b, 1 H), 8.33 (d, J=8.7 Hz, 2 H), 7.91 (d, J=8.8 Hz, 2 H), 7.86-7.80 (m, 3 H), 7.64 and 7.63 (each as s, 1 H), 6.72 (d, J=9.1 Hz, 2 H), 5.93 (d, J=16.8 Hz, 1 H), 5.58 (d, J=8.2 Hz, 1 H), 5.00 (dd, J=52.3 Hz, J=4.1 Hz, 1 H), 4.59 (t, J=6.0 Hz, 2 H), 4.52-4.26 (m, 1 H), 4.12-3.56 (m, 9 H), 3.43-3.33 (m, 5 H), 1.61 and 1.60 (each as s, 6 H), 1.17-1.14 (m, 15 H), 0.08-0.06 (m, 6 H); $^{19}$F NMR (CD$_3$CN, 282.4 mHz) δ −196.23, −196.27, −196.63, −196.66; $^{31}$P NMR (CD$_3$CN, 121.5 mHz) δ 151.15, 151.09, 150.89, 150.78.

Example 4

Synthesis of 5'-DR(OTMS)$_2$ Silyl Amidites

A. 5'-DR(OTMS)$_2$ rA(NiBu) Amidite (24d):

2'-MP-orthoformate protection and desilylation of 5',-3'-Tipds rA N(iBu) (24a): A mixture 5',-3'-Tipds rA N(iBu) (60.0 g, 103.5 mmol), PTS (5.2 g, 20.7 mmol), and MP-orthoformate (47.9 g, 217.3 mmol) was dissolved in 200 mL of CH$_2$Cl$_2$. After 2 h, TBDMS-pentanedione (39.9 g, 186.3 mmol) was added and the reaction was stirred at ambient temperature. After 5 days, TLC analysis showed that reaction was complete whereupon TEMED (6.0 g, 51.7 mmol) was added. The crude material was separated from excess reagents by flash chromatography [1500 mL silica gel—80:20 Hexane:Ethyl acetate (v/v) with 0.1% TEMED (v/v) to 50:50 Hexane:Ethyl acetate (v/v)]. This material was concentrated to near dryness and taken directly onto the desilylation reaction.

To an ice cooled solution of TEMED (58.1 g, 500 mmol) in 200 mL of CH$_3$CN is slowly added 48% aqueous HF (12.6 mL, 350 mmol). The solution is stirred for 5 min and added to the foregoing material from above at room temperature. The reaction was stirred for 3 h and concentrated to dryness. The crude material was purified by flash chromatography [1000 mL silica gel—80:20 Ethyl acetate:Hexane (v/v) with 0.1% TEMED to 96:4 Ethyl acetate: MeOH (v/v)] to afford 24a as a white foam (39.0 g, 80%—two steps). $^1$H NMR (CDCl$_3$, 300 mHz) δ 8.77 (b, 1 H), 8.67 (s, 1 H), 8.04 (s, 1 H), 6.08 (d, J=11.2 Hz, 1 H), 5.98 (d, J=7.5 Hz, 1 H), 5.40 (s, 1 H), 5.11 (dd, J=7.4 Hz, J=4.8 Hz, 1 H), 4.57 (d, J=4.7 Hz, 1 H), 4.34 (b, 1 H), 4.11-3.87 (m, 5 H), 3.79-3.71 (m, 1 H), 3.26 (p, J=6.8 Hz, 1 H), 3.19 (s, 1 H), 1.76 (s, 3 H), 1.68 (s, 3 H), 1.27 (d, J=6.8 Hz, 6 H); $^{13}$C NMR (CDCl$_3$, 75.5 mHz) δ 176.84, 151.90, 150.22, 150.09, 143.58, 123.34, 110.88, 89.40, 87.59, 83.44, 83.27, 75.90, 73.39, 73.18, 71.98, 63.10, 53.77, 53.61, 35.88, 19.18, 19.12, 3.43, 3.35.

Silylation of 24a: Diisopropylamine (19.9 g, 140.3 mmol) was added to a solution of 24a (34.2 g, 70.2 mmol) in 750 mL of CH$_2$Cl$_2$ and the solution was cooled to 0° C. In a separate flask BTMBSiCl (27.4 g, 84.2 mmol) was diluted in 250 mL of CH$_2$Cl$_2$. Diisopropylamine (14.3 g, 101.0 mmol) was added to the silylating solution and the solution was allowed to stir for 2 min before being added dropwise to the nucleoside solution. The addition was completed within 2 h and the reaction was allowed to slowly warm to room temperature overnight. The following morning TLC analysis showed consumption of ~85% of the starting material. A further 0.2 equivalents of BTMBSiCl (4.6 g, 14.0 mmol—activated in the same fashion as above) was added over 15 min at room temperature. After 2 h, the reaction was stopped by addition of 30 mL of MeOH and evaporated to dryness. The crude material was purified by flash chromatography on 1.2 L silica gel using a gradient of ethyl acetate and acetone in hexanes [0:2:8 (v/v/v) to 2:2:6 (v/v/v)] containing 0.1% (v/v) Et$_3$N. Product fractions were pooled and evaporated to afford 24b as a colorless oil. The yield was 44.9 g (83%). $^1$H NMR (CDCl$_3$, 300 mHz) δ 8.85 (b, 1 H), 8.65 (s, 1 H), 8.36 (s, 1 H), 6.30 (d, J=5.7 Hz, 1 H), 5.55 (s, 1 H), 4.84 (t, J=5.4 Hz, 1 H), 4.47-4.42 (m, 1 H), 4.20-4.17 (m, 1 H), 4.07-4.03 (m, 2 H), 4.00-3.94 (m, 1 H), 3.87-3.82 (m, 3 H), 3.32-3.16 (m, 2 H), 2.38 (s, 1 H), 1.69 (s, 3 H), 1.66 (s, 3 H), 1.47 (s, 6 H), 1.21 (d, J=7.1 Hz, 6 H), 0.07 (s, 18 H); $^{13}$C NMR (CDCl$_3$, 75.5 mHz) δ 176.47, 152.59, 151.50, 149.28, 142.07, 122.22, 110.68, 88.14, 86.63, 85.40, 83.27, 83.24, 76.53, 73.54, 73.51, 71.36, 70.78, 67.16, 63.00, 53.90, 53.74, 35.97, 32.20, 19.24, 3.51, 1.68.

Dye conjugation of 24b with DR-N$_3$: Copper Iodide (1.10 g, 5.8 mmol) was added to a solution of 24b (44.7 g, 57.6 mmol), DR-N$_3$ (25.4 g, 74.9 mmol), and iPr$_2$NEt (7.45 g, 57.6 mmol) in 600 mL of Toluene. The solution was sonicated for 1 min and then stirred at room temperature for 4 h. The solution was then partitioned between ethyl acetate and saturated NaCl. The aqueous phase was back extracted once with ethyl acetate to remove all red color from the water layer. The organic phases were combined and concentrated. The crude material was purified by flash chromatography on 1.2 L silica gel using a gradient of ethyl acetate and acetone in hexanes [2:2:6 (v/v/v) to 4:2:4 (v/v/v)] containing 0.1% (v/v) Et$_3$N. Product fractions were pooled and evaporated to afford 24c as a red foam. The yield was 61.2 g (95%). $^1$H NMR (CDCl$_3$, 300 mHz) δ 8.64 (b, 1 H), 8.32-8.28 (m, 4 H), 7.90 (d, J=9.0 Hz, 2 H), 7.83 (d, J=9.0 Hz, 2 H), 7.44 (s, 1 H), 6.66 (d, J=9.2 Hz, 2 H), 6.24 (d, J=5.3 Hz, 1 H), 5.60 (s, 1 H), 4.90 (t, J=5.2 Hz, 1 H), 4.52 (t, J=6.3 Hz, 2 H), 4.46-4.42 (m, 1 H), 4.18-4.14 (m, 3 H), 3.98-3.81 (m, 6 H), 3.29 (q, J=7.1 Hz, 3 H), 3.12-3.11 (m, 1 H), 1.74-1.72 m, 6 H), 1.66 (s, 6 H), 1.27 (d, J=6.8 Hz, 6 H), 1.10 (t, J=7.1 Hz, 3 H), 0.09 (s, 18 H); $^{13}$C NMR (CDCl$_3$, 75.5 mHz) δ 176.37, 156.56, 156.25, 152.52, 151.37, 150.56, 149.18, 147.47, 144.02, 141.86, 126.26, 125.07, 122.72, 122.28, 121.05, 111.74, 110.92, 86.85, 85.05, 83.31, 83.26, 76.12, 73.55, 72.48, 70.79, 62.68, 53.91, 53.83, 50.52, 47.52, 45.73, 36.77, 30.81, 30.76, 19.21, 12.16, 3.94, 1.65.

Phosphitylation of 24c: Bis(diisopropylamino) methoxy phosphine (21.5 g, 82.0 mmol) was dissolved in 150 mL of CH$_2$Cl$_2$ and a 0.5 M solution of 5-ethylthio-1-H-tetrazole in anhydrous acetonitrile (54.7 mL, 27.3 mmol) was added. Diisopropylamine (5.5 g, 54.7 mmol) was then added and the phosphine solution was allowed to stir for 5 min at ambient temperature. In a separate flask, 24c (61.0 g, 54.7 mmol) and diisopropylamine (5.5 g, 54.7 mmol) were dissolved in 350 mL of CH$_2$Cl$_2$. The activated phosphine solution was added into the nucleoside solution and the reaction was stirred at room temperature. After 18 h the reaction was quenched with 50 mL of absolute ethanol and concentrated to dryness. The resulting paste was purified by flash chromatography on 2 L of silica gel using a mixture of CH$_2$Cl$_2$ in hexanes (5:95 (v/v) containing 2% (v/v) Et$_3$N followed by acetone in hexanes (1:9 (v/v) to 3:7 (v/v) containing 0.5% (v/v) Et$_3$N. Product fractions were pooled and evaporated to afford 24d as a red foam. The yield was 64.5 g (92%). $^1$H NMR (CD$_3$CN, 300 mHz) δ 8.76 (b, 1 H), 8.56 (s, 1 H), 8.36 and 8.34 (each as s, 1 H), 8.30 (d, J=8.7 Hz, 2 H), 7.88 (d, J=8.6 Hz, 2 H), 7.75 (d, J=9.1 Hz, 2 H), 7.63 and 7.62 (each as d, 1 H), 6.64 (d, J=9.3 Hz, 2 H), 6.18-6.14 (m, 1 H), 5.46 and 5.43 (each as s, 1 H), 5.03-4.98 (m, 1 H), 4.63-4.52 (m, 3 H), 4.28-4.20 (m, 1 H), 4.06-3.96 (m, 4 H), 3.87-3.77 (m, 4 H), 3.70-3.60 (m, 2 H), 3.41 and 3.35 (each as d, J=13.2 Hz, 3 H), 3.31-3.24 (m, 2 H), 3.10 (p, J=6.9 Hz, 1 H), 1.74-1.65 (m, 6 H), 1.62-1.60 (m, 6 H), 1.23-1.16 (m, 18 H) 1.06 and 1.05 (each as t, J=7.1 Hz, 3 H), 0.10-0.08 (m, 18 H); $^{31}$P NMR (CD$_3$CN, 121.5 mHz) δ 151.02, 149.98.

B. 5'-DR(OTMS)$_2$-Silyl-rG(NiBu) Amidite (25d):

2'-MP-orthoformate protection and desilylation of 5',-3'-Tipds rG N(iBu) (25a): Following similar procedural details described for the 2'-protection and desilylation of 24a in Example 4A, 25a was produced in a 52% yield from 5',-3'-Tipds rG N(iBu) (60.0 g, 100.7 mmol). $^1$H NMR (CDCl$_3$, 300 mHz) δ 9.25 (b, 1 H), 7.96 (s, 1 H), 5.91 (d, J=6.5 Hz, 1 H), 5.49 (s, 1 H), 5.08 (b, 1 H), 4.91 (t, J=5.7 Hz, 1 H), 4.53-4.51 (m, 1 H), 4.23-4.21 (m, 1 H), 4.10-4.01 (m, 2 H), 3.95-3.87 (m, 3 H), 3.78-3.74 (m, 1 H), 5.52 (b, 1 H), 2.80 (p, J=6.8 Hz, 1 H), 1.75 (s, 6 H), 1.26-1.20 (m, 6 H), $^{13}$C NMR (CDCl$_3$, 75.5 mHz) δ 180.20, 155.79, 148.38, 148.30, 139.36, 121.37, 110.90, 87.96, 86.34, 83.32, 75.84, 73.67, 71.00, 62.39, 54.02, 53.73, 36.16, 19.10, 19.06, 3.54.

Silylation of 25a: Following similar procedural details described for the silylation of 24a in Example 4A, 25b was produced in 77% yield from 25a (30.6 g, 60.81 mmol). $^1$H NMR (CDCl$_3$, 300 mHz) δ 8.81 (b, 1 H), 8.09 (s, 1 H), 5.98 (d, J=6.9 Hz, 1 H), 5.47 (s, 1 H), 4.77 (t, J=5.4 Hz, 1 H), 4.41-4.40 (m, 1 H), 4.22-4.20 (m, 1 H), 4.10-4.08 (m, 1 H), 3.95-3.84 (m, 4 H), 2.97 (b, 1 H), 2.69 (p, J=6.9 Hz, 1 H), 2.46 (s, 1 H), 1.75 (s, 6 H), 1.53 (s, 6 H), 1.25-1.21 (m, 6 H), 0.13-0.10 (m, 18 H); $^{13}$C NMR (CDCl$_3$, 75.5 mHz) δ 179.56, 156.04, 148.95, 147.92, 137.87, 121.14, 110.62, 88.14, 85.88, 85.57, 83.25, 83.20, 73.61, 73.54, 71.64, 70.95, 67.26, 63.40, 53.88, 53.77, 35.26, 32.22, 19.15, 19.09, 3.55, 1.72.

Dye conjugation of 25b with DR-N$_3$: Following similar procedural details described for the dye conjugation of 24b in Example 4A, 25c was produced in an 84% yield from 25b (37.0 g, 46.7 mmol). $^1$H NMR (CDCl$_3$, 300 mHz) δ 9.85 (b, 1 H), 8.24 (d, J=9.0 Hz, 2 H), 8.11 (s, 1 H), 7.84 (d, J=9.0 Hz, 2 H), 7.53 (d, J=9.2 Hz, 3 H), 6.61 (d, J=9.2 Hz, 2 H), 5.95 (d, J=6.1 Hz, 1 H), 5.47 (s, 1 H), 4.75-4.62 (m, 3 H), 4.32-4.28 (m, 1 H), 4.13-4.05 (m, 3 H), 3.89-3.74 (m, 6 H), 3.46 (b, 1 H), 3.36-3.31 (m, 2 H), 2.80 (p, J=6.8 Hz, 1 H), 1.68 (s, 6 H), 1.64 (s, 3 H), 1.62 (s, 3 H), 1.22-1.17 (m, 6 H), 1.08 (t, J=7.0 Hz, 3 H), 0.07 (s, 9 H), 0.05 (s, 9 H); $^{13}$C NMR (CDCl$_3$, 75.5 mHz) δ 179.55, 156.79, 155.94, 155.84, 150.99, 148.81, 148.01, 147.44, 144.00, 137.95, 126.31, 124.73, 122.75, 121.83, 121.21, 111.44, 110.72, 86.23, 85.32, 83.30. 73.67. 72.49. 71.33. 62.85. 53.94. 53.77, 50.52, 47.81, 45.59, 36.20, 30.97, 30.60, 19.16, 19.13, 12.16, 3.57, 1.74.

Phosphitylation of 25c: Following similar procedural details described for the phosphitylation of 24c in Example 4A, 25d was produced in a 96% yield from 25c (44.0 g, 38.9 mmol). $^1$H NMR (CD$_3$CN, 300 mHz) δ 8.31 (d, J=9.7 Hz, 2 H), 8.09 and 8.07 (each as s, 1 H), 7.89 (d, J=8.9 Hz, 2 H), 7.77 (d, J=9.2 Hz, 2 H), 7.70 and 7.68 (each as s, 1 H), 6.68 (d, J=9.2 Hz, 2 H), 5.96-5.92 (m, 1 H), 5.46 and 5.43 (each as s, 1 H), 4.81-4.75 (m, 2 H), 4.61-4.56 (m, 1 H), 4.50-4.39 (m, 1 H), 4.20-4.18 (m, 1 H), 4.10-4.04 (m, 2 H), 3.99-3.97 (m, 1 H), 3.89-3.73 (m, 5 H), 3.69-3.57 (m, 2 H), 3.43-3.31 (m, 5 H), 2.72-2.62 (m, 1 H), 1.75-1.71 (m, 6 H), 1.64 and 1.63 (each as s, 6 H), 1.22-1.16 (m, 18 H), 1.09 (t, J=5.9 Hz, 3 H), 0.12-0.10 (m, 18 H); $^{31}$P NMR (CD$_3$CN, 121.5 mHz) δ 151.21, 150.64.

C. 5'-DR(OTMS)$_2$-Silyl-rC(Ndmf) Amidite (26d):

2'-MP-orthoformate protection and desilylation of 5',-3'-Tipds rC N(dmf) (26a): Following similar procedural details described for the 2'-protection and desilylation of 24a in Example 4A, 26a was produced in a 30% yield from 5',-3'-Tipds rC N(dmf) (54.0 g, 100.0 mmol). $^1$H NMR (CDCl$_3$, 300 mHz) δ 8.62 (s, 1 H), 7.79 (d, J=7.2 Hz, 1 H), 5.94 (d, J=7.2 Hz, 1 H), 5.65-5.62 (m, 1 H), 4.58-4.54 (m, 1 H), 4.32-4.29 (m, 1 H), 4.13-4.10 (m, 5 H), 4.02-3.95 (m, 2 H), 3.87-3.83 (m, 1 H), 3.72-3.68 (m, 1 H), 3.02 (d, J=13.3 Hz, 6 H), 1.69 (s, 6 H); $^{13}$C NMR (CDCl$_3$, 75.5 mHz) δ 171.94, 158.57, 143.94, 111.31, 102.88, 92.38, 85.28, 82.98, 76.37, 74.12, 73.98, 69.02, 61.14, 53.62, 53.48, 41.52, 35.79, 3.53.

Silylation of 26a: Following similar procedural details described for the silylation of 24a in Example 4A, 26b was produced in a 79% yield from 26a (17.0 g, 23.0 mmol). $^1$H NMR (CDCl$_3$, 300 mHz) δ 8.78 (s, 1 H), 8.02 (d, J=7.2 Hz, 1 H), 6.08 (d, J=2.8 Hz, 1 H), 5.98 (d, J=7.2 Hz, 1 H), 5.79 (d, 1 H), 4.32-4.26 (m, 3 H), 4.22-4.14 (m, 4 H), 4.08-3.99 (m, 2 H), 3.98 (dd, J=11.6 Hz, J=1.8 Hz, 1 H), 3.08 (d, J=4.4 Hz, 6 H), 2.36 (s, 1 H), 1.79-1.75 (m, 6 H), 1.49 (s, 6 H), 0.10 (s, 18 H); $^{13}$C NMR (CDCl$_3$, 75.5 mHz) δ 171.81, 158.52, 156.25, 141.78, 111.30, 102.72, 88.56, 88.00, 83.97, 82.80, 77.85, 74.26, 74.14, 70.60, 68.45, 66.98, 61.41, 53.80, 53.65, 41.35, 35.06, 32.14, 3.57, 1.63.

Dye conjugation of 26b with DR-N$_3$: Following similar procedural details described for the dye conjugation of 24b in Example 4A, 26c was produced in a 79% yield from 26b (17.4 g, 23.6 mmol). $^1$H NMR (CDCl$_3$, 300 mHz) δ 8.78 (s, 1 H), 8.31 (d, J=8.8 Hz, 2H), 7.94-7.85 (m, 5 H), 7.42 (s, 1 H), 6.68 (d, J=9.0 Hz, 2 H), 6.06 (d, J=2.3 Hz, 1 H), 5.90 (d, J=7.2 Hz, 1 H), 5.82 (s, 1 H), 4.54-4.50 (m, 2 H), 4.37-4.34 (m, 1 H), 4.31-4.30 (m, 2 H), 4.25-4.23 (m, 1 H), 4.19-4.13 (m, 2 H), 4.02-4.01 (m, 2 H), 3.91-3.87 (m, 3 H), 3.33 (q, J=7.1 Hz, 2 H), 3.09-3.06 (m, 7 H), 1.81-1.77 (m, 6 H), 1.64 (s, 6 H), 1.13 (t, J=7.0 Hz, 3 H), 0.09 (s, 18 H); $^{13}$C NMR (CDCl$_3$, 75.5 mHz) δ 171.92, 158.66, 156.70, 156.61, 156.29, 150.68, 147.61, 144.17, 141.59, 126.39, 124.77, 122.84, 121.05, 111.51, 111.45, 102.81, 89.11, 83.85, 83.12, 83.07, 74.34, 74.22, 72.69, 68.32, 61.44, 54.08, 53.99, 50.57, 47.56, 45.77, 41.53, 35.25, 30.98, 12.28, 3.75, 1.80, 1.77.

Phosphitylation of 26c: Following similar procedural details described for the phosphitylation of 24c in Example 4A, 26d was produced in an 86% yield from 26c (20.0 g, 18.6 mmol). $^1$H NMR (CD$_3$CN, 300 mHz) δ 8.65 (s, 1 H), 8.31 (d, J=8.8 Hz, 2 H), 7.89 (d, J=8.8 Hz, 2 H), 7.86 (d, J=7.3 Hz, 1 H), 7.79 (d, J=9.1 Hz, 2 H), 7.57 and 7.56 (each as s, 1 H), 6.69 (d, J=9.2 Hz, 2 H), 6.04-6.04 (m, 1 H), 5.82 and 5.81 (each as d, J=7.2 Hz, 1 H), 5.65 and 5.61 (each as s, 1 H), 4.58-4.54 (m, 2 H), 4.34-4.27 (m, 2 H), 4.20-4.07 (m, 5 H), 3.95-3.75 (m, 4 H), 3.65-3.52 (m, 2 H), 3.39-3.30 (m, 5 H), 3.07 (d, J=23.7 Hz, 6 H), 1.78-1.76 m, 6 H), 1.61 and 1.60 (each as s, 6 H), 1.18-1.07 (m, 15 H), 0.11 and 0.10 (each as s, 18 H); $^{31}$P NMR (CD$_3$CN, 121.5 mHz) δ 150.74, 150.37.

D. 5'-DR(OTMS)$_2$-Silyl-rU Amidite (27d):

2'-MP-orthoformate protection and desilylation of 5',-3'-Tipds rU (25a): Following similar procedural details described for the 2'-protection and desilylation of 24a in Example 4A, 27a was produced in a 63% yield from 5',-3'-Tipds, rU (50.0 g, 102.7 mmol). $^1$H NMR (CDCl$_3$, 300 mHz) δ 10.05 (b, 1 H), 7.66 (d, J=7.0 Hz, 1 H), 5.77 (d, J=4.9 Hz, 1 H), 5.70 (d, J=8.0 Hz, 1 H), 5.57 (s, 1 H), 4.57 (t, J=5.0 Hz, 1 H), 4.32-4.29 (m, 1 H), 4.18-4.14 (m, 4 H), 4.04-4.00 (m, 1 H), 3.87-3.83 (m, 1 H), 3.75-3.71 (m, 1 H), 3.42 (b, 2 H), 1.76 (s, 6 H); $^{13}$C NMR (CDCl$_3$, 75.5 mHz) δ 164.26, 150.78, 142.51, 111.08, 102.44, 90.37, 85.26, 83.53, 69.98, 61.81, 54.02, 53.96, 3.57.

Silylation of 27a: Following similar procedural details described for the silylation of 24a in Example 4A, 27b was produced in an 80% yield from 27a (22.0 g, 55.78 mmol). $^1$H NMR (CDCl$_3$, 300 mHz) δ 7.83 (d, J=8.1 Hz, 1 H), 6.08 (d, J=5.4 Hz, 1 H), 5.65 (d, J=8.1 Hz, 1 H), 5.57 (s, 1 H), 4.33 (t, J=5.2 Hz, 1 H), 4.22-4.19 (m, 1 H), 4.16-4.14 (m, 2 H), 4.09-3.99 (m, 3 H), 3.94-3.79 (m, 2 H), 2.37 (s, 1 H), 1.74-1.72 (m, 6 H), 1.45 (s, 6 H), 0.07 (s, 18 H); $^{13}$C NMR (CDCl$_3$, 75.5 mHz) δ 171.16, 163.94, 150.82, 140.67, 110.70, 102.71, 87.98, 86.75, 84.80, 83.27, 83.23, 76.30, 73.88, 73.84, 70.85, 70.29, 67.16, 32.58, 60.39, 54.00, 53.79, 32.21, 32.19, 21.02, 14.21, 3.54, 1.69.

Dye conjugation of 27b with DR-N$_3$: Following similar procedural details described for the dye conjugation of 24b in Example 4A, 27c was produced in a 91% yield from 27b (29.4 g, 43.0 mmol). $^1$H NMR (CDCl$_3$, 300 mHz) δ 8.31 (d, J=7.2 Hz, 2 H), 8.11 (b, 1 H), 7.92 (d, J=9.0 Hz, 2 H), 7.88 (d, J=9.2 Hz, 2 H), 7.79 (d, J=8.2 Hz, 1 H), 7.33 (s, 1 H), 6.69 (d, J=9.2 Hz, 2 H), 6.05 (d, J=4.9 Hz, 1 H), 5.65 (s, 1 H), 5.58 (d, J=8.1 Hz, 1 H), 4.54 (t, J=6.3 Hz, 2 H), 4.39 (d, J=5.1 Hz, 1 H), 4.24-4.19 (m, 3 H), 4.16-4.14 (m, 2 H), 4.06-4.05 (m, 1 H), 3.95-3.89 (m, 3 H), 3.82-3.78 (m, 1 H), 3.33 (q, J=6.9 Hz, 2 H), 3.05 (d, J=4.1 Hz, 1 H), 1.80-1.78 (m, 6 H), 1.64 (s, 6 H), 1.13 (t, J=7.0 Hz, 3 H), 0.09 (s, 18 H); $^{13}$C NMR (CDCl$_3$, 75.5 mHz) δ 163.68, 156.63, 156.16, 150.63, 147.57, 144.13, 140.53, 126.36, 124.74, 122.82, 120.94, 111.45, 111.02, 110.80, 102.53, 87.29, 84.49, 83.45, 76.07, 73.90, 73.87, 72.49, 69.77, 62.28, 54.10, 53.97, 47.65, 45.84, 30.87, 12.24, 3.65, 1.74.

Phosphitylation of 27c: Following similar procedural details described for the phosphitylation of 24c in Example 4A, 27d was produced in an 82% yield from 27c (37.0 g, 36.2 mmol). $^1$H NMR (CD$_3$CN, 300 mHz) δ 9.17 (b, 1 H), 8.31 (d, J=7.1 Hz, 2 H), 7.89 (d, J=9.0 Hz, 2 H), 7.80 (d, J=9.2 Hz, 2 H), 7.67 (d, J=8.2 Hz, 1 H), 7.56 and 7.55 (each as s, 1 H), 6.70 (d, J=9.2 Hz, 2 H), 5.97 and 5.96 (each as d, J=6.7 Hz, 1 H), 5.55-5.50 (m, 2 H), 4.57 (t, J=5.9 Hz, 2 H), 4.41-4.26 (m, 2 H), 4.17-4.07 (m, 5 H), 3.91-3.86 (m, 2 H), 3.84-3.71 (m, 2 H), 3.66-3.54 (m, 2 H), 3.41-3.27 (m, 5 H), 1.78-1.76 (m, 6 H), 1.61 and 1.60 (each as s, 6 H), 1.20-1.08 (m, 15 H), 0.11 and 0.09 (each as s, 18 H); $^{31}$P NMR (CD$_3$CN, 121.5 mHz) δ 150.59, 149.55.

E. 5'-DR(OTMS)$_2$-Silyl-2'-OMe-A(NiBu) Amidite (28d):

Silylation of 28a: Following similar procedural details described for the silylation of 24a in Example 4A, 28b was produced in a 77% yield from 28a (17.6 g, 50.0 mmol). $^1$H NMR (CDCl$_3$, 300 mHz) δ 8.69 (s, 1 H), 8.47 (s, 1 H), 8.44 (b, 1 H), 6.26 (d, J=4.7 Hz, 1 H), 4.48 (q, J=4.4 Hz, 1 H), 4.23 (t, J=4.8 Hz, 1 H), 4.20-4.17 (m, 1 H), 4.06 (dd, J=12.0 Hz, J=2.8 Hz, 1 H), 3.94 (dd, J=12.0 Hz, J=2.31 Hz, 1 H), 3.48 (s, 3 H), 3.31 (p, J=6.8 Hz, 1 H), 2.80 (d, J=4.9 Hz, 1 H), 2.40 (s, 1 H), 1.55 (s, 6 H), 1.28 (d, J=6.8 Hz, 6 H), 0.14 (s, 18 H); $^{13}$C NMR (CDCl₃, 75 MHz) δ 176.55, 152.73, 151.23, 149.40, 141.57, 122.32, 88.20, 86.40, 85.39, 84.67, 70.87, 69.89, 67.31, 62.62, 58.86, 36.09, 32.33, 32.30, 19.32, 1.80;

Dye conjugation of 28b with DR-N₃: Following similar procedural details described for the dye conjugation of 24b in Example 4A, 28c was produced in an 83% yield from 28b (24.5 g, 38.3 mmol). ¹H NMR (CDCl₃, 300 mHz) δ 8.65 (s, 1 H), 8.41 (b, 1 H), 8.32 (d, J=8.6 Hz, 2 H), 7.91 (d, J=8.6 Hz, 2 H), 7.82 (d, J=8.9 Hz, 2 H), 7.45 (s, 1 H), 6.65 (d, J=9.0 Hz, 2 H), 6.21 (d, J=3.2 Hz, 1 H), 4.55 (t, J=6.3 Hz, 2 H), 4.44 (q, J=5.7 Hz, 1 H), 4.17-4.09 (m, 2 H), 4.02 (dd, J=12.0 Hz, J=3.0 Hz, 1 H), 3.92-3.87 (m, 3 H), 3.54 (s, 3 H), 3.35-3.24 (m, 2 H), 3.07 (d, J=6.3 Hz, 1H), 1.67 (s, 6 H), 1.28 (d, J=6.9 Hz, 6 H), 1.09 (t, J=7.0 Hz, 3 H), 0.10 (s, 18 H); ¹³C NMR (CDCl₃, 75.5 mHz) δ 176.55, 156.73, 156.22, 152.74, 151.00, 150.62, 149.29, 147.77, 144.23, 141.44, 126.40, 124.88, 122.91, 121.20, 111.52, 86.64, 84.79, 84.40, 72.43, 69.08, 61.97, 58.99, 50.71, 47.74, 45.99, 36.12, 30.99, 30.85, 19.38, 19.36, 12.32, 1.85.

Phosphitylation of 28c: Following similar procedural details described for the phosphitylation of 24c in Example 4A, 28d was produced in a 95% yield from 28c (31.0 g, 31.7 mmol). ¹H NMR (CD₃CN, 300 mHz) δ 8.65 (b, 1 H), 8.55 (s, 1 H), 8.39 and 8.38 (each as s, 1 H), 8.32 (d, J=8.9 Hz, 2 H), 7.89 (d, J=8.9 Hz, 2 H), 7.74 (d, J=9.0 Hz, 2 H), 7.65 and 7.64 (each as s, 1 H), 6.65 (d, J=7.7 Hz, 2 H), 6.11 (t, J=4.5 Hz, 1 H), 4.62-4.53 (m, 3 H), 4.43-4.37 (m, 1 H), 4.25-4.21 (m, 1 H), 3.96 and 3.92 (each as d, J=3.4 Hz, 1 H), 3.87-3.78 (m, 3 H), 3.70-3.57 (m, 2 H), 3.44-3.32 (m, 6 H), 3.30-3.24 (m, 2 H), 3.10 (p, J=6.8 Hz, 1 H), 1.62 and 1.61 (each as s, 6 H) 1.22-1.16 (m, 18 H), 1.05 (t, J=5.3 Hz, 3 H), 0.1 and 0.09 (each as s, 18 H); ³¹P NMR (CD₃CN, 121.5 mHz), δ 151.18, 149.89.

F. 5'-DR(OTMS)₂-Silyl-OMe G(NiBu) Amidite (29d):

Silylation of 29a: Following similar procedural details described for the silylation of 24a in Example 4A, 29b was produced in a 71% yield from 29a (18.4 g, 50.0 mmol). ¹H NMR (CDCl₃, 300 mHz) δ 9.99 (s, 1 H), 8.13 (s, 1 H), 5.91 (d, J=5.6 Hz, 1 H), 4.43 (q, J=3.6 Hz, 1 H), 4.15-4.11 (m, 2 H), 3.96-3.85 (m, 2 H), 3.30 (s, 3 H), 3.17 (d, J=4.0 Hz, 1 H), 2.78 (p, J=6.8 Hz, 1 H), 2.41 (s, 1 H), 1.50 (s, 6 H), 1.21-1.17 (m, 6 H), 0.10 (s, 18 H); ¹³C NMR (CDCl₃, 75.5 mHz) δ 179.66, 162.91, 159.09, 148.71, 148.17, 137.50, 121.13, 88.13, 85.78, 85.60, 84.93, 70.97, 70.38, 67.33, 63.18, 58.45, 36.71, 36.31, 32.33, 31.63, 19.16, 1.80.

Dye conjugation of 29b with DR-N₃: Following similar procedural details described for the dye conjugation of 24b in Example 4A, 29c was produced in an 80% yield from 29b (23.3 g, 35.6 mmol). ¹H NMR (CDCl₃, 300 mHz) δ 9.12 (b, 1 H), 8.30 (d, J=8.7 Hz, 2 H), 8.13 (s, 1 H), 7.92-7.75 (m, 5 H), 6.62 (d, J=9.2 Hz, 2 H), 5.91 (d, J=4.8 Hz, 1 H), 4.70-4.68 (m, 2 H), 4.38 (q, J=4.3 Hz, 1 H), 4.13-4.06 (m, 3 H), 3.94-3.80 (m, 4 H), 3.39-3.30 (m, 5 H), 3.16 (d, J=4.7 Hz, 1 H), 2.66 (p, J=6.9 Hz, 1 H), 2.02 (s, 2 H), 1.64 (s, 6 H), 1.21 (d, J=6.9 Hz, 8 H), 1.10 (t, J=6.8 Hz, 3 H), 0.09 (d, J=7.9 Hz, 18 H); ¹³C NMR (CDCl₃, 75.5 mHz) δ 178.96, 156.86, 155.94, 155.73, 151.04, 148.29, 147.87, 147.55, 144.04, 137.55, 126.41, 126.34, 124.82, 122.91, 121.81, 121.87, 121.42, 111.50, 85.96, 85.17, 84.83, 72.64, 69.82, 62.38, 60.56, 58.83, 50.56, 47.86, 45.60, 36.49, 30.99, 30.74, 21.22, 19.22, 19.12, 14.35, 12.20, 1.80.

Phosphitylation of 29c: Following similar procedural details described for the phosphitylation of 24c in Example 4A, 29d was produced in an 87% yield from 29c (28.4 g, 28.5 mmol). ¹H NMR (CD₃CN, 300 mHz) δ 8.30 (d, J=9.0 Hz, 2 H), 8.11 and 8.10 (each as s, 1 H), 7.88 (d, J=9.1 Hz, 2 H), 7.74 (d, J=9.2 Hz, 2 H), 7.72 and 7.71 (each as s, 1 H), 6.65 (d, J=8.3 Hz, 2 H), 5.89 and 5.88 (each as d, J=3.5 Hz, 1 H), 4.59 (t, J=5.8 Hz, 2 H), 4.51-4.44 (m, 1 H), 4.22-4.16 (m, 2 H), 3.91-3.75 (m, 4 H), 3.67-3.52 (m, 2 H), 3.41 and 3.39 (each as s, 3 H), 3.36-3.28 (m, 5 H), 2.70-2.60 (m, 1 H), 1.63 (s, 6 H), 1.19-1.15 (m, 18 H), 1.07 (t, J=6.9 Hz, 3 H), 0.13-0.10 (m, 18 H); ³¹P NMR (CD₃CN, 121.5 mHz) δ 151.10, 150.36.

G. 5'-DR(OTMS)₂-Silyl-2'-OMe-C(NAc) Amidite (30d):

Silylation of 30a: Following similar procedural details described for the silylation of 24a in Example 4A, 30b was produced in a 77% yield from 30a (15.0 g, 50.0 mmol). ¹H NMR (CDCl₃, 300 mHz) δ 8.56 (d, J=7.5 Hz, 1 H), 8.48 (b, 1 H), 7.39 (d, J=7.4 Hz, 1 H), 6.01 (s, 1 H), 4.28-4.22 (m, 1 H), 4.16 (dd, J=12.0 Hz, J=2.3 Hz, 1 H), 3.98 (s, 1 H), 3.95 (d, J=2.4 Hz, 1 H), 3.75 (d, J=5.3 Hz, 1H), 3.70 (s, 3 H), 2.56 (d, J=9.6 Hz, 1 H), 2.41 (s, 1 H), 2.20 (s, 3 H), 1.56-1.54 (m, 6 H), 0.15 (s, 18 H); ¹³C NMR (CDCl₃, 75.5 mHz) δ 171.18, 163.37, 155.22, 145.44, 88.24, 88.18, 84.32, 84.26, 70.95, 67.49, 67.36, 60.67, 58.93, 32.38, 24.99, 1.81.

Dye conjugation of 30b with DR-N₃: Following similar procedural details described for the dye conjugation of 24b in Example 4A, 30c was produced in an 88% yield from 30b (22.7 g, 38.6 mmol). ¹H NMR (CDCl₃, 300 mHz) δ 8.48 (d, J=7.5 Hz, 1 H), 8.42 (b, 1 H), 8.32 (d, J=8.9 Hz, 2 H), 7.91 (d, J=8.9 Hz, 2 H), 7.87 (d, J=9.0 Hz, 2 H), 7.42 (s, 1 H), 7.31 (d, J=7.4 Hz, 1 H), 6.69 (d, J=9.1 Hz, 2 H), 5.94 (s, 1 H), 4.57 (t, J=6.4 Hz, 2 H), 4.22-4.14 (m, 1 H), 4.11-4.04 (m, 1 H), 3.95-3.90 (m, 4 H), 3.73-3.69 (m, 4 H), 3.30 (q, J=7.1 Hz, 2 H), 3.04 (d, J=9.6 Hz, 1 H), 2.17 (s, 3 H), 1.65 (s, 6 H), 1.56 (s, 1 H), 1.11 (t, J=7.1 Hz, 3 H), 0.11 (s, 18 H); ¹³C NMR (CDCl₃, 75.5 mHz) δ 170.64, 162.84, 156.74, 156.22, 155.07, 150.66, 147.77, 145.21, 144.27, 126.45, 124.88, 122.92, 121.02, 111.55, 96.45, 88.37, 84.10, 83.87, 72.46, 67.03, 60.59, 60.47, 58.97, 50.72, 47.68, 45.99, 31.00, 30.92, 25.10, 13.50, 1.87.

Phosphitylation of 30c: Following similar procedural details described for the phosphitylation of 24c in Example 4A, 30d was produced in a 90% yield from 30c (31.5 g, 34.0 mmol). ¹H NMR (CD₃CN, 300 mHz) δ 8.89 (b, 1 H), 8.34-8.30 (m, 3 H), 7.90 (d, J=9.8 Hz, 2 H), 7.79 (d, J=9.1 Hz, 2 H), 7.55 and 7.54 (each as s, 1 H), 7.24 (d, J=7.5 Hz, 1 H), 6.68 (d, J=9.2 Hz, 2 H), 5.90-5.87 (m, 1 H), 4.56 (t, J=5.9 Hz, 2 H), 4.33-4.18 (m, 1 H), 4.12-4.07 (m, 1 H), 4.03-3.99 (m, 1 H), 3.90-3.77 (m, 4 H), 3.64-3.53 (m, 2 H), 3.50 and 3.48 (each as s, 3 H), 3.37-3.27 (m, 5 H), 2.10 (s, 3 H), 1.62-1.59 (m, 6 H), 1.14-1.07 (m, 15 H), 0.11-0.10 (m, 18 H); ³¹P NMR (CD₃CN, 121.5 mHz) δ 150.58, 150.03.

H. 5'-DR(OTMS)₂-Silyl-2'-OMe-U Amidite (31d):

Silylation of 31a: Following similar procedural details described for the silylation of 24a in Example 4A, 31b was produced in a 75% yield from 31a (12.9 g, 50.0 mmol). ¹H NMR (CDCl₃, 300 mHz) δ 8.99 (b, 1 H), 8.02 (d, J=8.2 Hz, 1 H), 6.01 (d, J=3.2 Hz, 1 H), 5.70 (d, J=8.1 Hz, 1 H), 4.32-4.26 (m, 1 H), 4.12-3.96 (m, 2 H), 3.96-3.93 (m, 1 H), 3.77 (dd, J=5.0 Hz, J=3.3 Hz, 1 H), 3.56 (s, 3 H), 2.38 (s, 1 H), 1.52 (s, 6 H), 0.13 (s, 18 H); ¹³C NMR (CDCl₃, 75.5 mHz) δ 163.95, 150.67, 140.50, 102.55, 88.10, 86.87, 84.55, 84.12, 70.86, 68.51, 67.31, 61.57, 58.75, 32.33, 1.84.

Dye conjugation of 31b with DR-N₃: Following similar procedural details described for the dye conjugation of 24b in Example 4A, 31c was produced in an 83% yield from 31b (20.0 g, 36.6 mmol). ¹H NMR (CDCl₃, 300 mHz) δ 9.38 (b, 1 H), 8.27 (d, J=7.2 Hz, 2 H), 7.93-7.82 (m, 5 H), 7.35 (s, 1 H), 6.66 (d, J=9.2 Hz, 2 H), 5.90 (d, J=1.9 Hz, 1 H), 5.55 (d, J=8.1 Hz, 1 H), 4.54 (t, J=6.2 Hz, 2 H), 4.24-4.17 (m, 1 H), 4.01-3.83 (m, 4 H), 3.69 (dd, J=5.2 Hz, J=1.9 Hz, 1 H), 3.55 (s, 3 H), 3.28 (q, J=7.1 Hz, 2 H), 3.09 (d, J=8.0 Hz, 1 H), 1.63 (s, 6 H), 1.10 (t, J=7.0 Hz, 3 H), 0.07 (s, 18 H); ¹³C NMR (CDCl$_3$, 75.5 mHz) δ 163.84, 156.66, 156.09, 150.62, 150.46, 147.65, 144.18, 140.26, 126.40, 124.51, 122.87, 120.98, 111.50, 102.17, 87.13, 84.06, 84.00, 72.37, 67.83, 61.06, 58.78, 50.66, 47.70, 45.96, 30.91, 12.29, 1.85.

Phosphitylation of 31c: Following similar procedural details described for the phosphitylation of 24c in Example 4A, 31d was produced in a 91% yield from 31c (26.2 g, 30.2 mmol). $^1$H NMR (CD$_3$CN, 300 mHz) δ 9.24 (b, 1 H), 8.30 (d, J=9.0 Hz, 2 H), 7.88 (d, J=8.9 Hz, 2 H), 7.88-7.74 (m, 3 H), 7.54 and 7.53 (each as s, 1 H), 6.69 (d, J=9.2 Hz, 2 H), 5.88 (d, J=5.0 Hz, 1 H), 5.51 and 5.50 (each as d, J=8.1 Hz, 1 H), 4.56 (t, J=5.9 Hz, 2 H), 4.36-4.27 (m, 1 H), 4.12-4.07 (m, 1 H), 3.90-3.74 (m, 5 H), 3.40-3.28 (m, 8 H), 1.60 and 1.59 (each as s, 6 H), 1.71-1.07 (m, 15 H), 0.10 and 0.09 (each as s, 18 H); $^{31}$P NMR (CD$_3$CN, 121.5 mHz) δ 151.06, 150.13.

I. 5'-DR(OTMS)$_2$-Silyl-2'-F-C(NAc) Amidite (32d):

Silylation of 32a: N-acetyl protection of 32a (24.5 g, 100 mmol) was carried out in the same fashion as described in Example 2I. The silylation was performed following similar procedural details described for the silylation of 24a in Example 4A and with the exception of adding 100 mL of Dimethylformamide to help dissolve 32a, 32b was produced in a 65% yield from 32a (24.5 g, 100 mmol). $^1$H NMR (CDCl$_3$, 300 mHz) δ 10.16 (b, 1 H), 8.38 (d, J=7.6 Hz, 1 H), 7.37 (d, J=7.6 Hz, 1 H), 5.97 (d, J=15.5 Hz, 1 H), 4.94 (dd, J=52.0 Hz, J=3.51 Hz, 1 H), 4.46-4.43 (m, 1 H), 4.24-4.08 (m, 3 H), 3.91-3.88 (m, 1 H), 2.37 (s, 1 H), 2.17 (s, 3 H), 1.45 (s, 6 H), 0.05 (s, 18 H); $^{13}$C NMR (CDCl$_3$, 75.5 mHz) δ 171.18, 163.24, 155.21, 144.86, 96.97, 95.41, 92.92, 89.01, 88.56, 87.95, 82.88, 70.90, 67.59, 67.36, 67.18, 60.29, 32.17, 24.82, 1.67; $^{19}$F NMR (CDCl$_3$, 282.4 mHz) δ −203.35.

Dye conjugation of 32b with DR-N$_3$: Following similar procedural details described for the dye conjugation of 24b in Example 4A, 32c was produced in a 72% yield from 32b (37.7 g, 65.0 mmol). $^1$H NMR (CDCl$_3$, 300 mHz) δ 10.05 (b, 1 H), 8.44 (d, J=7.5 Hz, 1 H), 8.27 (d, J=8.8 Hz, 2 H), 7.88 (d, J=8.8 Hz, 2 H), 7.83 (d, J=9.0 Hz, 2 H) 7.43-7.40 (m, 2 H), 6.68 (d, J=9.0 Hz, 2 H), 6.04 (d, J=15.9 Hz, 1 H), 5.47-5.44 (m, 1 H) 5.05 (dd, J=51.9 Hz, J=3.6 Hz, 1 H), 4.60 (t, J=6.0 Hz, 2 H), 4.44-4.34 (m, 1 H), 4.21-3.92 (m, 6 H), 3.32 (q, J=6.8 Hz, 2 H), 2.27 (s, 3 H), 1.65 (s, 6 H), 1.12 (t, J=6.9 Hz, 3 H), 0.14 (s, 18 H); $^{13}$C NMR (CDCl$_3$, 75.5 mHz) δ 171.28, 163.38, 162.95, 156.75, 155.60, 155.07, 150.73, 147.70, 144.96, 144.27, 126.50, 124.90, 122.98, 120.96, 111.62, 96.95, 95.70, 93.21, 89.47, 89.03, 82.88, 71.68, 67.00, 66.78, 60.66, 60.31, 50.66, 47.94, 46.05, 36.80, 31.71, 30.84, 30.78, 25.16, 21.31, 12.10, 1.97; $^{19}$F NMR (CDCl$_3$, 282.4 mHz) δ −202.42.

Phosphitylation of 32c: Following similar procedural details described for the phosphitylation of 24c in Example 4A, 32d was produced in a 65% yield from 32c (42.61 g, 46.6 mmol). $^1$H NMR (CD$_3$CN, 300 mHz) δ 9.18 (b, 1 H), 8.30-8.23 (m, 3 H), 7.84 (d, J=9.0 Hz, 2 H), 7.75 (d, J=9.1 Hz, 2 H), 7.55 and 7.54 (each as s, 1 H), 7.25 (d, J=7.6 Hz, 1 H), 6.65 (d, J=9.2 Hz, 2 H), 5.91 (d, J=17.3 Hz, 1 H), 4.97 (dt, J=51.6 Hz, J=4.9 Hz, 1 H), 4.56 (t, J=6.0 Hz, 2 H), 4.42-4.25 (m, 1 H), 4.14-4.06 (m, 2 H), 3.89-3.80 (m, 3 H), 3.70-3.48 (m, 2 H), 3.36-3.27 (m, 5 H), 2.10 (s, 3 H), 1.61-1.59 (m, 6 H), 1.12-1.05 (m, 15 H) 0.10-0.08 (m, 18 H); $^{19}$F NMR (CD$_3$CN, 283.4 mHz) δ −200.72, −200.75, −200.85, −200.87; $^{31}$P NMR (CD$_3$CN, 121.5 mHz) δ 151.29, 151.24, 151.07, 151.01.

J. 5'-DR(OTMS)$_2$-Silyl-2'-F-U Amidite (33d):

Silylation of 33a: Following similar procedural details described for the silylation of 24a in Example 4A, 33b was produced in a 78% yield from 33a (12.3 g, 50.0 mmol). $^1$H NMR (CDCl$_3$, 300 mHz) δ 7.96 (s, 1 H), 7.90 (d, J=8.1 Hz, 1 H), 6.13 (dd, J=14.7 Hz, J=2.8 Hz, 1 H), 5.68 (d, J=8.1 Hz, 1 H), 4.92 (dt, J=52.7 Hz, J=3.5 Hz, 1 H), 4.38-430 (m, 1 H), 4.11-3.90 (m, 3 H), 2.40 (s, 1 H), 1.49 (s, 6 H), 0.10 (s, 18 H); $^{13}$C NMR (CDCl$_3$, 75.5 mHz) δ 163.85, 162.93, 150.52, 140.24, 102.70, 95.02, 92.52, 88.01, 87.12, 86.67, 83.67, 70.93, 69.01, 68.79, 67.32, 61.42, 36.69, 32.25, 31.61, 1.75; $^{19}$F NMR (CDCl$_3$, 282.4 mHz) δ −206.13.

Dye conjugation of 33b with DR-N$_3$: Following similar procedural details described for the dye conjugation of 24b in Example 4A, 33c was produced in a 78% yield from 33b (21.0 g, 39.0 mmol). $^1$H NMR (CDCl$_3$, 300 mHz) δ 8.82 (b, 1 H), 8.29 (d, J=8.9 Hz, 2 H), 7.91-7.84 (m, 5 H), 7.29 (s, 1 H), 6.67 (d, J=9.1 Hz, 2 H), 6.00 (d, J=16.0 Hz, 1 H), 5.59 (d, J=8.1 Hz, 1 H), 4.93 (dd, J=52.4 Hz, J=4.1 Hz, 1 H), 4.88 (d, J=6.8 Hz, 1 H), 4.55 (t, J=6.0 Hz, 2 H), 4.46-4.37 (m, 1 H), 4.10-3.90 (m, 5 H), 3.29 (q, J=6.9 Hz, 2 H), 1.61 (s, 6 H), 1.10 (t, J=6.8 Hz, 3 H), 0.08 (s, 9 H), 0.06 (s, 9 H); $^{13}$C NMR (CDCl$_3$, 75.5 mHz) δ 163.15, 156.69, 155.47, 150.54, 150.03, 147.87, 144.33, 140.10, 126.45, 124.88, 122.95, 120.66, 116.59, 111.58, 102.27, 93.53, 93.03, 88.17, 87.72, 82.89, 71.52, 67.63, 67.41, 60.62, 50.59, 47.87, 46.06, 30.76, 30.69, 12.35, 20.9, 1.90, 1.81; $^{19}$F NMR (CDCl$_3$, 282.4 mHz) δ −202.68.

Phosphitylation of 33c: Following similar procedural details described for the phosphitylation of 24c in Example 4A, 33d was produced in an 82% yield from 33c (26.5 g, 30.4 mmol). $^1$H NMR (CD$_3$CN, 300 mHz) δ 9.40 (b, 1 H), 8.32 (d, J=9.0 Hz, 2 H), 7.90 (d, J=9.0 Hz, 2 H), 7.80 (d, J=9.2 Hz, 2 H), 7.74 and 7.73 (each as d, J=2.2 Hz, 1 H), 7.57 and 7.56 (each as s, 1 H), 6.71 (d, J=9.3 Hz, 2 H), 5.94 (d, J=16.9 Hz, 1 H), 5.52 (each as d, J=3.2 Hz, 1 H), 5.13-5.11 and 4.95-4.94 (each as m, 1 H), 4.59 (t. J=6.0 Hz, 2 H), 4.52-4.34 (m, 1 H), 4.13-4.01 (m, 1 H), 3.93-3.86 (m, 4 H), 3.65-3.56 (m, 2 H), 3.40-3.33 (m, 5 H), 1.62 (s, 6 H), 1.17-1.12 (m, 15 H), 0.12-0.11 (m, 18 H); $^{19}$F NMR (CD$_3$CN, 282.4 mHz) δ −201.48, −201.51, −202.13, −202.16; $^{31}$P NMR (CD$_3$CN, 121.5 mHz) δ 151.42, 151.35, 151.03, 150.94.

Example 5

Synthesis 5'-DB and AR (OiPr)$_2$ Silyl Amidites

A. 5'-DB(OiPr)-Silyl-rG(iBu) Amidite (34b):

Dye conjugation of 5b with DB-N$_3$: Copper Iodide (0.03 g, 0.19 mmol) was added to a solution of 5b (1.54 g, 1.92 mmol), DB-N$_3$ (1.0 g, 2.89 mmol), and iPr$_2$NEt (0.25 g, 1.92 mmol) in 38 mL of Toluene. The solution was sonicated for 1 min and then stirred at room temperature for 1 h. The solution was then partitioned between ethyl acetate and saturated NaCl. The aqueous phase was back extracted once with ethyl acetate to remove all blue color from the water layer. The organic phases were combined and concentrated. The crude material was purified by flash chromatography on 300 mL silica gel using a gradient of ethyl acetate and acetone in hexanes [2:2:6 (v/v/v) to 8:2:0 (v/v/v)] containing 0.1% (v/v) Et$_3$N. Product fractions were pooled and evaporated to afford 34a as a blue foam. The yield was 1.65 g (76%). $^1$H NMR (CD$_3$CN, 300 mHz) δ 9.82 (b, 1 H), 8.54 (s, 1 H), 8.09 (s, 1 H), 7.78 (s, 1 H), 7.70 (d, J=9.2 Hz, 2 H), 6.68 (d, J=9.2 Hz, 2 H), 5.95 (d, J=5.2 Hz, 1 H), 5.43 (s, 1 H), 4.71-4.63 (m, 3 H), 4.45-4.40 (m, 1 H), 4.25-4.16 (m, 2 H), 4.13-4.03 (m, 6 H), 3.98-3.83 (m, 5 H), 3.74-3.53 (m, 5 H), 3.44-3.37 (m, 2 H), 2.78-2.70 (m, 1 H), 1.97 (s, 3 H), 1.96 (s, 3 H), 1.63 (s, 6 H), 1.18 (d, J=6.6 Hz, 6 H), 1.14 (d, J=6.6 Hz, 12 H); $^{13}$C NMR (CD$_3$CN, 75.5 mHz) δ 182.63, 181.42, 172.01, 171.95, 156.70, 156.66, 155.68, 150.04, 149.63, 147.96, 145.55, 143.94, 138.93, 122.97, 122.13, 113.96, 113.83, 87.32, 86.22, 77.98, 73.46, 71.51, 67.52, 67.49, 67.38, 67.23, 64.33, 64.27, 64.18, 64.05, 51.63, 48.75, 47.08, 37.21, 31.54, 31.46, 26.15, 21.46, 21.14, 21.06, 19.72, 19.67, 12.87.

Phosphitylation of 34a: Bis(diisopropylamino) methoxy phosphine (0.57 g, 2.19 mmol) was dissolved in 3 mL of $CH_2Cl_2$ and a 0.5 M solution of 5-ethylthio-1-H-tetrazole in anhydrous acetonitrile (1.5 mL, 0.73 mmol) was added. Diisopropylamine (0.15 g, 1.46 mmol) was then added and the phosphine solution was allowed to stir for 5 min at ambient temperature. In a separate flask, 34a (1.65 g, 1.46 mmol) and diisopropylamine (0.15 g, 1.46 mmol) were dissolved in 3 mL of $CH_2Cl_2$. The activated phosphine solution was added into the nucleoside solution and the reaction was stirred at room temperature. After 16 h the reaction was quenched with 1 mL of absolute ethanol and concentrated to dryness. The resulting paste was purified by flash chromatography on 300 mL of silica gel using a mixture of $CH_2Cl_2$ in hexanes (5:95 (v/v) containing 2% (v/v) $Et_3N$ followed by acetone in hexanes (2:8 (v/v) to 4:6 (v/v) containing 0.5% (v/v) $Et_3N$. Product fractions were pooled and evaporated to afford 34b as blue foam. The yield was 1.0 g (53%). $^1H$ NMR ($CD_3CN$, 300 mHz) δ 8.59 (b, 1 H), 8.10 and 8.08 (each as s, 1 H), 7.76-7.65 (m, 3 H), 6.65-6.62 (m, 2 H), 5.98-5.93 (m, 1 H), 5.36 and 5.30 (each as s, 1 H), 4.75-4.60 (m, 3 H), 4.60-4.41 (m, 1 H), 4.30-4.15 (m, 3 H), 4.04-3.82 (m, 7 H), 3.70-3.45 (m, 7 H), 3.40-3.30 (m, 5 H), 2.79-2.64 (m, 1 H), 1.96-1.92 (m, 6 H), 1.58 and 1.57 (each as s, 6 H), 1.23-1.10 (m, 33 H); $^{31}P$ NMR ($CD_3CN$, 121.5 mHz) δ 151.05, 150.85.

B. 5'-AR(OiPr)$_2$-Silyl-rA (iBu) Amidite (35b):

Dye conjugation of 4b with AR-$N_3$: Copper Iodide (0.15 g, 0.77 mmol) was added to a solution of 4b (6.04 g, 7.7 mmol), AR-$N_3$ (2.92 g, 10.0 mmol), and $iPr_2NEt$ (1.0 g, 7.7 mmol) in 154 mL of Toluene. The solution was sonicated for 1 min and then stirred at room temperature for 2 h. The solution was then partitioned between ethyl acetate and saturated NaCl. The aqueous phase was back extracted once with ethyl acetate to remove all red color from the water layer. The organic phases were combined and concentrated. The crude material was purified by flash chromatography on 200 mL silica gel using a gradient of ethyl acetate and acetone in hexanes [2:2:6 (v/v/v) to 6:2:2 (v/v/v)] containing 0.1% (v/v) $Et_3N$. Product fractions were pooled and evaporated to afford 35a as red foam. The yield was 6.7 g (81%). $^1H$ NMR ($CDCl_3$, 300 mHz) δ 9.88 (bs, 1 H), 8.64 (s, 1 H), 8.32-8.19 (m, 4 H), 7.77-7.43 (m, 5 H), 6.88 (d, J=8.2 Hz, 1 H), 6.30 (d, J=4.2 Hz, 1 H), 5.50 (s, 1 H), 4.78 (t, J=4.7 Hz, 1 H), 4.61 (t, J=6.3 Hz, 2 H), 4.47 (q, J=5.0 Hz, 1 H), 4.25-4.08 (m, 7 H), 4.00-3.86 (m, 4 H), 3.81-3.70 (m, 3 H), 3.66-3.67 (m, 2 H), 3.29-3.21 (m, 1 H), 2.02 (s, 3 H), 2.00 (s, 3 H), 1.66 (s, 6 H), 1.28 (d, J=6.8 Hz, 6 H), 1.10 (d, J=6.1 Hz, 12 H).

Phosphitylation of 35a: Bis(diisopropylamino) methoxy phosphine (2.40 g, 9.3 mmol) was dissolved in 12 mL of $CH_2Cl_2$ and a 0.5 M solution of 5-ethylthio-1-H-tetrazole in anhydrous acetonitrile (6.2 mL, 3.1 mmol) was added. Diisopropylamine (0.63 g, 6.2 mmol) was then added and the phosphine solution was allowed to stir for 5 min at ambient temperature. In a separate flask, 35a (6.70 g, 6.2 mmol) and diisopropylamine (0.63 g, 6.2 mmol) were dissolved in 12 mL of $CH_2Cl_2$. The activated phosphine solution was added into the nucleoside solution and the reaction was stirred at room temperature. After 16 h the reaction was quenched with 2 mL of absolute ethanol and concentrated to dryness. The resulting paste was purified by flash chromatography on 250 mL of silica gel using a mixture of $CH_2Cl_2$ in hexanes (5:95 (v/v) containing 2% (v/v) $Et_3N$ followed by acetone in hexanes (2:8 (v/v) to 3:7 (v/v) containing 0.5% (v/v) $Et_3N$. Product fractions were pooled and evaporated to afford 35b as red foam. The yield was 6.4 g (83%). $^1H$ NMR ($CD_3CN$, 300 mHz) δ 9.72 (b, 1 H), 8.65 (s, 1 H), 8.56 and 8.54 (each as s, 1 H), 8.32 (s, 1 H), 8.19-8.12 (m, 2 H), 7.82-7.69 (m, 3 H), 7.52-7.45 (m, 2 H), 7.02-6.95 (m, 1 H), 5.31 and 5.27 (each as s, 1 H), 4.91-4.88 (m, 1 H), 4.63-4.51 (m, 3 H), 4.63-4.52 (m, 3 H), 4.22-4.11 (m, 3 H), 4.07-3.79 (m, 7 H), 3.68-3.48 (m, 6 H), 3.42-3.29 (m, 3 H), 3.09 (m, 1 H), 1.95-1.89 (m, 6 H), 1.63 and 1.61 (each as s, 6 H), 1.24-1.04 (m, 30 H); $^{31}P$ NMR ($CD_3CN$, 121.5 Hz) δ 150.98, 150.28.

Example 6

RNA Synthesis Conditions and Examples

All oligonucleotides were synthesized on an ABI 394 DNA/RNA synthesizer that has been adapted for 5'-silyl-2'-orthoester chemistry. Standard synthesis cycles developed for RNA synthesis utilizing 5'-BZH-silyl-protected phosphoramidites were used without modification (see U.S. Pat. No. 6,590,093) with the 5'-DR(OiPr)$_2$Silyl, -2'-ACE protected phosphoramidites. For the 5'-DRMe$_2$Silyl, -2'-ACE protected phosphoramidites and the 5'-DR(OTMS)$_2$Silyl, -2'-MP protected phosphoramidites the only modification to the standard cycle was the delivery time of $Et_3N$—HF. The delivery time of $Et_3N$—HF was increased from 35 s to 150 s and 120 s respectively. All phosphoramidites were diluted to 0.067 M in anhydrous acetonitrile and were coupled for 60 s. Oligonucleotide syntheses were performed on 0.2 and 0.5 umol scales and were performed along side a control synthesis of the same sequence that used standard 5'-BZH-silyl protected phosphoramidites. Upon completion of the synthesis, the immobilized RNA was deprotected, cleaved from the support, and analyzed using standard procedures.

Quantification of coupling efficiencies was accomplished by collection of the $Et_3N$—HF deprotection solution and the subsequent acetonitrile wash prior to entering the waste stream. The samples were then diluted to 10 or 25 mL (depending on synthesis scale) with 0.5 M $H_2SO_4$ and quantified at 540 nM using a UV-Vis spectrometer. The coupling efficiency (average stepwise yield) was calculated according to the following equation:

Average Stepwise Yield %=(Absorbance of the last coupling step/Absorbance of the first coupling step)$^{1/n}$×100 wherein "n" is the total number of coupling steps.

Figure 15:
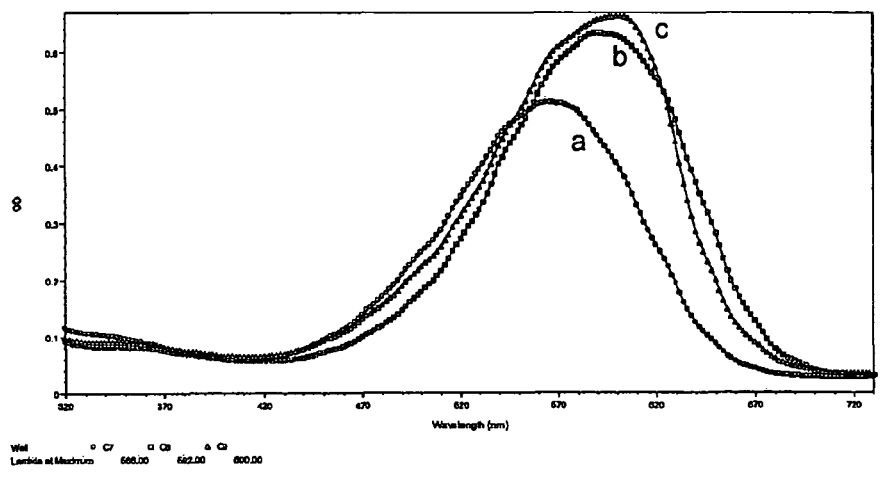
FIG. 15 shows UV-Vis spectral overlay of DB response in different solvents.
Figure 16:
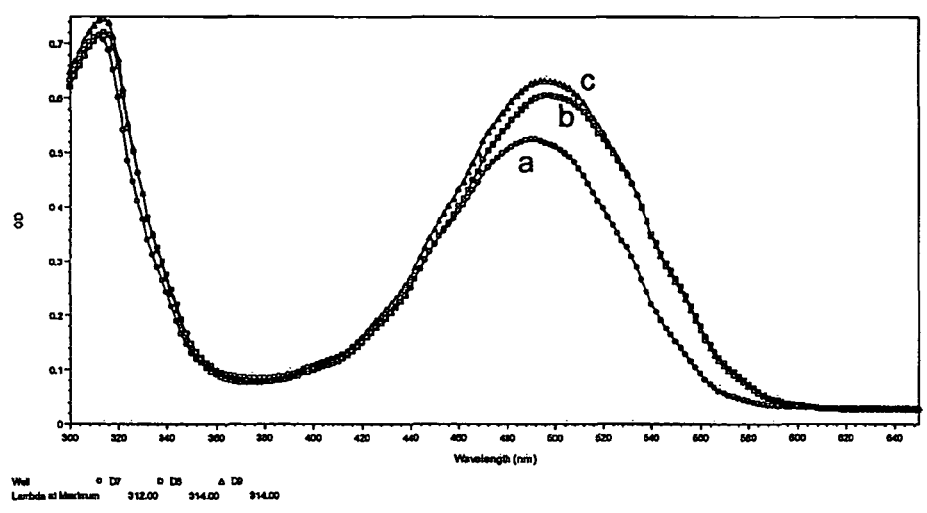
FIG. 16 shows UV-Vis spectral overlay of AR response in different solvents.
Figure 17:
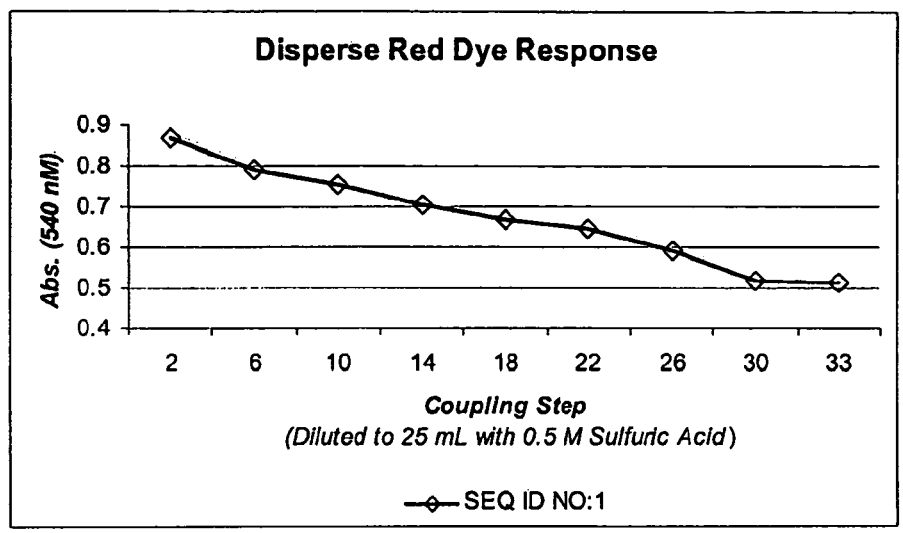
FIG. 17 is a plot of dye response versus coupling number from the synthesis of SEQ ID NO: 1.
Figure 18:
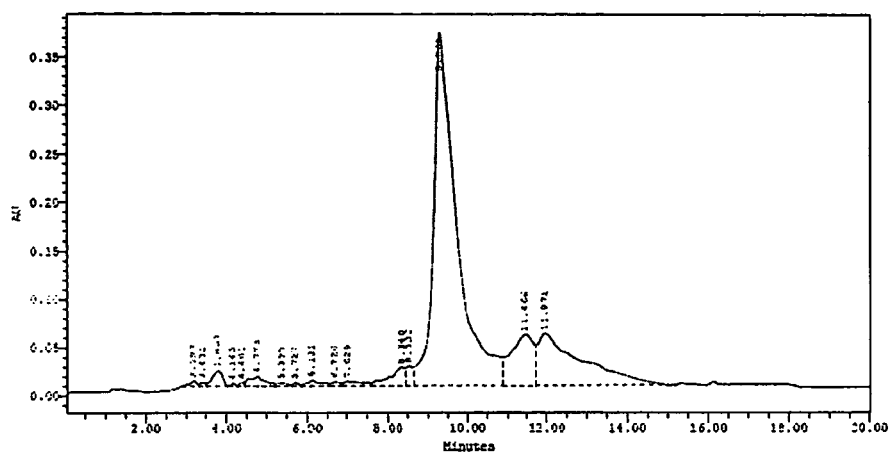
FIG. 18 is an anion-exchange HPLC chromatograph of unpurified 2'-protected SEQ ID NO: 1.
Figure 19:
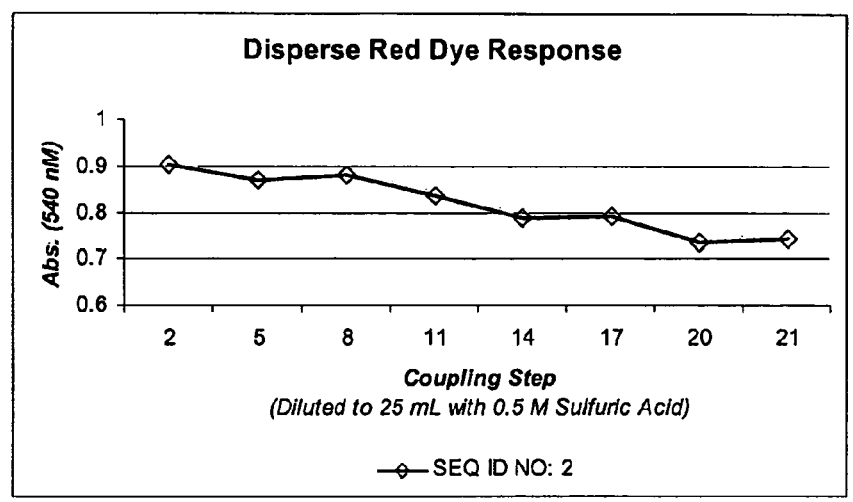
FIG. 19 is a plot of dye response versus coupling number from the synthesis of SEQ ID NO: 2.
Figure 20:
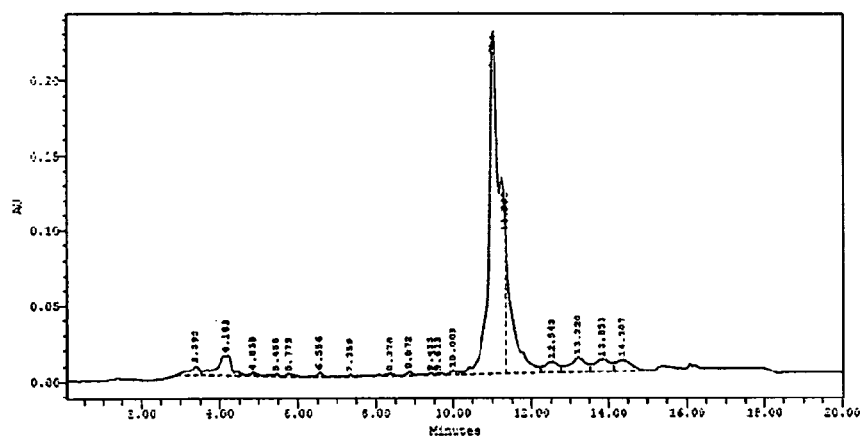
FIG. 20 is an anion-exchange HPLC chromatograph of unpurified 2'-protected SEQ ID NO: 2.
Figure 21:
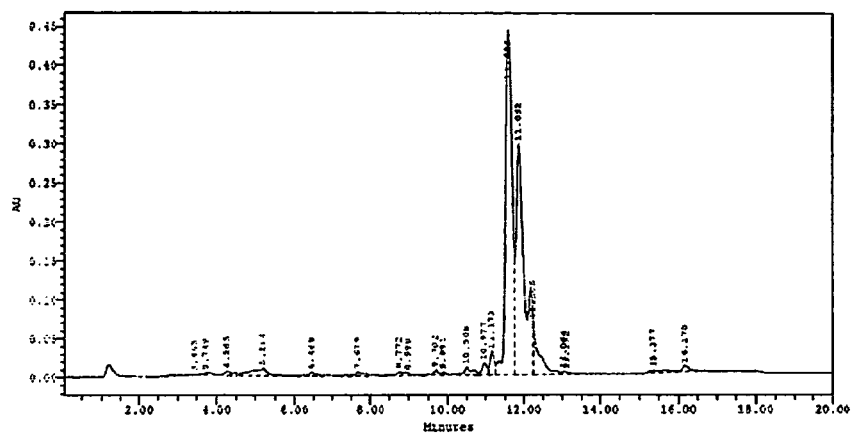
FIG. 21 is an anion-exchange HPLC chromatograph of unpurified 2'-protected SEQ ID NO: 3.
Figure 22:
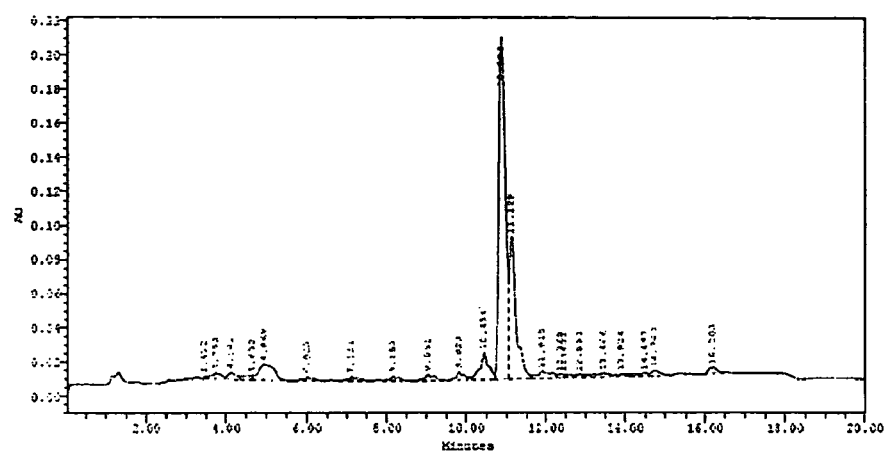
FIG. 22 is an anion-exchange HPLC chromatograph of unpurified 2'-protected SEQ ID NO: 4.
Figure 23:
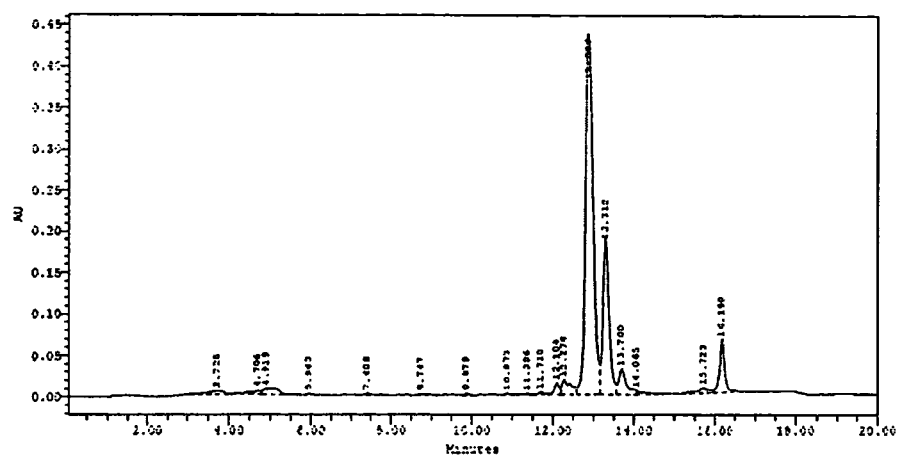
FIG. 23 is an anion-exchange HPLC chromatograph of unpurified 2'-protected SEQ ID NO: 5.
Figure 24:
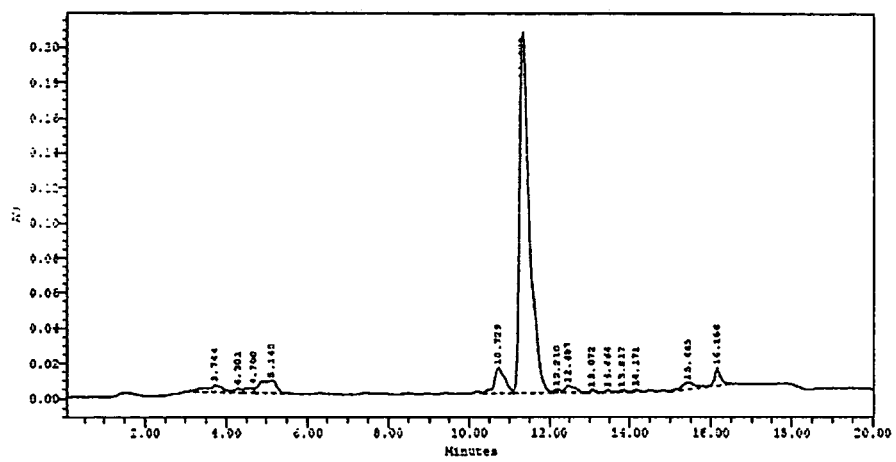
FIG. 24 is an anion-exchange HPLC chromatograph of unpurified 2'-protected SEQ ID NO: 6.
Figure 25:
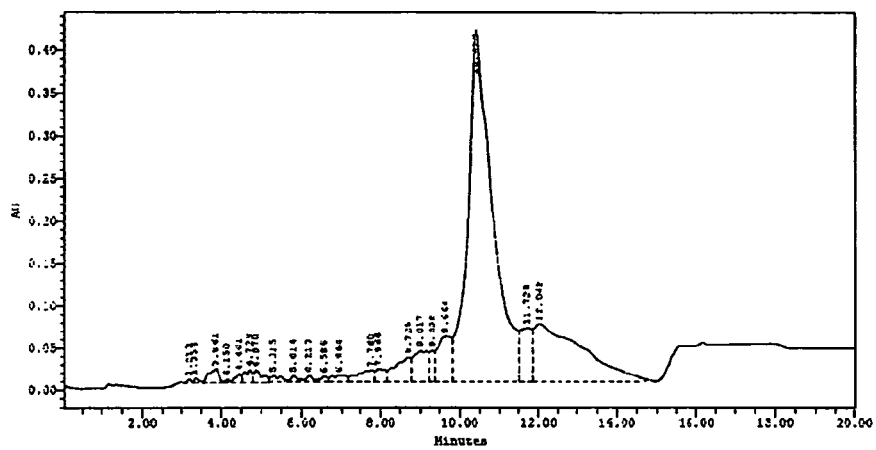
FIG. 25 is an anion-exchange HPLC chromatograph of unpurified 2'-protected SEQ ID NO: 7.
Figure 26:
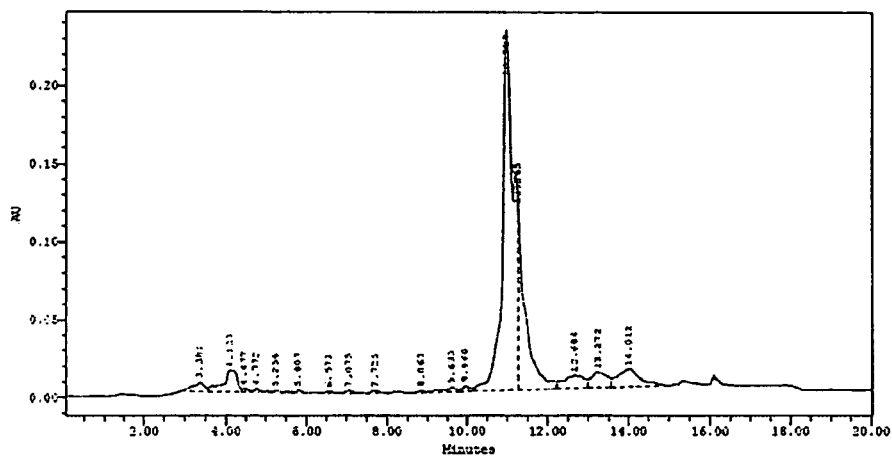
FIG. 26 is an anion-exchange HPLC chromatograph of unpurified 2'-protected SEQ ID NO: 8.

The following sequences were synthesized with 5'-DR(OiPr)$_2$Silyl, -2'-ACE protected phosphoramidites and coupling efficiencies were calculated and compared against the isolated yields (Table 1). For demonstration purposes the dye responses for SEQ ID NO: 1 and SEQ ID NO: 2 were plotted (FIGS. 15 and 17.) The anion exchange HPLC chromatograms for the following sequences are also presented in FIGS. 16 and 18-24.

```
                                           SEQ ID NO: 1
33 mer: GCAACUGCUA CGUGUCAUGC AGCUUCAUGC CAU SEQ ID NO: 2
21 mer: UCGAUCGAUC GAUCGAUCGA U SEQ ID NO: 3
12 mer: AAAAAAAAAA AA SEQ ID NO: 4
12 mer: CCCCCCCCCC CC
```

-continued

SEQ ID NO: 5

12 mer: GGGGGGGGGG GG

SEQ ID NO: 6

12 mer: UUUUUUUUUU UU

SEQ ID NO: 7

45 mer: AGCUAUCGGA UCGACUAUCA GUUAGGCGGA UUCAAUUGGC UAGCU

SEQ ID NO: 8

21 mer: GUUAACCGUC UGACUCAUGU U

TABLE 1

Isolated yields and calculated stepwise yields from the syntheses of SEQ ID NO: 1-8.

| SEQ ID NO: | Scale (nmol) | Length (nucleotides) | Isolated Yield (nmol) | Stepwise Yield (%) |
| --- | --- | --- | --- | --- |
| 1 | 200 | 33 | 192 | 98.8 |
| 2 | 200 | 21 | 175 | 98.6 |
| 3 | 200 | 12 | 198 | 99.5 |
| 4 | 200 | 12 | 171 | 99.5 |
| 5 | 200 | 12 | 215 | 98.2 |
| 6 | 200 | 12 | 184 | 99.1 |
| 7 | 200 | 45 | 167 | 99.4 |
| 8 | 200 | 21 | 191 | 99.3 |

Comparable tests were also performed with the 5'-DRMe$_2$Silyl, and 5'-DR(OTMS)$_2$Silyl phosphoramidites.

I claim:

1. A compound of the formula:

Y-Q-O—Si($R_1$)($R_2$)—X, wherein Y is an aromatic or heteroaromatic diazo chromophore-derived substituent;

-Q-O— is a 1,2,3-triazolyloxy moiety which is a silyl-to-chromophore linking group;

$R_1$ and $R_2$ are independently selected from the group consisting of $C_{1-8}$ alkyl, cycloalkyl, aryl, $C_{1-8}$ alkyloxy, cycloalkyloxy, trialkylsilyloxy and triarylsilyloxy; and X is a ribonucleotide-derived substituent moiety, a ribonucleoside-derived substituent moiety or an oligoribonucleotide-derived substituent moiety that is attached to the Si at a 5'-O-position and is protected at each of its 2'-O-positions.

2. The compound of claim 1, wherein X has 2' substituent(s) selected from the group consisting of O-acetoxyethyl (ACE); O-Me; F; and O-MP, wherein MP=

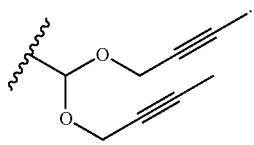

3. The compound of claim 1, wherein $R_1$ and $R_2$ are independently selected from the group consisting of $C_{1-8}$ trialkyloxy and $C_{1-4}$ trialkylsilyloxy.

4. The compound of claim 1, wherein the compound is selected from the group consisting of:

a 5'-DR-Q-O—Si(—O-iPr)$_2$ ribophosphoramidite,
    a 5'-DR-Q-O—Si(—O-Me)$_2$ ribophosphoramidite, and
    a 5'-DR-Q-O—Si(—O-TMS)$_2$ ribophosphoramidite, wherein DR is selected from the structures:

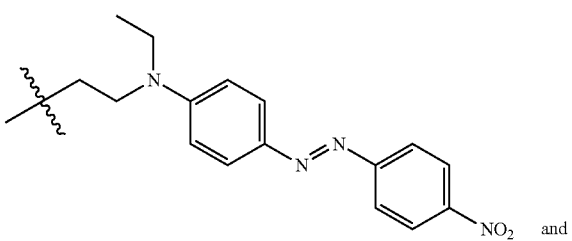 and

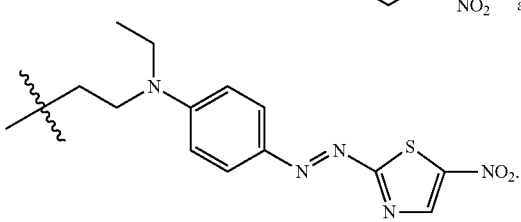

5. A compound of the formula:

$L_1$-O—Si($R_1$)($R_2$)—X, wherein $L_1$ is a substituent selected from the group consisting of a moiety derived from an azido moiety, wherein the azido moiety is capable of 1,3-dipolar cycloaddition with an alkyne compound in the presence a copper (I) salt to yield a 1,2,3-triazole, and an alkynyl moiety, wherein the alkynyl moiety is capable of 1,3-dipolar cycloaddition with an azide compound;

$R_1$ and $R_2$ are independently selected from the group consisting of $C_{1-8}$ alkyl, cycloalkyl, aryl, $C_{1-8}$ alkyloxy, cycloalkyloxy, trialkylsilyloxy and triarylsilyloxy; and X is an oligoribonucleotide-derived substituent moiety, a ribonucleotide-derived substituent moiety or a ribonucleoside-derived substituent moiety that is attached to the Si at a 5'-O-position.

6. A method of synthesizing a compound of formula Y-Q-O—$Si(R_1)(R_2)$—X comprising, wherein Y is a chromophore-derived substituent;

-Q-O— is a 1,2,3-triazolyloxy moiety which is a silyl-to-chromophore linking group;

$R_1$ and $R_2$ are independently selected from the group consisting of $C_{1-8}$ alkyl, cycloalkyl, aryl, $C_{1-8}$ alkyloxy, cycloalkyloxy, trialkylsilyloxy and triarylsilyloxy; and X is a ribonucleoside moiety that is attached to the Si at a 5' position;

the method comprising reacting a compound of formula $L_1$-O—$Si(R_1)(R_2)$—X with a compound of formula Y-$L_2$ in the presence of a catalytic amount of a Cu(I) compound under conditions that if X has a 3'OH group or a protecting group at a position other than the 5' position, permit Y-$L_2$ to covalently react with $L_1$-O—Si$(R_1)(R_2)$—X without reacting with said 3'OH group or protecting group at said position other than the 5' position, wherein $L_1$ and $L_2$ are independently substituents selected from the group consisting of an azido moiety and an alkynyl moiety; and whereby $L_1$ and $L_2$ react to form the moiety Q, wherein one of $L_1$ and $L_2$ is an azido moiety and the other one of $L_1$ and $L_2$ is an alkynyl moiety; and wherein the azido moiety and the alkynyl moiety undergo 1,3-dipolar cycloaddition in the presence a copper (I) salt to yield a 1,2,3-triazolyl linking moiety.

7. The method of claim 6 further comprising
a. reacting a compound of formula $L_1$-O—$Si(R_1)(R_2)(Z)$ with a 5',3'-dideprotected-2'-protected ribonucleoside represented by variable X; and
b. purifying via chromatography the resulting precursor $L_1$—O—$Si(R_1)(R_2)$—X;

wherein Z is halo, imidazolyl, triazolyl, tetrazolyl, trifluoromethylsulfonyl, alkylamino or dialkylamino.

8. The method of claim 6 further comprising
a. reacting a compound of formula $L_1$-O—$Si(R_1)(R_2)$Cl with X; and
b. purifying via chromatography the resulting precursor $L_1$ -O—$Si(R_1)(R_2)$—X.

9. The method of claim 6 further comprising
a. reacting a compound of formula $L_1$-O—$Si(R_1)(R_2)(Z)$ with an appropriately monodeprotected ribonucleoside moiety; and
b. purifying via chromatography the resulting precursor, $L_1$ -O—$Si(R_1)(R_2)$-ribonucleoside;
wherein Z is N, N-diisopropylamino.

10. The method of claim 6, wherein $L_1$ is an alkynyl moiety and $L_2$ is an azido moiety, and the copper (I) catalyst catalyzes the cycloaddition of said moieties.

11. A method of synthesizing a substrate-bound oligonucleotide comprising:
a. providing a substrate bound, appropriately protected ribonucleotide, ribonucleoside or oligoribonucleotide having a 5'-O-protecting group of the formula Y-Q-O—$Si(R_1)(R_2)$;
wherein Y is a chromophore-derived substituent;
-Q-O— is a 1,2,3-triazolyloxy moiety which is a silyl-to-chromophore linking group; and
$R_1$ and $R_2$ are independently selected from the group consisting of $C_{1-8}$ alkyl, cycloalkyl, aryl, $C_{1-8}$ alkyloxy, cycloalkyloxy, trialkylsilyloxy and triarylsilyloxy;
b. removing the 5'-O-protecting group by contact with a solution comprising fluoride ion and thereby providing a free 5'-OH group;
c. reacting an appropriately protected ribonucleoside monomer having a 3'-phosphoramidityl substituent with the substrate-bound ribonucleotide, ribonucleoside or oligoribonucleotide whereby the 3'-phosphoramidityl substituent is coupled to the 5'-OH of the substrate-bound ribonucleotide, ribonucleoside or oligoribonucleotide to form a phosphite triester; and
d. reacting the phosphite triester formed in (c) with a suitable oxidizing agent to convert it to a phosphate triester.

12. The method of claim 11 wherein steps a through d are repeated.

13. The method of claim 11 wherein the nucleoside monomer and substrate bound ribonucleotide, ribonucleoside or oligoribonucleotide further comprise a 2'-O-protecting group.

14. The method of claim 11 further comprising detecting the 5'-O-protected group removed in step b.

\* \* \* \* \*